United States Patent
Guo et al.

(10) Patent No.: US 12,252,708 B2
(45) Date of Patent: *Mar. 18, 2025

(54) LIVING MAMMALIAN CELLS MODIFIED WITH FUNCTIONAL MODULAR NANOPARTICLES

(71) Applicant: UNM Rainforest Innovations, Albuquerque, NM (US)

(72) Inventors: Jimin Guo, Albuquerque, NM (US); C. Jeffrey Brinker, Albuquerque, NM (US); Wei Zhu, Albuquerque, NM (US); Jacob Ongudi Agola, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 809 days.

This patent is subject to a terminal disclaimer.

(21) Appl. No.: 17/277,256

(22) PCT Filed: Sep. 24, 2019

(86) PCT No.: PCT/US2019/052658
§ 371 (c)(1),
(2) Date: Mar. 17, 2021

(87) PCT Pub. No.: WO2020/068798
PCT Pub. Date: Apr. 2, 2020

(65) Prior Publication Data
US 2022/0033768 A1    Feb. 3, 2022

Related U.S. Application Data

(60) Provisional application No. 62/735,585, filed on Sep. 24, 2018.

(51) Int. Cl.
C12N 5/00     (2006.01)
C12N 5/071    (2010.01)

(52) U.S. Cl.
CPC ......... *C12N 5/0012* (2013.01); *C12N 5/0602* (2013.01)

(58) Field of Classification Search
CPC .... C12N 5/0012; C12N 5/0602; B82Y 30/00; B82Y 5/00
See application file for complete search history.

(56) References Cited

U.S. PATENT DOCUMENTS

| | | | |
|---|---|---|---|
| 4,927,637 A | 5/1990 | Morano et al. | |
| 5,057,296 A | 10/1991 | Beck | |

(Continued)

FOREIGN PATENT DOCUMENTS

| | | |
|---|---|---|
| EP | 1852393 A1 | 11/2007 |
| JP | 2009515520 A | 4/2009 |

(Continued)

OTHER PUBLICATIONS

Park et al. 2017. "Artificial spores: immunoprotective nanocoating of red blood cells with supramolecular ferric ion-tannic acid complex." Polymers 9.4: 140). (Year: 2017).*

(Continued)

*Primary Examiner* — Aaron J Kosar
*Assistant Examiner* — Andrew T Moehlman
(74) *Attorney, Agent, or Firm* — Schwegman Lundberg & Woessner, P.A.

(57) ABSTRACT

An encapsulated living (viable) mammalian cell, and methods of making and using that cell, are provided.

11 Claims, 36 Drawing Sheets

(56) References Cited

U.S. PATENT DOCUMENTS

| | | |
|---|---|---|
| 5,098,684 A | 3/1992 | Kresge et al. |
| 5,360,834 A | 11/1994 | Popall et al. |
| 5,689,574 A | 11/1997 | Heirich et al. |
| 5,789,230 A | 8/1998 | Cotten |
| 6,194,388 B1 | 2/2001 | Krieg et al. |
| 6,365,266 B1 | 4/2002 | MacDougall et al. |
| 6,387,453 B1 | 5/2002 | Brinker et al. |
| 6,808,867 B2 | 10/2004 | Doshi et al. |
| 6,913,832 B2 | 7/2005 | Fan et al. |
| 7,101,967 B2 | 9/2006 | Fischer et al. |
| 7,332,264 B2 | 2/2008 | Doshi et al. |
| 7,514,267 B1 | 4/2009 | Lopez et al. |
| 7,563,451 B2 | 7/2009 | Lin et al. |
| 8,268,962 B2 | 9/2012 | Heemskerk et al. |
| 8,374,816 B2 | 2/2013 | Vu |
| 8,734,816 B2 | 5/2014 | Liu et al. |
| 8,926,994 B2 | 1/2015 | Serda et al. |
| 8,992,984 B1 | 3/2015 | Brinker et al. |
| 9,480,653 B2 | 11/2016 | Brinker et al. |
| 9,579,283 B2 | 2/2017 | Brinker et al. |
| 9,855,217 B2 | 1/2018 | Brinker et al. |
| 9,989,447 B1 | 6/2018 | Kaehr et al. |
| 10,022,327 B2 | 7/2018 | Brinker et al. |
| 10,465,189 B2 | 11/2019 | Venkatraman et al. |
| 11,344,629 B2 | 5/2022 | Brinker et al. |
| 11,672,866 B2 | 6/2023 | Durfee et al. |
| 2002/0147105 A1 | 10/2002 | Shamshoum et al. |
| 2004/0005352 A1 | 1/2004 | Lopez et al. |
| 2004/0258671 A1 | 12/2004 | Watkins |
| 2005/0239687 A1 | 10/2005 | Divita et al. |
| 2006/0154069 A1 | 7/2006 | Lin et al. |
| 2007/0224257 A1 | 9/2007 | Commander et al. |
| 2007/0287104 A1 | 12/2007 | Doshi et al. |
| 2007/0298093 A1 | 12/2007 | Konur et al. |
| 2008/0095852 A1 | 4/2008 | Kong et al. |
| 2008/0160313 A1 | 7/2008 | Lopez et al. |
| 2008/0213377 A1 | 9/2008 | Bhatia et al. |
| 2008/0241262 A1 | 10/2008 | Lee et al. |
| 2008/0241917 A1 | 10/2008 | Akita et al. |
| 2008/0286371 A1 | 11/2008 | Pacheco et al. |
| 2009/0054246 A1 | 2/2009 | Peabody et al. |
| 2009/0170931 A1 | 7/2009 | Faulds et al. |
| 2009/0181090 A1 | 7/2009 | Dreis et al. |
| 2009/0208563 A1 | 8/2009 | Watkins et al. |
| 2009/0291131 A1 | 11/2009 | Maclachlan et al. |
| 2009/0305409 A1 | 12/2009 | Kogure et al. |
| 2010/0028341 A1 | 2/2010 | Hermans et al. |
| 2010/0055167 A1 | 3/2010 | Zhang et al. |
| 2010/0152699 A1 | 6/2010 | Ferrari et al. |
| 2010/0166665 A1 | 7/2010 | Butts et al. |
| 2010/0166808 A1 | 7/2010 | Pauletti et al. |
| 2010/0168120 A1 | 7/2010 | Watterson et al. |
| 2010/0255103 A1 | 10/2010 | Liong et al. |
| 2011/0059156 A9 | 3/2011 | Mirkin et al. |
| 2011/0097819 A1 | 4/2011 | Groves et al. |
| 2011/0135571 A1 | 6/2011 | Lin et al. |
| 2011/0230372 A1 | 9/2011 | Willman et al. |
| 2011/0268791 A1 | 11/2011 | Liu et al. |
| 2011/0300186 A1 | 12/2011 | Hellstrom et al. |
| 2012/0207795 A1 | 8/2012 | Zink et al. |
| 2013/0095039 A1 | 4/2013 | Lu et al. |
| 2013/0108661 A1 | 5/2013 | Blander et al. |
| 2013/0115169 A1 | 5/2013 | Lahann et al. |
| 2013/0122054 A1 | 5/2013 | Harashima et al. |
| 2013/0185823 A1 | 7/2013 | Kuang et al. |
| 2013/0195963 A1 | 8/2013 | Serda et al. |
| 2013/0197103 A1 | 8/2013 | Brown |
| 2014/0023700 A1 | 1/2014 | Knudsen et al. |
| 2014/0079774 A1 | 3/2014 | Brinker et al. |
| 2014/0141089 A1 | 5/2014 | Liang |
| 2014/0212479 A1 | 7/2014 | Zeinelden |
| 2014/0234210 A1 | 8/2014 | Lin et al. |
| 2014/0301951 A1 | 10/2014 | Liu et al. |
| 2015/0010475 A1 | 1/2015 | Brinker et al. |
| 2015/0118247 A1 | 4/2015 | Hotson et al. |
| 2015/0125384 A1 | 5/2015 | Mellman et al. |
| 2015/0125391 A1 | 5/2015 | Swami et al. |
| 2015/0164798 A1 | 6/2015 | Brinker et al. |
| 2015/0272885 A1 | 10/2015 | Ashley et al. |
| 2015/0320681 A1 | 11/2015 | Brinker et al. |
| 2016/0008283 A1 | 1/2016 | Nel et al. |
| 2016/0090603 A1 | 3/2016 | Carnes et al. |
| 2016/0106671 A1 | 4/2016 | Brinker et al. |
| 2016/0151482 A1 | 6/2016 | Carnes et al. |
| 2016/0193588 A1 | 7/2016 | Haynes et al. |
| 2016/0287717 A1 | 10/2016 | Brinker |
| 2016/0338954 A1 | 11/2016 | Brinker |
| 2016/0361411 A1 | 12/2016 | Gindy et al. |
| 2017/0042870 A1 | 2/2017 | Xue et al. |
| 2017/0165375 A1 | 6/2017 | Ashley et al. |
| 2017/0232115 A1 | 8/2017 | Ashley et al. |
| 2018/0028686 A1 | 2/2018 | Brinker et al. |
| 2018/0049984 A1 | 2/2018 | Brinker et al. |
| 2018/0105430 A1 | 4/2018 | Carnes et al. |
| 2018/0110831 A1 | 4/2018 | Brinker et al. |
| 2018/0344641 A1 | 12/2018 | Brinker et al. |
| 2019/0022235 A1 | 1/2019 | Durfee et al. |
| 2019/0091150 A1 | 3/2019 | Brinker et al. |
| 2019/0262469 A1 | 8/2019 | Brinker et al. |
| 2019/0330373 A1 | 10/2019 | Stephan |
| 2020/0009264 A1 | 1/2020 | Brinker et al. |
| 2020/0197536 A1 | 6/2020 | Brinker et al. |
| 2020/0375912 A1 | 12/2020 | Serda et al. |
| 2020/0405650 A1 | 12/2020 | Noureddine et al. |
| 2021/0030675 A1 | 2/2021 | Brinker et al. |
| 2021/0315822 A1 | 10/2021 | Guo et al. |
| 2022/0033767 A1 * | 2/2022 | Guo ............ C12N 5/0006 |
| 2022/0151924 A1 | 5/2022 | Brinker et al. |

FOREIGN PATENT DOCUMENTS

| | | |
|---|---|---|
| WO | WO-9747296 A2 | 12/1997 |
| WO | WO-0076556 A2 | 12/2000 |
| WO | WO-02066506 A2 | 8/2002 |
| WO | WO-03055469 A1 | 7/2003 |
| WO | WO-2004096140 A2 | 11/2004 |
| WO | WO-2005009602 A2 | 3/2005 |
| WO | WO-2005084710 A2 | 9/2005 |
| WO | WO-2007140618 A1 | 12/2007 |
| WO | WO-2009051837 A2 | 4/2009 |
| WO | WO-2010035304 A2 | 4/2010 |
| WO | WO-2010048572 A1 | 4/2010 |
| WO | WO-2010078569 A2 | 7/2010 |
| WO | WO-2011116219 A1 | 9/2011 |
| WO | WO-2011116226 A2 | 9/2011 |
| WO | WO-2011150264 A2 | 12/2011 |
| WO | WO-2012149376 A2 | 11/2012 |
| WO | WO-2013012891 A1 | 1/2013 |
| WO | WO-2013056132 A2 | 4/2013 |
| WO | WO-2013082612 A1 | 6/2013 |
| WO | WO-2013103614 A1 | 7/2013 |
| WO | WO-2014093635 A1 | 6/2014 |
| WO | WO-2014165608 A1 | 10/2014 |
| WO | WO-2014165617 A1 | 10/2014 |
| WO | WO-2015042268 A1 | 3/2015 |
| WO | WO-2015042279 A1 | 3/2015 |
| WO | WO-2015095340 A1 | 6/2015 |
| WO | WO-2015130584 A2 | 9/2015 |
| WO | WO-2016145031 A1 | 9/2016 |
| WO | WO-2016145335 A1 | 9/2016 |
| WO | 2017013250 | 1/2017 |
| WO | WO-2017041032 A1 | 3/2017 |
| WO | WO-2017041033 A1 | 3/2017 |
| WO | WO-2017120504 A1 | 7/2017 |
| WO | WO-2018000043 A1 * | 1/2018 |
| WO | WO-2018160865 | 9/2018 |
| WO | WO-2018187287 A1 | 10/2018 |
| WO | WO-2019028387 A1 | 2/2019 |
| WO | WO-2019169152 A1 | 9/2019 |
| WO | WO-2020028342 A1 | 2/2020 |
| WO | WO-2020068798 A1 | 4/2020 |
| WO | WO-2020068806 A1 | 4/2020 |

(56) References Cited

FOREIGN PATENT DOCUMENTS

| WO | WO-2020176716 A1 | 9/2020 |
|---|---|---|
| WO | 2023147596 | 8/2023 |
| WO | WO-2024182425 A1 | 9/2024 |

OTHER PUBLICATIONS

Rocco et al. 2018. "Metal-organic frameworks for cell and virus biology: a perspective". ACS nano, 12(1), 13-23 (Year: 2018).*

Zhu, Wei et al. "SupraCells: Living Mammalian Cells Protected within Functional Modular Nanoparticle-Based Exoskeletons." Advanced materials. 2019; 31(25): e1900545. doi: 10.1002/adma. 201900545. (Year: 2019).*

"U.S. Appl. No. 16/635,246, Non Final Office Action mailed Apr. 10, 2023", 21 pgs.

"U.S. Appl. No. 16/500,349, Final Office Action mailed May 3, 2023", 17 pgs.

"International Application Serial No. PCT US2023 061675, International Search Report mailed May 24, 2023", 6 pgs.

"International Application Serial No. PCT US2023 061675, Written Opinion mailed May 24, 2023", 6 pgs.

"U.S. Appl. No. 16/976,651, Response filed Jun. 28, 2023 to Non Final Office Action mailed Feb. 28, 2023", 11 pgs.

"U.S. Appl. No. 16/635,246, Response filed Jul. 10, 2023 to Non Final Office Action mailed Apr. 10, 2023", 9 pgs.

"U.S. Appl. No. 16/635,246, Final Office Action mailed Jul. 25, 2023", 23 pgs.

"U.S. Appl. No. 16/976,651, Final Office Action mailed Jul. 27, 2023", 25 pgs.

Brinker, C J, "2021-023—Triplex Nanoparticles for Targeted Gene Delivery", UNM Rainforest Innovations, [Online]. Retrieved from the Internet: https: unm.flintbox.com technologies c52813ba-2361-47e9-baca-e6f39303b3fd, (Apr. 28, 2021), 1-2.

Noureddine, A, "Engineering of monosized lipid-coated mesoporous silica nanoparticles for CRISPR delivery", Acta Biomaterialia, Epub. vol. 114, (Jul. 21, 2020), 358-368.

"U.S. Appl. No. 10/100,108, Non Final Office Action mailed Jan. 22, 2004", 8 pgs.

"U.S. Appl. No. 10/100,108, Notice of Allowance mailed Jul. 13, 2004", 10 pgs.

"U.S. Appl. No. 10/100,108, Response filed Apr. 21, 2004 to Non Final Office Action mailed Jan. 22, 2004", 9 pgs.

"U.S. Appl. No. 10/163,425, Advisory Action mailed Jul. 2, 2004".

"U.S. Appl. No. 10/163,425, Examiner Interview Summary filed Mar. 29, 2005", 9 pgs.

"U.S. Appl. No. 10/163,425, Final Office Action mailed Mar. 31, 2004", 8 pgs.

"U.S. Appl. No. 10/163,425, Non Final Office Action mailed Aug. 1, 2003", 10 pgs.

"U.S. Appl. No. 10/163,425, Non Final Office Action mailed Sep. 22, 2004", 6 pgs.

"U.S. Appl. No. 10/163,425, Notice of Allowance mailed Feb. 10, 2005", 8 pgs.

"U.S. Appl. No. 10/163,425, Response filed Jan. 2, 2004 to Non Final Office Action mailed Aug. 1, 2003", 13 pgs.

"U.S. Appl. No. 10/163,425, Response filed May 28, 2004 to Final Office Action mailed Mar. 31, 2004", 15 pgs.

"U.S. Appl. No. 10/163,425, Response filed Jul. 23, 2004 to Advisory Action mailed Jul. 2, 2004", 15 pgs.

"U.S. Appl. No. 10/163,425, Response filed Dec. 22, 2004 to Non Final Office Action mailed Sep. 22, 2004", 11 pgs.

"U.S. Appl. No. 10/373,565, Notice of Allowance mailed Sep. 11, 2007", 4 pgs.

"U.S. Appl. No. 12/903,577, Advisory Action mailed Mar. 20, 2012", 3 pgs.

"U.S. Appl. No. 12/903,577, Advisory Action mailed Jun. 7, 2017", 2 pgs.

"U.S. Appl. No. 12/903,577, Final Office Action mailed May 8, 2015", 19 pgs.

"U.S. Appl. No. 12/903,577, Non Final Office Action malled Jun. 3, 2014", 16 pgs.

"U.S. Appl. No. 12/903,577, Final Office Action mailed Nov. 30, 2011", 19 pgs.

"U.S. Appl. No. 12/903,577, Non Final Office Action mailed Jun. 30, 2011", 13 pgs.

"U.S. Appl. No. 12/903,577, Non Final Office Action mailed Oct. 25, 2017", 16 pgs.

"U.S. Appl. No. 12/903,577, Notice of Non-Compliant Amendment mailed Feb. 4, 2015" 5 pgs.

"U.S. Appl. No. 12/903,577, Response filed Jan. 20, 2016 to Final Office Action mailed May 8, 2015", 7 pgs.

"U.S. Appl. No. 12/903,577, Response filed Feb. 26, 2015 to Notice of Non-Compliant Amendment mailed Feb. 4, 2015", 5 pgs.

"U.S. Appl. No. 12/903,577, Response filed Mar. 9, 2012 to Final Office Action mailed Nov. 30, 2011", 22 pgs.

"U.S. Appl. No. 12/903,577, Response filed Jun. 1, 2011 to Restriction Requirement mailed May 13, 2011", 2 pgs.

"U.S. Appl. No. 12/903,577, Response filed Jul. 12, 2017 to Advisory Action mailed Jan. 7, 2017", 7 pgs.

"U.S. Appl. No. 12/903,577, Response filed Sep. 30, 2011 to Non Final Office Action mailed Jun. 30, 2011", 9 pgs.

"U.S. Appl. No. 12/903,577, Response filed Dec. 3, 2014 to Non Final Office Action mailed Jun. 3, 2014", 15 pgs.

"U.S. Appl. No. 12/903,577, Restriction Requirement mailed May 13, 2011", 10 pgs.

"U.S. Appl. No. 13/143,164, 312 Amendment filed Mar. 27, 2014", 5 pgs.

"U.S. Appl. No. 13/143,164, Final Office Action mailed Jun. 26, 2013", 14 pgs.

"U.S. Appl. No. 13/143,164, Non Final Office Action mailed Jan. 11, 2013", 12 pgs.

"U.S. Appl. No. 13/143,164, Notice of Allowance mailed Jan. 13, 2014", 7 pgs.

"U.S. Appl. No. 13/143,164, Response filed Apr. 10, 2013 to Non Final Office Action mailed Jan. 11, 2013", 13 pgs.

"U.S. Appl. No. 13/143,164, Response filed Nov. 7, 2012 to Restriction Requirement mailed Oct. 10, 2012", 4 pgs.

"U.S. Appl. No. 13/143,164, Response filed Nov. 26, 2013 to Final Office Action mailed Jun. 26, 2013", 18 pgs.

"U.S. Appl. No. 13/143,164, Restriction Requirement mailed Oct. 10, 2012", 11 pgs.

"U.S. Appl. No. 14/113,371, 312 Amendment filed Dec. 21, 2016", 4 pgs.

"U.S. Appl. No. 14/113,371, Amendment filed Sep. 23, 2016", 16 pgs.

"U.S. Appl. No. 14/113,371, Examiner Interview Summary mailed Mar. 25, 2016", 1 pg.

"U.S. Appl. No. 14/113,371, Final Office Action mailed Feb. 1, 2016", 15 pgs.

"U.S. Appl. No. 14/113,371, Final Office Action mailed Mar. 25, 2016", 13 pgs.

"U.S. Appl. No. 14/113,371, Non Final Office Action mailed Jul. 13, 2015", 14 pgs.

"U.S. Appl. No. 14/113,371, Non Final Office Action mailed Dec. 17, 2014", 15 pgs.

"U.S. Appl. No. 14/113,371, Notice of Allowability mailed Jan. 31, 2017", 4 pgs.

"U.S. Appl. No. 14/113,371, Notice of Allowance mailed Oct. 11, 2016", 9 pgs.

"U.S. Appl. No. 14/113,371, Preliminary Amendment filed Oct. 22, 2013", 14 pgs.

"U.S. Appl. No. 14/113,371, Response filed Apr. 16, 2015 to Non Final Office Action mailed Dec. 17, 2014", 23 pgs.

"U.S. Appl. No. 14/113,371, Response filed Aug. 25, 2016 to Final Office Action mailed Mar. 25, 2016", 17 pgs.

"U.S. Appl. No. 14/113,371, Response filed Oct. 17, 2014 to Restriction Requirement mailed Aug. 18, 2014", 19 pgs.

"U.S. Appl. No. 14/113,371, Response filed Nov. 4, 2015 to Non Final Office Action mailed Jul. 13, 2015", 25 pgs.

"U.S. Appl. No. 14/113,371, Response filed Sep. 26, 2016 to Final Office Action mailed Mar. 25, 2016", 16 pgs.

(56) References Cited

OTHER PUBLICATIONS

"U.S. Appl. No. 14/113,371, Restriction Requirement mailed Aug. 18, 2014", 12 pgs.
"U.S. Appl. No. 14/253,030, Advisory Action mailed Apr. 11, 2018", 25 pgs.
"U.S. Appl. No. 14/253,030, Advisory Action mailed Sep. 5, 2017", 22 pgs.
"U.S. Appl. No. 14/253,030, Advisory Action mailed Sep. 9, 2016", 16 pgs.
"U.S. Appl. No. 14/253,030, Declaration under 37 C.F.R 1.132 filed Mar. 27, 2018", 4 pgs.
"U.S. Appl. No. 14/253,030, Final Office Action mailed May 11, 2016", 15 pgs.
"U.S. Appl. No. 14/253,030, Final Office Action mailed Jun. 9, 2017", 19 pgs.
"U.S. Appl. No. 14/253,030, Final Office Action mailed Dec. 1, 2017", 21 pgs.
"U.S. Appl. No. 14/253,030, Non Final Office Action mailed Dec. 9, 2016", 19 pgs.
"U.S. Appl. No. 14/253,030, Non Final Office Action mailed Dec. 10, 2015", 14 pgs.
"U.S. Appl. No. 14/253,030, Preliminary Amendment filed Jul. 1, 2015", 8 pgs.
"U.S. Appl. No. 14/253,030, Preliminary Amendment filed Dec. 9, 2014", 3 pgs.
"U.S. Appl. No. 14/253,030, Response filed Mar. 10, 2016 to Non Final Office Action mailed Dec. 10, 2015", 11 pgs.
"U.S. Appl. No. 14/253,030, Response filed Aug. 11, 2016 to Final Office Action mailed May 11, 2016", 9 pgs.
"U.S. Appl. No. 14/253,030, Response filed Oct. 10, 2017 to Advisory Action mailed Sep. 5, 2017", 12 pgs.
"U.S. Appl. No. 14/253,030, Response filed Oct. 11, 2016 to Advisory Action mailed Sep. 9, 2016", 9 pgs.
"U.S. Appl. No. 14/253,030, Response filed Nov. 2, 2015 to Restriction Requirement mailed Oct. 6, 2015", 4 pgs.
"U.S. Appl. No. 14/253,030, Response filed Apr. 2, 2018 to Final Office Action mailed Dec. 1, 2017", 10 pgs.
"U.S. Appl. No. 14/253,030, Response filed May 9, 2017 to Non-Final Office ACtion mailed Dec. 9, 2016", 8 pgs.
"U.S. Appl. No. 14/253,030, Response filed Aug. 10, 2017 to Final Office Action mailed Jun. 9, 2017", 12 pgs.
"U.S. Appl. No. 14/253,030, Restriction Requirement mailed Sep. 17, 2015", 7 pgs.
"U.S. Appl. No. 14/253,030, Restriction Requirement mailed Oct. 6, 2015", 7 pgs.
"U.S. Appl. No. 14/253,030, Supplemental Declaration under 37 C.F.R. 1.132 filed Aug. 7, 2017", 2 pgs.
"U.S. Appl. No. 14/350,674, Non Final Office Action mailed Jun. 17, 2016", 19 pgs.
"U.S. Appl. No. 14/350,674, Preliminary Amendment filed Jun. 4, 2015", 12 pgs.
"U.S. Appl. No. 14/350,674, Response filed May 16, 2016 to Restriction Requirement mailed Mar. 14, 2016", 10 pgs.
"U.S. Appl. No. 14/350,674, Restriction Requirement mailed Mar. 14, 2016", 12 pgs.
"U.S. Appl. No. 14/369,741, Final Office Action mailed Apr. 19, 2017", 10 pgs.
"U.S. Appl. No. 14/369,741, Non Final Office Action mailed Aug. 22, 2016", 17 pgs.
"U.S. Appl. No. 14/369,741, Non Final Office Action mailed Nov. 23, 2015", 11 pgs.
"U.S. Appl. No. 14/369,741, Preliminary Amendment filed Jun. 26, 2014", 16 pgs.
"U.S. Appl. No. 14/369,741, Response filed Mar. 23, 2016 to Non Final Office Action mailed Nov. 23, 2015", 12 pgs.
"U.S. Appl. No. 14/369,741, Response filed Sep. 14, 2015 to Restriction Requirement mailed May 14, 2015", 13 pgs.
"U.S. Appl. No. 14/369,741, Response filed Dec. 22, 2016 to Non-Final Office Action mailed Aug. 22, 2016", 12 pgs.
"U.S. Appl. No. 14/369,741, Restriction Requirement mailed May 14, 2015", 12 pgs.
"U.S. Appl. No. 14/627,739, Non Final Office Action mailed Jan. 29, 2016", 4 pgs.
"U.S. Appl. No. 14/627,739, Notice of Allowance mailed Jul. 6, 2016", 6 pgs.
"U.S. Appl. No. 14/627,739, Preliminary Amendment filed Feb. 20, 2015", 5 pgs.
"U.S. Appl. No. 14/627,739, Response filed Apr. 15, 2016 to Non Final Office Action mailed Jan. 29, 2016", 6 pgs.
"U.S. Appl. No. 14/627,739, Response filed Nov. 5, 2015 to Restriction Requirement mailed Aug. 6, 2015", 7 pgs.
"U.S. Appl. No. 14/627,739, Restriction Requirement mailed Aug. 6, 2015", 5 pgs.
"U.S. Appl. No. 14/781,765, Advisory Action mailed Jan. 29, 2019", 4 pgs.
"U.S. Appl. No. 14/781,765, Final Office Action mailed Aug. 28, 2018", 9 pgs.
"U.S. Appl. No. 14/781,765, Non Final Office Action mailed Feb. 15, 2018", 9 pgs.
"U.S. Appl. No. 14/781,765, Non Final Office Action mailed Jul. 15, 2019", 7 pgs.
"U.S. Appl. No. 14/781,765, Response filed Jan. 21, 2019 to Final Office Action mailed Aug. 28, 2018", 7 pgs.
"U.S. Appl. No. 14/781,765, Response filed Jun. 15, 2018 to Non Final Office Action mailed Feb. 15, 2018", 6 pgs.
"U.S. Appl. No. 14/781,765, Response filed Jan. 24, 2018 to Restriction Requirement mailed Aug. 24, 2017", 4 pgs.
"U.S. Appl. No. 14/781,765, Response filed Jan. 28, 2019 to Non-Final Office Action mailed Aug. 28, 2018", 7 pgs.
"U.S. Appl. No. 14/781,765, Restriction Requirement mailed Aug. 24, 2017", 6 pgs.
"U.S. Appl. No. 14/781,817, Preliminary Amendment filed Jan. 17, 2017", 5 pgs.
"U.S. Appl. No. 14/781,817, Restriction Requirement mailed Oct. 31, 2018", 9 pgs.
"U.S. Appl. No. 14/781,817, Supplemental Preliminary Amendment field Aug. 8, 2017", 9 pgs.
"U.S. Appl. No. 14/781,817, Supplemental Preliminary Amendment filed Jun. 27, 2017", 9 pgs.
"U.S. Appl. No. 14/797,487, Non Final Office Action mailed Jun. 14, 2017", 7 pgs.
"U.S. Appl. No. 14/797,487, Preliminary Amendment filed Jul. 24, 2015", 10 pgs.
"U.S. Appl. No. 14/797,487, Response filed Mar. 3, 2017 to Restriction Requirement mailed Jan. 3, 2017", 10 pgs.
"U.S. Appl. No. 14/797,487, Restriction Requirement mailed Jan. 3, 2017", 12 pgs.
"U.S. Appl. No. 14/970,998, Final Office Action mailed Sep. 27, 2017", 13 pgs.
"U.S. Appl. No. 14/970,998, Non Final Office Action mailed Apr. 6, 2017", 17 pgs.
"U.S. Appl. No. 14/970,998, Notice of Allowance mailed Mar. 16, 2018", 9 pgs.
"U.S. Appl. No. 14/970,998, Preliminary Amendment filed Dec. 16, 2015", 3 pgs.
"U.S. Appl. No. 14/970,998, Preliminary Amendment filed Dec. 28, 2015", 13 pgs.
"U.S. Appl. No. 14/970,998, Response filed Feb. 27, 2018 to Final Office Action mailed Sep. 27, 2017", 8 pgs.
"U.S. Appl. No. 14/970,998, Response filed Mar. 17, 2017 to Restriction Requirement mailed Jan. 19, 2017", 8 pgs.
"U.S. Appl. No. 14/970,998, Response filed Aug. 7, 2017 to Non-Final Office Action mailed Apr. 6, 2017", 13 pgs.
"U.S. Appl. No. 14/970,998, Restriction Requirement mailed Jan. 19, 2017", 8 pgs.
"U.S. Appl. No. 15/023,093 Response filed Feb. 3, 2017 to Restriction Requirement mailed Nov. 3, 2016", 12 pgs.
"U.S. Appl. No. 15/023,093, Non Final Office Action mailed Apr. 11, 2017", 12 pgs.
"U.S. Appl. No. 15/023,093, Preliminary Amendment filed Mar. 18, 2016", 3 pgs.

(56) References Cited

OTHER PUBLICATIONS

"U.S. Appl. No. 15/023,093, Restriction Requirement mailed Nov. 3, 2016", 10 pgs.

"U.S. Appl. No. 15/023,110, Corrected Notice of Allowance mailed Sep. 5, 2017", 8 pgs.

"U.S. Appl. No. 15/023,110, Non Final Office Action mailed Feb. 24, 2017", 10 pgs.

"U.S. Appl. No. 15/023,110, Notice of Allowance mailed Aug. 21, 2017", 11 pgs.

"U.S. Appl. No. 15/023,110, Preliminary Amendment filed Mar. 18, 2016", 3 pgs.

"U.S. Appl. No. 15/023,110, Preliminary Amendment filed Jul. 5, 2016", 7 pgs.

"U.S. Appl. No. 15/023,110, Response filed Jul. 24, 2017 to Non-Final Office Action mailed Feb. 24, 2017", 10 pgs.

"U.S. Appl. No. 15/380,962, Non Final Office Action mailed Aug. 2, 2017", 20 pgs.

"U.S. Appl. No. 15/380,962, Preliminary Amendment filed Dec. 15, 2016", 3 pgs.

"U.S. Appl. No. 15/380,962, Response filed Jul. 19, 2017 to Restriction Requirement mailed May 18, 2017", 9 pgs.

"U.S. Appl. No. 15/380,962, Restriction Requirement mailed May 18, 2017", 9 pgs.

"U.S. Appl. No. 15/474,800, Final Office Action mailed Mar. 8, 2019", 9 pgs.

"U.S. Appl. No. 15/474,800, Non Final Office Action mailed Oct. 18, 2018", 8 pgs.

"U.S. Appl. No. 15/474,800, Preliminary Amendment filed Jul. 19, 2017", 12 pgs.

"U.S. Appl. No. 15/474,800, Preliminary Amendment filed Oct. 10, 2017", 4 pgs.

"U.S. Appl. No. 15/474,800, Response filed Jan. 18, 2019 t Non-Final Office Action mailed Oct. 18, 2019", 11 pg.

"U.S. Appl. No. 15/474,800, Response filed Aug. 13, 2018 to Restriction Requirement mailed Mar. 12, 2018", 11 pgs.

"U.S. Appl. No. 15/474,800, Restriction Requirement mailed Mar. 12, 2018", 6 pgs.

"U.S. Appl. No. 15/474,810, Final Office Action mailed Mar. 8, 2019", 10 pgs.

"U.S. Appl. No. 15/474,810, Non Final Office Action mailed Sep. 20, 2018", 12 pgs.

"U.S. Appl. No. 15/474,810, Preliminary Amendment filed Jul. 18, 2017", 8 pgs.

"U.S. Appl. No. 15/474,810, Response filed Jan. 18, 2019 to Non-Final Office Action mailed Sep. 20, 2018", 8 pgs.

"U.S. Appl. No. 15/474,810, Response filed Aug. 7, 2018 to Restriction Requirement mailed Mar. 7, 2018", 8 pgs.

"U.S. Appl. No. 15/474,810, Restriction Requirement mailed Mar. 7, 2018", 8 pgs.

"U.S. Appl. No. 15/474,810. Supplemental Preliminary Amendment filed Oct. 30, 2017", 4 pgs.

"U.S. Appl. No. 15/557,000, Preliminary Amendment filed Sep. 8, 2017", 7 pgs.

"U.S. Appl. No. 15/557,000, Restriction Requirement mailed Mar. 11, 2019", 9 pgs.

"U.S. Appl. No. 15/557,368, Preliminary Amendment filed Sep. 11, 2017", 8 pgs.

"U.S. Appl. No. 15/557,368, Restriction Requirement mailed Feb. 15, 2019", 8 pgs.

"U.S. Appl. No. 15/757,254, Preliminary Amendment filed Mar. 2, 2018", 11 pgs.

"U.S. Appl. No. 15/757,254, Restriction Requirement mailed Sep. 16, 2019", 11 pgs.

"U.S. Appl. No. 15/757,269, Examiner Interview Summary mailed Jun. 25, 2019", 5 pgs.

"U.S. Appl. No. 15/757,269, Final Office Action mailed Oct. 25, 2019", 20 pgs.

"U.S. Appl. No. 15/757,269, Non Final Office Action mailed Apr. 12, 2019", 30 pgs.

"U.S. Appl. No. 15/757,269, Non Final Office Action mailed Dec. 4, 2018", 19 pgs.

"U.S. Appl. No. 15/757,269, Response filed Oct. 14, 2019 to Non-Final Office Action mailed Apr. 12, 2019", 10 pgs.

"U.S. Appl. No. 15/757,269, Response filed Mar. 28, 2019 to Non-Final Office Action mailed Dec. 4, 2018", 10 pgs.

"U.S. Appl. No. 16/025,557, Non Final Office Action mailed Feb. 6, 2020", 8 pgs.

"U.S. Appl. No. 16/025,557, Preliminary Amendment filed Jul. 2, 2018", 10 pgs.

"U.S. Appl. No. 16/068,235, Examiner Interview Summary mailed Apr. 5, 2021", 5 pgs.

"U.S. Appl. No. 16/068,235, Non Final Office Action mailed May 13, 2020", 19 pgs.

"U.S. Appl. No. 16/068,235, Non Final Office Action mailed Jun. 15, 2021", 27 pgs.

"U.S. Appl. No. 16/068,235, Non Final Office Action mailed Aug. 25, 2020", 28 pgs.

"U.S. Appl. No. 16/068,235, Notice of Non-Compliant Amendment mailed Apr. 6, 2021", 2 pgs.

"U.S. Appl. No. 16/068,235, Preliminary Amendment filed Jul. 5, 2018", 10 pgs.

"U.S. Appl. No. 16/068,235, Response filed Feb. 25, 2021 to Non Final Office Action mailed Aug. 25, 2020", 13 pgs.

"U.S. Appl. No. 16/068,235, Response filed May 1, 2020 to Restriction Requirement mailed Feb. 28, 2020", 9 pgs.

"U.S. Appl. No. 16/068,235, Response filed Jun. 7, 2021 to Notice of Non-Compliant Amendment mailed Apr. 6, 2021", 1 pg.

"U.S. Appl. No. 16/068,235, Response filed Aug. 13, 2020 to Non Final Office Action mailed May 13, 2020", 11 pgs.

"U.S. Appl. No. 16/068,235, Response filed Nov. 9, 2021 to Non Final Office Action mailed Jun. 15, 2021", 12 pgs.

"U.S. Appl. No. 16/068,235, Restriction Requirement mailed Feb. 28, 2020", 10 pgs.

"U.S. Appl. No. 16/068,235, Supplemental Preliminary Amendment filed Feb. 17, 2022", 11 pgs.

"U.S. Appl. No. 16/490,280, Advisory Action mailed Sep. 21, 2021", 3 pgs.

"U.S. Appl. No. 16/490,280, Final Office Action mailed May 13, 2021", 9 pgs.

"U.S. Appl. No. 16/490,280, Non Final Office Action mailed Nov. 13, 2020", 8 pgs.

"U.S. Appl. No. 16/490,280, Notice of Allowability mailed Feb. 9, 2022", 3 pgs.

"U.S. Appl. No. 16/490,280, Notice of Allowance mailed Jan. 28, 2022", 9 pgs.

"U.S. Appl. No. 16/490,280, Preliminary Amendment filed Aug. 30, 2019", 7 pgs.

"U.S. Appl. No. 16/490,280, Response filed Apr. 13, 2021 to Non Final Office Action mailed Nov. 13, 2020", 7 pgs.

"U.S. Appl. No. 16/490,280, Response filed Sep. 13, 2021 to Final Office Action mailed May 13, 2021", 9 pgs.

"U.S. Appl. No. 16/490,280, Response filed Sep. 28, 2020 to Restriction Requirement mailed Jul. 27, 2020", 7 pgs.

"U.S. Appl. No. 16/490,280, Restriction Requirement mailed Jul. 27, 2020", 8 pgs.

"U.S. Appl. No. 16/500,349, Preliminary Amendment filed Oct. 2, 2019", 7 pgs.

"U.S. Appl. No. 16/635,246, Response filed Mar. 9, 2022 to Restriction Requirement mailed Feb. 17, 2022", 7 pgs.

"U.S. Appl. No. 16/635,246, Restriction Requirement mailed Feb. 17, 2022", 11 pgs.

"U.S. Appl. No. 16/635,246. Preliminary Amendment filed Jan. 30, 2020", 7 pgs.

"U.S. Appl. No. 16/828,137, Non Final Office Action mailed Jun. 15, 2021", 29 pgs.

"U.S. Appl. No. 16/828,137, Preliminary Amendment filed Mar. 24, 2020", 6 pgs.

"U.S. Appl. No. 16/828,137, Response filed Jun. 2, 2021 to Restriction Requirement mailed Apr. 2, 2021", 6 pgs.

"U.S. Appl. No. 16/828,137, Restriction Requirement mailed Apr. 2, 2021", 13 pgs.

(56) References Cited

OTHER PUBLICATIONS

"U.S. Appl. No. 16/976,651, Preliminary Amendment filed Aug. 28, 2020", 7 pgs.
"U.S. Appl. No. 16/976,651, Restriction Requirement mailed Mar. 9, 2022", 8 pgs.
"U.S. Appl. No. 17/264,452, Preliminary Amendment Filed Jan. 29, 2021", 6 pgs.
"U.S. Appl. No. 17/277,260, Preliminary Amendment filed Mar. 17, 2021", 7 pgs.
"U.S. Appl. No. 17/434,363, Preliminary Amendment filed Aug. 26, 2021", 7 pgs.
"U.S. Appl. No. 14/781,765, Preliminary Amendment filed Jul. 20, 2016", 6 pgs.
"U.S. Appl. No. 15/023,093, Preliminary Amendment filed Jun. 23, 2016", 11 pgs.
"U.S. Appl. No. 15/858,923, Preliminary Amendment filed Dec. 29, 2017", 7 pgs.
"Australian Application Serial No. 2012249474, First Examiner Report mailed Jul. 20, 2016", 4 pgs.
"Australian Application Serial No. 2012323937, First Examiner Report mailed Oct. 7, 2016", 5 pgs.
"Chinese Application Serial No. 201280031496.8, Decision on Rejection mailed Jun. 7, 2016", (English Translation), 9 pgs.
"Chinese Application Serial No. 201280061866.2, Office Action mailed Mar. 17, 2016", with English translation of claims, 23 pgs.
"European Application Serial No. 12776480.1, Extended European Search Report mailed Oct. 9, 2014", 8 pgs.
"European Application Serial No. 12776480.1, Response filed May 5, 2015 to Office Action mailed Oct. 28, 2014", 10 pgs.
"European Application Serial No. 12840155.1, Communication Pursuant to Article 94(3) EPC mailed Nov. 24, 2016", 5 pgs.
"European Application Serial No. 12840155.1, Extended European Search Report mailed May 28, 2015", 6 pgs.
"European Application Serial No. 14778464.9, Amendment filed Oct. 28, 2015", 18 pgs.
"European Application Serial No. 14778464.9, Extended European Search Report mailed Oct. 21, 2016", 8 pgs.
"European Application Serial No. 14778464.9, Response filed May 13, 2016 to Communication pursuant to Rules 161(2) and 162 EPC mailed Nov. 20, 2015", 17 pgs.
"European Application Serial No. 14779421.8, Extended European Search Report mailed Oct. 13, 2016", 11 pgs.
"European Application Serial No. 14779421.8, Response filed May 12, 2016 to Communication pursuant to Rules 161(2) and 162 EPC mailed Nov. 13, 2015", 21 pgs.
"European Application Serial No. 14845415.0, Response filed Nov. 2, 2016 to Communication pursuant to Rules 161(1) and 162 EPC mailed May 2, 2016", 9 pgs.
"European Application Serial No. 14846653.5, Extended European Search Report mailed Apr. 26, 2017", 9 pgs.
"European Application Serial No. 14846653.5, Response filed Nov. 2, 2016 to Communication pursuant to Rules 161(1) and 162 EPC mailed May 2, 2016", 37 pgs.
"International Application Serial No. PCT/US2014/056342, International Preliminary Report on Patentability mailed Mar. 22, 2016", 9 pgs.
"International Application Serial No. PCT/US2010/020096, International Preliminary Report on Patentability mailed Jul. 14, 2011", 5 pgs.
"International Application Serial No. PCT/US2010/020096, International Search Report mailed Sep. 17, 2010", 3 pgs.
"International Application Serial No. PCT/US2010/020096, Written Opinion mailed Sep. 17, 2010", 3 pgs.
"International Application Serial No. PCT/US2012/035529, International Preliminary Report on Patentability mailed Nov. 7, 2013", 8 pgs.
"International Application Serial No. PCT/US2012/035529, International Search Report mailed Oct. 23, 2012", 5 pgs.
"International Application Serial No. PCT/US2012/035529, Written Opinion mailed Oct. 23, 2012", 8 pgs.
"International Application Serial No. PCT/US2012/060072, International Preliminary Report on Patentability mailed Apr. 15, 2014", 10 pgs.
"International Application Serial No. PCT/US2012/060072, International Search Report mailed Mar. 28, 2013", 6 pgs.
"International Application Serial No. PCT/US2012/060072, Written Opinion mailed Mar. 28, 2013", 9 pgs.
"International Application Serial No. PCT/US2012/072297, International Preliminary Report on Patentability mailed Jul. 10, 2014", 13 pgs.
"International Application Serial No. PCT/US2012/072297, International Search Report mailed Jun. 2, 2013", 6 pgs.
"International Application Serial No. PCT/US2012/072297, Written Opinion mailed Jun. 2, 2013", 11 pgs.
"International Application Serial No. PCT/US2014/032702, International Preliminary Report on Patentability mailed Oct. 6, 2015", 10 pgs.
"International Application Serial No. PCT/US2014/032702, International Search Report mailed Aug. 26, 2014", 5 pgs.
"International Application Serial No. PCT/US2014/032702, Written Opinion mailed Aug. 26, 2014", 9 pgs.
"International Application Serial No. PCT/US2014/032711, International Preliminary Report on Patentability Oct. 6, 2015", 10 pgs.
"International Application Serial No. PCT/US2014/032711, International Search Report mailed Aug. 5, 2014", 5 pgs.
"International Application Serial No. PCT/US2014/032711, Written Opinion mailed Aug. 5, 2014", 9 pgs.
"International Application Serial No. PCT/US2014/056312, International Preliminary Report on Patentability mailed Mar. 31, 2016", 10 pgs.
"International Application Serial No. PCT/US2014/056312, International Search Report mailed Dec. 24, 2014", 5 pgs.
"International Application Serial No. PCT/US2014/056312, Written Opinion mailed Dec. 24, 2014", 8 pgs.
"International Application Serial No. PCT/US2014/056342, International Search Report mailed Dec. 23, 2014", 4 pgs.
"International Application Serial No. PCT/US2014/056342, Written Opinion mailed Dec. 23, 2014", 8 pgs.
"International Application Serial No. PCT/US2015/053244, International Preliminary Report on Patentability mailed Apr. 13, 2017", 10 pgs.
"International Application Serial No. PCT/US2015/053244, International Search Report mailed Feb. 4, 2016", 5 pgs.
"International Application Serial No. PCT/US2015/053244, Written Opinion mailed Feb. 4, 2016", 8 pgs.
"International Application Serial No. PCT/US2016/021490, International Preliminary Report on Patentability mailed Sep. 21, 2017", 7 pgs.
"International Application Serial No. PCT/US2016/021490, International Search Report mailed Jun. 30, 2016", 4 pgs.
"International Application Serial No. PCT/US2016/021490, Written Opinion mailed Jun. 30, 2016", 5 pgs.
"International Application Serial No. PCT/US2016/022056, International Preliminary Report on Patentability mailed Sep. 21, 2017", 7 pgs.
"International Application Serial No. PCT/US2016/022056, International Search Report mailed Jul. 7, 2016", 4 pgs.
"International Application Serial No. PCT/US2016/022056, Written Opinion mailed Jul. 7, 2016", 5 pgs.
"International Application Serial No. PCT/US2016/050259, International Preliminary Report on Patentability mailed Mar. 15, 2018", 10 pgs.
"International Application Serial No. PCT/US2016/050259, International Search Report mailed Dec. 15, 2016", 4 pgs.
"International Application Serial No. PCT/US2016/050259, Written Opinion mailed Dec. 15, 2016", 8 pgs.
"International Application Serial No. PCT/US2016/050260, International Preliminary Report on Patentability mailed Mar. 15, 2018", 8 pgs.
"International Application Serial No. PCT/US2016/050260, International Search Report mailed Dec. 22, 2016", 3 pgs.
"International Application Serial No. PCT/US2016/050260, Written Opinion mailed Dec. 22, 2016", 6 pgs.

(56) References Cited

OTHER PUBLICATIONS

"International Application Serial No. PCT/US2017/012583, International Preliminary Report on Patentability mailed Jul. 19, 2018", 7 pgs.
"International Application Serial No. PCT/US2017/012583, International Search Report mailed Apr. 20, 2017", 3 pgs.
"International Application Serial No. PCT/US2017/012583, Written Opinion mailed Apr. 20, 2017", 5 pgs.
"International Application Serial No. PCT/US2018/020496, International Preliminary Report on Patentability mailed Sep. 12, 2019", 6 pgs.
"International Application Serial No. PCT/US2018/020496, International Search Report mailed Jun. 14, 2018", 4 pgs.
"International Application Serial No. PCT/US2018/020496, Written Opinion mailed Jun. 14, 2018", 4 pgs.
"International Application Serial No. PCT/US2018/025830, International Preliminary Report on Patentability mailed Oct. 17, 2019", 9 pgs.
"International Application Serial No. PCT/US2018/025830, International Search Report mailed Aug. 2, 2018", 4 pgs.
"International Application Serial No. PCT/US2018/025830, Written Opinion mailed Aug. 2, 2018", 7 pgs.
"International Application Serial No. PCT/US2018/045218, International Preliminary Report on Patentability mailed Feb. 13, 2020", 7 pgs.
"International Application Serial No. PCT/US2018/045218, International Search Report mailed Nov. 29, 2018", 3 pgs.
"International Application Serial No. PCT/US2018/045218, Written Opinion mailed Nov. 29, 2018", 5 pgs.
"International Application Serial No. PCT/US2019/020084, International Preliminary Report on Patentability mailed Sep. 10, 2020", 7 pgs.
"International Application Serial No. PCT/US2019/020084, International Search Report mailed Jun. 6, 2019", 3 pgs.
"International Application Serial No. PCT/US2019/020084, Written Opinion mailed Jun. 6, 2019", 5 pgs.
"International Application Serial No. PCT/US2019/044107, International Preliminary Report on Patentability mailed Feb. 11, 2021", 6 pgs.
"International Application Serial No. PCT/US2019/044107, International Search Report mailed Nov. 14, 2019", 2 pgs.
"International Application Serial No. PCT/US2019/044107, Written Opinion mailed Nov. 14, 2019", 4 pgs.
"International Application Serial No. PCT/US2019/052658, International Preliminary Report on Patentability mailed Apr. 1, 2021", 6 pgs.
"International Application Serial No. PCT/US2019/052669, International Preliminary Report on Patentability mailed Apr. 1, 2021", 7 pgs.
"International Application Serial No. PCT/US2020/020066, International Preliminary Report on Patentability mailed Sep. 10, 2021", 6 pgs.
"International Application Serial No. PCT/US2020/020066, International Search Report mailed Jun. 25, 2020", 2 pgs.
"International Application Serial No. PCT/US2020/020066, Written Opinion mailed Jun. 25, 2020", 4 pgs.
"Israel Application Serial No. 232025, Office Action mailed May 1, 2016", 2 pgs.
"Japanese Application Serial No. 2014-508125, Office Action mailed Feb. 15, 2016", with English translation of claims, 9 pgs.
"Japanese Application Serial No. 2014-508125, Written Amendment filed Apr. 27, 2015", with English translation, 29 pgs.
"Japanese Application Serial No. 2014-508125,, Decision on Refusal mailed Dec. 26, 2016", with English translation, 2 pgs.
"Japanese Application Serial No. 2014-535948, Office Action mailed Jun. 27, 2016", with machine translation, 16 pgs.
"Mexican Application Serial No. MX/a/2014/004415, Office Action mailed Apr. 19, 2018", with machine translation, 6 pgs.
"New Zealand Application Serial No. 624962, First Examiner Report mailed Feb. 9, 2016", 3 pgs.
"Russian Application Serial No. 2014119428, Office Action mailed Apr. 21, 2017", With English Translation, 7 pgs.
"Singapore Application Serial No. 11201401499X, Office Action mailed Apr. 19, 2016", 11 pgs.
"Singapore Application Serial No. 11201401499X, Written Opinion mailed Oct. 5, 2015", 11 pgs.
Akazawa, Takashi, et al., "Development of a dendritic cell-targeting lipopeptide as an immunoadjuvant that inhibits tumor growth without inducing local inflammation", International Journal of Cancer, vol. 135, (2014), 2847-2856.
Ashley, et al., "(abstract) Development of a Virus-Like Particle that integrates Phage Display and Targeted delivery capabilities", MRS meeting, (2010), 1 pg.
Ashley, C E, et al., "Cell-Specific Delivery of Diverse Cargos by Bacteriophage MS2 Virus-like Particles", ACSNANO, 5(7), (2011), 1-26.
Ashley, C E, et al., "The targeted delivery of multicomponent cargos to cancer cells by nanoporous particle-supported lipid bilayers", Nature Materials, No. 5, vol. 10, (Apr. 17, 2011), 389-397.
Ashley, CE, et al., "Delivery of Small Interfering RNA by Peptide-Targeted Mesoporous Silica Nanoparticle-Supported Lipid Bilayers", ACS Nano, vol. 6, No. 3, (2012), 2174-2188.
Attard, George S, et al., "Liquid-crystalline phases as templates for the synthesis of mesoporous silica", Nature Publishing Group vol. 378, (Nov. 23, 1995), 3 pgs.
Aubin, R. A., et al., "Highly effective delivery of foreign DNA to adherent cells via polybrene/DMSO-assisted gene transfer", Methods Mol Biol., 62, (1997), 319-42.
Bao, et al., "Targeted Gene Therapy of Ovarian Cancer using an Ovarian-Specific Promoter", Gynecologic Oncology, 84, (2002), 228-34.
Beckett, D, et al., "Roles of Operator and Non-operator RNA Sequences in Bacteriophage R17 Capsid Assembly", J Mol Biol, 204, (1988), 939-947.
Benneti, GJ, et al., "A peripheral mononeuropathy in rat that produces disorders of pain sensation like those seen in man", Pain, (1988), 87-107.
Bennett, Gary, et al., "A peripheral mononeuropathy in rat that produces disorders of pain sensation like those seen in man.", Pain, 33, (1988), 87-107.
Beteck, Richard, "Chemical and biochemical modification of mesoporous silicon for in vivo analysis.", Master's thesis, University of Eastern Finland, (2013), 8-9.
Brinker, C Jeffrey, et al., "Evaporation-Induced Self-Assembly: Nanostructures Made Easy", Advanced Materials, 11(7), (May 1999), 579-585.
Buranda, T, et al., "Biomimetic Molecular Assemblies on Glass and Mesoporous Silica Microbeads for Biotechnology", Langmuir, 19, (2003), 1654-1663.
Butler, Kimberly, et al., "Protocells: Modular Mesoporous Silica Nanoparticle-Supported Lipid Bilayers for Drug Delivery", Small 12, No. 16, (2016), 2173-2185.
Caldeira, J C, et al., "Stability and assembly in vitro of bacteriophage PP7 virus-like particles", Journal of Nanobiotechnology, 5, (2007), 1-13.
Carnes, E C, et al., "Confinement-induced quorum sensing of individual *Staphylococcus aureus* bacteria", Nature Chemical Biology, 6, (2010), 1-12.
Carnes, Eric C., et al., "Targeted Nanoporous Particle-Supported Lipid Bilayers for Treatment of Childhood Leukemia", (Jun. 2011), 1 pg.
Carroll, N J, et al., "Microparticles with Bimodal Nanoporosity Derived by Microemulsion Templating", Langmuir 25(23), (2009), 13540-13544.
Cartier, et al., "Utilization of synthetic peptides containing nuclear localization signals for nonviral gene transfer systems", Gene Therapy, 9, (2002), 157-67.
Chackerian, B, et al., "Peptide Epitope Identification by Affinity Selection on Bacteriophage MS2 Virus-Like Particles", J Mol Biol; 409, (2011), 1-18.

(56) References Cited

OTHER PUBLICATIONS

Chacur, M, et al., "A new model of sciatic inflammatory neuritis (SIN): induction of unilateral and bilateral mechanical allodynia following acute unilateral peri-sciatic immune activation in rats", Pain, 94, (2001), 231-244.
Chantal, Pichon, et al., "Mannosylated and Histidylated LPR Technology for Vaccination with Tumor Antigen mRNA", <https://link.springer.com/content/pdf/10.1007%2F978-1-62703-260-5_16.pdf>, (2013), 247-274.
Cheng, WWK, et al., "Expression and purification of two anti-CD19 single chain Fv fragments for targeting of liposomes to CD19-expressing cells", Biochimica et Biophysica Acta, 1768, (2007), 21-29.
Citorik, R J, et al., "Sequence-specific antimicrobials using efficiently delivered RNA-guided nucleases", Nature biotechnology, (Sep. 21, 2014), 13 pgs.
Clemens, Daniel L., et al., "Targeted Intracellular Delivery of Antituberculosis Drugs to *Mycobacterium tuberculosis*-Infected Macrophages via Functionalized Mesoporous Silica Nanoparticles", Antimicrobial Agents and Chemotherapy, (Feb. 2012), 2535-2545.
Cokol, M, et al., "Finding nuclear localization signals", EMBO Reports, 1(5), (2000), 1-17.
Crombez, Laurence, et al., "Targeting cyclin B1 through peptide-based delivery of siRNA prevents tumour growth", Nucleic Acids Res., vol. 37, No. 14, (2009), 4559-4569.
Dengler, Ellen C, et al., "Improvement of spinal non-viral IL-10 gene delivery by D-mannose as a transgene adjuvant to control chronic neuropathic pain", Journal of Neuroinflammation, (2014), 1-21.
Dengler, Ellen C., et al., "Mesoporous silica-supported lipid bilayers (protocells) for DAN cargo delivery to the spinal cord", Journal of Controlled Release 168, (2013), 209-224.
Dubertret, B, et al., "In Vivo Imaging of Quantum Dots Encapsulated in Phospholipid Micelles", Science, vol. 298, (Nov. 29, 2002), 1759-1762.
Epler, et al., "Nanopourous-Supported Lipid Bilayer Nanocarriers for Treatment of Childhood Leukemia", Materials Research Society, Symposium LL: Biometic Engineering of Micro-and Nanoparticles; LL6.11, (2011), 32 pgs.
Epler, K, et al., "Delivery of Ricin Toxin A-Chain by Peptide-Targeted mesoporous Silica Nanoparticle Supported Lipid Bilayers.", Advanced Healthcare Materials, (2012), 348-353.
Fan, H, et al., "Rapid prototyping of patterned functional nanostructures", Nature, 405(6782), (May 4, 2000), 56-60.
Fang, Aiping, et al., "Template-Free Formation of Monodisperse Doughnut-Shaped Silica Microparitoles by Droplet-Based Microfluidics", Chem. Mater, (2011), 4660-4662 pgs.
Feng, Pingyun, et al., "Control of Pore Sizes in Mesoporous Silica Templated by Liquid Crystals in Block Copolymer-Cosurfactant-Water Systems", Langmuir, vol. 16, No. 12,, (Mar. 24, 2000), 7 pgs.
Fishkis, M, et al., "Abstracts: 'Self organization of short peptides and simple amphiphiles into membranes' and 'Encapsulation of polynucleotide/polypeptide systems by membranes', from Steps Towards the Formation of a Protocell: The Possible Role of Short Peptides", Orig Life Evol Biosph, vol. 37, (2007), 543-545.
Fishkis, Maya, "Steps Towards the Formation of a Protocell: The Possible Role of Short Peptides", Orig Live Evol Biosph 37, (2007), 537-553.
Gamal, M M, et al., "Skin delivery of oestradiol from lipid vesicles: importance of liposome structure", Int. J. Pharm., vol. 204, No. 1-2, (2000), 159-169.
Gariepy, et al., "Vectorial Delivery of Macromolecules Into Cells Using Peptide-Based Vehicles", Trends in Biotechnology vol. 19, (2001), 21-28.
Giacomo, Dacarro, et al., "Monolayers of Polyethilenimine on Flat Glass: A Versatile Platform for Cations Coordination and Nanoparticle Grafting in the Preparation of Antibacterial Surfaces", Dalton Trans. 41, 2456, (Jan. 5, 2012), 8 pgs.

Gordon, Alan N., et al., "Recurrent Epithelial Ovarian Carcinoma: A Randomized Phase III Study of Pegylated Liposomal Doxorubicin Versus Topotecan", Journal of Clinical Oncology, 19(14), (2001), 3312-3322.
Harvey, R C, et al., "Rearrangement of CRLF2 is associated with mutation of JAK kinases, alteration of IKZF1, Hispanic/Latino ethnicity, and a poor outcome in pediatric, B-progenitor acute lymphoblastic leukemia", Blood, 115(26), 5312-5321.
Hatakeyama, "A pH-sensitive fusogenic peptide facilitates endosomal escape and greatly enhances the gene silencing of siRNA-containing nanoparticles in vitro and in vivo", Journal of Controlled Release, 139(2), (Oct. 15, 2009), 127-132.
Hicks, Randall W, et al., "Nanoparticle Assembly of Mesoporous A100H (Boehmite)", Chemistry of Materials, vol. 15, No. 1, (Jan. 1, 2003), 78-82.
Hildebrand, et al., "Nanoscale control of silica morphology and three-dimensional structure during diatom cell wall formation", Mater. Res. Vol. 21, No. 10, (2006), 2689-2698.
Hooker, J M, et al., "Interior Surface Modification of Bacteriophage MS2", J Am Chem Soc, 126, (2004), 3718-3719.
Huo, Qisheng, et al., "Surfactant Control of Phases in the Synthesis of Mesoporous Silica-Based Materials", Chem. Mater. 1996, 8, (Feb. 15, 1996), 14 pgs.
Ikari, Kenichi, et al., "Structural Control of Mesoporous Silica Nanoparticles in a Binary Surfactant System", 5 pgs.
Iskandar, Ferry, et al., "Control of the morphology of nanostructured particles prepared by the spray drying of nanopartilce sol", Journal of Colloid and Interface Science 265, (2003), 296-303.
Israelachvili, J N, et al., "Physical principles of membrane organization", Quarterly Reviews of Biophysics, vol. 13(2),, (1980), 121-200.
Jain, P T, et al., "Enhancement of liposomal gene delivery in human breast cancer cells by dimethyl sulfoxide", (Mar. 1998), 609-611.
Jain, R. K, "Barriers to drug delivery in Solid Tumors", Scientific American,.271 (1), (Jul. 1994), 58-65.
Jewett, M C, et al., "Mimicking the *Escherichia coli* Cytoplasmic Environment Activates Long-Lived and Efficient Cell-Free Protein Synthesis", Wiley InterScience, [Online] Retrieved from the internet: <www.interscience.wiley.com DOI: 10.1002/bit.20026>, (2004), 19-26.
Jillavenkatesa, A, "Particle Size Characterization", National Institute of Standards and Technology, Special Publication 960-1, (2001), 1-167.
Jinping, Lai, et al., "Versatile Fluorescence Resonance Energy Transfer-Based Mesoporous Silica Nanoparticles for Real-Time Monitoring of Drug Release", ACS Nano, vol. 7, No. 3, (2013), 2741-2750.
Kaczanowska, Sabina, et al., "TLR agonists: our best frenemy in cancer immunotherapy", Journal of leukocyte Biology, 93(6), (2013), 847-863.
Kennedy, E M, et al., "Inactivation of the Human Papilloma virus E6 or E7 Gene in Cervical Carcinoma Cells by Using a Bacterial CRISPR/Cas RNA-Guided Endonuclease", Journal of Virology, (Aug. 6, 2014), 12 pgs.
Kim, D M, "A highly efficient cell-free protein synthesis system from *Excherichia coli*", Eur J Biochem, 239, (1996), 881-886.
Kim, E, et al., "Iodine 125-labeled mesenchymal-epithelial transition factor binding peptide-click-cRGDyk heterodimer for glioma imaging", Cancer Science, vol. 102, No. 8, (2011), 1516-1521.
Konermann, S, et al., "Genome-scale transcriptional activation by an engineered CRISPR-Cas9 complex", Nature, 2015, vol. 517, 583-588.
Kunkel, T. A., "Rapid and Efficient Site-Specific Mutagenesis Without Phenotypic Selection", Proc. Natl. Acad. Sci. USA, 82, (1985), 488-492.
Lacasse, E C, et al., "Nuclear localization signals overlap DNA- or RNA-binding domains in nucleic acid-binding proteins", Nucleic Acids Research, 23(10), (1995), 1647-1656.
Li, Z, et al., "Mesoporous Silica Nanoparticles in Biomedical Applications", Chemical Society Reviews 41, (2012), 2590-2605.
Lim, F, et al., "RNA recognition site of PP7 coat protein", Nucleic Acids Research, 30(19), (2002), 4138-4144.

(56) References Cited

OTHER PUBLICATIONS

Lingxiang, Wu, et al., "Synthesis of a Zwitterionic Silane and Its Application in the Surface Modification of Silicon-Based Material Surfaces for Improved Hemocompatibility", ACS Applied Materials & Interfaces, vol. 2 No. 10, (2010), 2781-2788.

Liu, J, et al., "Electrostatically Mediated Liposome Fusion and Lipid Exchange with a Nanoparticle-Supported Bilayer for Control of Surface Charge, Drug Containment, and Delivery.", J Am Chem Soc, 131, (2009), 7567-7569.

Liu, Juewen, et al., "Porous Nanoparticle Supported Lipid Bilayers (Protocells) as Delivery Vehicles", J. Am. Chem. Soc., vol. 131, No. 4, (2009), 7 pgs.

Liu, Juewen, et al., "Silica nanoparticle supported lipid bilayers for gene delivery.", Chem Commun, (2009), 5100-5102.

Liu, Xiangsheng, et al., "Irinotecan Delivery by Lipid-Coated Mesoporous Silica Nanoparticles Shows Improved Efficacy and Safety over Liposomes for Pancreatic Cancer", ACS Nano 10, (2016), 2702-2715.

Lo, et al., "Hepatocellular Carcinoma Cell-Specific Peptide Ligand for Targeted Drug Delivery", Molecular Cancer Therapeutics 7(3), (2008), 579-589.

Lu, Y, et al., "Aerosol-assisted self-assembly of mesostructured spherical nanoparticles", Nature, 398, (1999), 223-226.

Lu, Yunfeng, et al., "Continuous formation of supported cubic and hexagonal mesoporous films by sol-gel-dip-coating", Nature, 389(6649), (Sep. 25, 1997), 364-368.

Lu, Yunfeng, et al., "Evaporation-Induced Self-Assembly of Hybrid Bridged Silsesquioxane Film and Particulat Mesophases With Integral Organic Functionalitiy", Journal of the American Chemical Society, 122(22), (Jun. 1, 2000), 5258-5261.

Maghraby, EL, et al., "Interactions of surfactants (edge activators) and skin penetration enhancers with liposomes", Int. J. Pharm., vol. 276, No. 1-2, (2004), 143-161.

Mamaeva, Veronika, et al., "Mesoporous silica nanoparticles in medicine-Recent adva", Advanced Drug Delivery Reviews, Elsevier, Amsterdam, NL, vol. 65, No. 5, (Aug. 18, 2012), 689-702.

Martin, Kreutz, et al., "Targeting dendritic cells—why bother?", Blood, vol. 121, No. 15, (Apr. 11, 2013), 2836-2844.

Matteo, Porotto, et al., "Synthetic protocells interact with viral nanomachinery and inactivate pathogenic human virus", PLOS One, val. 6, No. 3, (Mar. 1, 2011), 16874 pgs.

McDonald, Michael, "Functioning Nanostructures Self-Assemble Out of Ink", Posted May 8, 2000, http://www.amtexpo.com/nano/messages/255.html, (May 8, 2000), 3 pgs.

Meng, Huan, et al., "Co-delivery of an Optimal Drug/siRNA Combination Using Mesoporous Silica Nanoparticle to Overcome Drug Resistance in Breast Cancer In Vitro and In Vivo", ACS Nano., (2013), 1-21.

Meng, Huan, et al., "Two-Wave Nanotherapy to Target the Stroma and Optimize Gemcitabine Delivery to a Human Pancreatic Cancer Model in Mice", ACS Nano vol. 7, No. 11, (2013), 10048-10065.

Meng, Huan, et al., "Use of a Lipid-Coated Mesoporous Silica Nanoparticle Platform for Synergistic Gemcitabine and Paclitaxel Delivery to Human Pancreatic Cancer in Mice", ACS Nano, vol. 9, No. 4, (2015), 3540-3557.

Meng, Huan, et al., "Use of Size and a Co-polymer Design Feature to Improve the Biodistribution and the Enhanced Permeability and Retention Effect of Doxorubicin-loaded Mesoporous Silica Nanoparticles in a Murine Xenograft Tumor Model", ACS Nano, (2011), 32 pgs.

Midoux, P, et al., "Membrane Permeabilization and Efficient Gene Transfer by a Peptide Containing Several Histidines", Bioconjugate Chem, 9, (1998), 260-267.

Milligan, ED, et al., "Pathological and protective roles of glia in chronic pain.", Nature Reviews Neuroscience, 10, (2009), 23-36.

Milligan, ED, et al., "Thermal hyperalgesia and mechanical allodynia produced by intrathecal administration of the human immunodeficiency virus-1 (HIV-1) envelope glycoprotein, gp 120.", Brain Research, 861, (2000), 105-116.

Milligan, Erin, et al., "Intrathecal polymer-based interleukin-10 gene delivery for neuropathic pain", Neuron Glia Biology 2, (2007), 1-16.

Mohamed, Salma, et al., "(Abstract) Polymeric nano-micelles: versatile platform for targeted delivery in cancer", Ther. Deliv., vol. 5, No. 10, pp. 1101-1121, (Oct. 2014), 1 pg.

Moller, K, et al., "Highly efficient siRNA delivery from core-shell mesoporous silica nanoparticles with multifunctional polymer caps", Nanoscale, 8, (2016), 13 pgs.

Mollick, Samraj, et al., "(Abstract) Outer Surface Hydrophobic Shielding Strategy to Enhance the Chemical Stability of Metal-Organic Polyhedra", Angew Chem Int Ed Engl, vol. 58, No. 4, pp. 1041-1045, (Jan. 21, 2019), 1 pg.

Mornet, et al., "The Formation of Support Lipid Bilayers on Silica Nanoparticles Revealed by Cryoelectron Microscopy", NanoLetters 5(2), (2005), 281-285.

Mungall, Bruce, et al., "Inhibition of Henipavirus infection by RNA interference", Antiviral Res., vol. 80, No. 3, (2008), 324-331.

Nakamura, Takashi, et al., "Nanoparticulation of BCG-CWS for application to bladder cancer therapy", Journal of Controlled Release vol. 176, (2014), 44-53.

Nekhotiaeva, Natalia, et al., "Inhibition of *Staphylococcus aureus* gene expression and growth using antisense peptide nucleic acids", Molecular Therapy, vol. 10, No. 4, 652-659.

Nikolic, M, et al., "Synthesis and characterization of mesoporous silica core-shell particles", Processing and Application of Ceramics, 4(2), (2010), 81-85.

Pastan, I, et al., "Immunotoxin therapy of cancer.", Nature Reviews 6, (2006), 559-565.

Peabody, D S, "A Viral Platform for Chemical Modification and Multivalent Display", Journal of Nanobiotechnology, 1, (2003), 1-8.

Peabody, D S, et al., "Immunogenic Display of Diverse Peptides on Virus-like Particles of RNA Phage MS2", J Mol Biol, 380, (2008), 1-18.

Peabody, D S, "Translational Repression by Bacteriophage MS2 Coat Protein Expressed from a Plasmid", The Journal of Biological Chemistry; 265(10), (1990), 5684-5689.

Pickett, G G, et al., "Encapsidation of heterologous RNAs by bacteriophage MS2 coat protein", Nucleic Acids Research, 21(19), (1993), 4621-4626.

PN, Durfee, et al., "Mesoporous Silica Nanoparticle-Supported Lipid Bilayers (Protocells) for Active Targeting and Delivery to Individual Leukemia Cells", ACS Nano, vol. 10, (2016), 8325-8345.

Porotto, M, et al., "Synthetic Protocells Interact with Viral Nano machinery and Inactivate Pathogenic Human Virus", (2011), 1-9 pgs.

Prokop, Ales, "Intracellular Delivery Fundamentals and Applications", ISBN Springer, (2011), 1-867.

Rao, G.V. R, et al., "Monodisperse Mesoporous Silica Microspheres Formed by Evaporation-Induced Self Assembly of Surfactant Templates in Aerosols", Adv. Mater, 14, No. 18, (Sep. 16, 2002), 1301-1304.

Raskopf, et al., "siRNA Targeting Vegf Inhibits Hepatocellular Carcinoma Growth and Tumor Angiogenesis In Vivo", Journal of Heptaology 49, (2008), 977-984.

Rodriguez, et al., "Minimal "Self" Peptides That Inhibit Phagocytic Clearance and Enhance Delivery of Nano particles", (2013), 971-975 pgs.

Rodriguez, F, et al., "DNA Immunization: Ubiquitination of a Viral Protein Enhances Cytotoxic T-Lymphocyte Induction and Antiviral Protection but Abrogates Antibody Induction", Journal of Virology, vol. 7 No. 11, (Nov. 1997), 8497-8503.

Rosenholm, Jessica M, et al., "Towards multifunctional, targeted drug delivery systems using mesoporous silica nanoparticles-opportunities", Nanoscale, vol. 2, No. 10, (Jan. 1, 2010), 1870-1883.

Russell, R G, et al., "Bisphosphonates: An Update on Mechanisms of Action and How These Relate to Clinical Efficacy", Ann NY Acad Sci 1117, (2007), 209-257.

Ryther, RCC, et al., "siRNA therapeutics: big potential from small RNAs", Gene Therapy, vol. 12, (2005), 5-11.

(56) References Cited

OTHER PUBLICATIONS

Sanjana, N E, et al., "Improved vectors and genome-wide libraries for CRISPR screening", Nat Methods, (2014), 783-784.
Sapra P. Allen TM, et al., "Internalizing Antibodies are Necessary for Improved Therapeutic Efficacy of Antibody-targeted Liposomal Drugs.", Cancer Res 62, (2002), 7190-7194.
Schiller, Renate, et al., "Synthesis of Mesoporous Silica Particles and Capsules by Miniemulsion Technique", Chem. Mater. 2009, 21, (Sep. 23, 2009), 11 pgs.
Seo, Seog-Jin, et al., "Gene delivery techniques for adult stem cell-based regenerative therapy", Nanomedicine, vol. 8, No. 11, (2013), 2 pgs.
Shiraishi, T., et al., "Photochemically enhanced cellular delivery of cell penetrating peptide-PNA conjugates.", FEBS Letters, 580(5), (2006), 1451-1456.
Shou-Cang, Shen, et al., "Mesoporous silica nanoparticle-functionalized poly(methylmethacrylate)-based bone cement for effective antibiotics delivery", Journal of Materials Science: Materials in Medicine, Kluwer Academic Publishers, BO,vol. 22, No. 10, (Jul. 24, 2011), 2283-2292.
Sloane, E, et al., "Chronic constriction injury induced pathological pain states are controlled long term via intrathecal administration of a non-viral vector (NW) encoding the anti-inflammatory cy1okine interleukin-10 (IL-10).", Second Joint Scientific Meeting of the American Pain Society and the Canadian Pain Society. Churchill Livingstone., (2004), p. 15.
Sloane, E, et al., "Immunological priming potentiates non-viral anti-inflammatory gene therapy treatment of neuropathic pain.". Gene Therapy, 16, (2009), 1210-1222.
Slowing, I I, et al., "(Abstract) Mesoporous silica nanoparticles as Controlled release drug delivery and gene transfection carriers", Advanced Drug Delivery Reviews vol. 60, Issue 11, (2008), 1278-1288.
Smothers, J F, et al., "Affinity Selection from Biological Libraries", Science, 298, (2002), 621-622.
Soderquist, et al., "Microparticle-mediated delivery of interleukin-1 0 plasmid DNA for the treatment of neuropathic pain", Poster Abstract No. 206d, (May 2008), 2 pgs.
Soderquist, R., et al., "Release of Plasmid DNA-Encoding IL-10 from PLGA Microparticles Facilitates Long-Term Reversal of Neuropathic Pain Following a Single Intrathecal Administration.", Pharmaceutical Research, (2010), 841-854.
Sorensen, Malin, "Mesostructured particulate silica materials with tunable pore size", Doctoral Thesis at the Royal Institute of Technology. Stockholm, Sweden,, (2009), 19-21.
Stemmer, WPC, et al., "Single-step assembly of a gene and entire plasmid from large numbers of oligodeoxyribonucleotides", Gene, 164, (1995), 49-53.
Suteewong, T, et al., "(Abstract) Synthesis and formation mechanism of aminated mesoporous silica nanoparticles", Chemistry of Materials, 24, (2012), 1 pg.
Suteewong, T, et al., "Highly aminated mesoporous silica nanoparticles with cubic pore structure", Journal of the American Chemical Society, 133(2), (2011), 172-175.
Takeuchi, S, "An Axisymmetric Flow-Focusing Microfluidic Device", Adv Mater, 17:8, (2005), 1067-1072.
Tarn, D, et al., "Mesoporous Silica Nanoparticle Nanocarriers: Biofunctionality and Biocompatibility.", Accounts of Chemical Research, (2013), 792-801.
Tatusova, T A, et al., "BLAST 2 Sequences, a new tool for comparing protein and nucleotide sequences", FEMS Microbiology Letters, 174, (1999), 247-250.
Tawfik, D S, et al., "Man-made cell-like compartments for molecular evolution", Nature Biotechnology; 16, (1998), 652-656.
Tejinder, Singh, et al., "The critical role of bisphosphonates to target bone cancer metastasis: an overview", Journal of Drug Targeting, vol. 23, (Sep. 9, 2014), 1-15.
Tianyi, Wang, et al., "Enhanced mucosal and systemic immune responses obtained by porous silica nanoparticles used as an oral vaccine adjuvant: Effect of silica architecture on immunological properties", International Journal of Pharmaceutics, vol. 436, No. 1-2, (Oct. 1, 2012), 351-358.
Torchilin, VP, et al., "Recent Advances with Liposomes as Pharmaceutical Carriers.", Nature Reviews, vol. 4, (2005), 145-159.
Townson, Jason L, et al., "Re-examining the Size/Charge Paradigm: Differing in Vivo Characteristics of Size- and Charge-Matched Mesoporous Silica Nanoparticles", J Am Chem Soc 135(43), (Oct. 30, 2013), 4 pgs.
Tran, Chris, et al., "Development of a second-generation antiandrogen for treatment of advanced prostate cancer", Science 324(5928), (2009), 787-790.
Uhlenbeck, O C, "A coat for all sequences", Nature structural biology, 5(3), (1998), 174-176.
Videira, et al., "Lymphatic uptake of lipid nanoparticles following endotracheal administration", Journal of Microencapsulation: Micro and Nano Carriers, 23(8), (2006), 855-862.
Villegas, et al., "Hybrid Collagenase Nanocapsules for Enhanced Nanocarrier Penetration in Tumoral Tissues", ACS Appl. Mater. Interfaces vol. 7, (2015), 24075-24081.
Vingerhoeds, et al., "Immunoliposome-mediated targeting of doxorubicin to human ovarian carcinoma in vitro and in vivo", British Journal of Cancer, (1996), 1023-29.
Wang, G, "Bisphosphonate-decorated lipid nanoparticles designed as drug carriers for bone diseases", Journal of Biomedical Materials Research A, vol. 100A, (Dec. 30, 2011), 684-693.
Wang, L-S, et al., "Biofunctionalized Phospholipid-Capped Mesoporous Silica Nanoshuttles for Targeted Drug Delivery: Improved Water Suspensibility and Decreased", ACS Nano, vol. 4 No. 8, (2010), 4371-4379.
Wang, Qingmin, et al., "Improved Cellular Immune Response Elicited by a Ubiquitin-Fused DNA Vaccine Against *Mycobacterium tuberculosis*", DNA and Cell Biology, vol. 31, No. 4, (2012), 489-495.
Wani, Amit, et al., "Surface Functionalization of Mesoporous Silica Nanoparticles Controls Loading and Release Behavior of Mitoxantrone", Pharmaceutical Research, Kluwer Academic Publishers-Plenum Publishers, NL, vol. 29, No. 9, (May 4, 2012), 2407-2418.
Weis, K, "Importins and exportins: how to get in and out of the nucleus", TIBS, 23, (1998), 185-189.
Wenyi, Gu, et al., "Nanotechnology in the targeted drug delivery for bone diseases and bone regeneration", International Journal of Nanomedicine, vol. 8, (2013), 2305-2317.
Wu, M, et al., "Cell-specific Delivery of Bacteriophage-Encapsidated Ricin A Chain", Bioconjugate Chem, 6, (1992), 587-595.
Xia, Tian, et al., "Polyethyleneimine Coating Enhances the Cellular Uptake of Mesoporous Silica Nanoparticles and Allows Safe Delivery of siRNA and DNA Constructs", ACS Nano; 3(10), (Oct. 27, 2009), 25 pgs.
Yamamoto, Satoshi, et al., "Synthesis of Fe70Pd30 nanoparticles and their surface modification by zwitterionic linker", Materials Chemistry and Physics 234, (2019), 237-244.
Yazdi, I, et al., "Novel mesoporous silicon particles as an efficient sustained delivery system for antibiotics", NSTI-Nanotech 2010, [Online] Retrieved from the Internet: <https://www.researchgate.net/profile/Iman Yazdi/publication/290613308 Novel mesoporous silicon particles as an efficient sustained delivery system-for antibiotics/links>, (Jan. 1, 2010), 324-325.
Youn, W, et al., "(Abstract) Cytoprotective Encapsulation of Individual Jurkat T Cells within Durable TiO2 Shells for T-Cell Therapy", Angew. Chem. Int. Ed., 56(36), pp. 10702-10706, (2017), 1 pg.
Yu-Shen, Lin, et al., "Well-Ordered Mesoporous Silica Nanoparticles as Cell Markers", Chem. Mater, 17, (2005), 4570-4573.
Zapryanova, et al., "Toroidal Microporous Silica Gel", Journal of Materials Science 14, (1979), 1175-1178 pgs.
Zelphati, et al., "Mechanism of Oligonucleotide Release from Cationic Liposomes", Proceedings of the National Academy of Sciences USA 93, (1996), 11493-98.
Zhang, Haiyuan, et al., "Differential Expression of Syndecan-1 Mediates Cationic Nanoparticle Toxicity in Undifferentiated versus Differentiated Normal Human Bronchial Epithelial Cells", ACS Nano, (2011), 1-29.

(56) References Cited

OTHER PUBLICATIONS

Zhang, Jing, et al., "Multifunctional Envelope-Type Mesoporous Silica Nanoparticles for Tumor-Triggered Targeting Drug Delivery", J. Am. Chem. Soc, 135 (13), (2013), 5068-5073.

Zhang, K, et al., "Facile Large-Scale Synthesis of Monodisperse Mesoporous Silica Nanospheres with Tunable Pore Structure", Journal of the American Chemical Society, (2013), 2427-2430.

Zhu, Wei, et al., "Modular Metal-Organic Polyhedra Superassambly: From Molecular-Level Design to Targeted Drug Delivery", Adv. Mater., vol. 31, No. 12, 1806774, (Mar. 2019), 10 pgs.

U.S. Appl. No. 09/838,153 U.S. Pat. No. 6,471,761, filed Apr. 20, 2001, Rapid Prototyping of Patterned Organic/Inorganic Functional Nanostructures.

U.S. Appl. No. 10/163,425 U.S. Pat. No. 6,913,832, filed Jun. 7, 2002, Prototyping of Patterned Functional Nanostructures.

U.S. Appl. No. 09/543,572, filed Apr. 5, 2000, Photo-Definable Self-Assembled Materials.

U.S. Appl. No. 10/100,108 U.S. Pat. No. 6,808,867, filed Mar. 19, 2002, Photo-Definable Self-Assembled Materials.

U.S. Appl. No. 10/373,565 U.S. Pat. No. 7,332,264, filed Feb. 26, 2003, Photo-Definable Self-Assembled Materials.

U.S. Appl. No. 09/389,085, filed Sep. 2, 1999, Low Frequency Feedback Speaker System.

U.S. Appl. No. 08/385,338, filed Feb. 8, 1995, Unidirectional Ring Laser Gyroscope.

U.S. Appl. No. 08/250,882 U.S. Pat. No. 5,438,585, filed May 31, 1994, Unstable Resonator Semiconductor Laser.

U.S. Appl. No. 16/500,349, filed Oct. 2, 2019, Porous Nanoparticle-Supported Lipid Bilayer Delivery of Transcriptional Gene Modulators.

U.S. Appl. No. 15/023,093, filed Mar. 18, 2016, Core and Surface Modification of Mesoporous Silica Nanoparticles to Achieve Cell Specific Targeting In Vivo.

U.S. Appl. No. 15/023,110 U.S. Pat. No. 9,855,217, filed Mar. 18, 2016, Toroidal Mesoporous Silica Nanoparticles (TMSNPS) and Related Protocells.

U.S. Appl. No. 15/858,923, filed Dec. 29, 2017, Toroidal Mesoporous Silica Nanoparticles (TMSNPS) and Related Protocells.

U.S. Appl. No. 14/350,674, filed May 20, 2014, Porous Nanoparticle-Supported Lipid Bilayers (Protocells) for Targeted Delivery Including Transdermal Delivery of Cargo and Methods Thereof.

U.S. Appl. No. 15/380,962, filed Dec. 15, 2016, Porous Nanoparticle-Supported Lipid Bilayers (Protocells) for Delivery Including Transdermal Delivery of Cargo and Methods Thereof.

U.S. Appl. No. 14/781,765, filed Nov. 23, 2015, Mesoporous Alum Nanoparticles as a Universal Platform for Antigen Adsorption, Presentation, and Delivery.

U.S. Appl. No. 12/909,572 U.S. Pat. No. 8,992,984, filed Oct. 21, 2010, Protocells and Their Use for Tarteteed Delivery of Multicomponent Cargos to Cancer Cells.

U.S. Appl. No. 14/627,739 U.S. Pat. No. 9,480,653, filed Feb. 20, 2015, Protocells and Their Use for Targeted Delivery of Multicomponent Cargos to Cancer Cells.

U.S. Appl. No. 14/797,487, filed Jul. 13, 2015, Protocells and Their Use for Targeted Delivery of Multicomponent Cargos to Cancer Cells.

U.S. Appl. No. 14/113,371 U.S. Pat. No. 9,579,283, filed Dec. 4, 2013, Porous Nanoparticle-Supported Lipid Bilayers (Protocells) for Targeted Delivery and Methods of Using Same.

U.S. Appl. No. 14/970,998 U.S. Pat. No. 10,022,327, filed Dec. 16, 2015, Porous Nanoparticle-Supported Lipid Bilayers (Protocells) for Targeted Delivery and Methods of Using Same.

U.S. Appl. No. 16/025,557, filed Jul. 2, 2018, Porous Nanoparticle-Supported Lipid Bilayers (Protocells) for Targeted Delivery and Methods of Using Same.

U.S. Appl. No. 14/781,817, filed Nov. 9, 2015, Antibiotic Protocells and Related Pharmaceutical Formulations and Methods of Treatment.

U.S. Appl. No. 15/474,800, filed Mar. 30, 2017, Protocells for Plasmid and RNP Delivery in the Treatment of Cancer of Other Disease States.

U.S. Appl. No. 15/474,810, filed Mar. 30, 2017, Carriers or Plasmid and RNP Delivery in the Treatment of Cancer of Other Disease States.

U.S. Appl. No. 14/369,741, filed Jun. 30, 2014, CRLF-2 Binding Peptides, Protocells and Viral-Like Particles Useful in the Treatment of Cancer, Including Acute Lymphoblastic Leukemia (ALL).

U.S. Appl. No. 15/788,634, filed Oct. 19, 2017, CRLF-2 Binding Peptides, Protocells and Viral-Like Particles Useful in the Treatment of Cancer, Including Acute Lymphoblastic Leukemia (ALL).

U.S. Appl. No. 13/143,164 U.S. Pat. No. 8,734,816, filed Jul. 1, 2011, Porous Nanoparticle Supported Lipid Bilayer Nanostructures.

U.S. Appl. No. 14/253,030, filed Apr. 15, 2014, Porous Nanoparticle Supported Lipid Nanostructures.

U.S. Appl. No. 15/557,368, filed Sep. 11, 2017, Generation of Mesoporous Materials Using Multiphase Surfactant Systems.

U.S. Appl. No. 12/903,577, filed Oct. 13, 2010, Protocells and Their Use for Pain Treatment.

U.S. Appl. No. 15/757,254, filed Mar. 2, 2018, Protocells to Treat Microbial Infection and for Synergistic Delivery.

U.S. Appl. No. 15/757,269, filed Mar. 2, 2018, Mesoporous Silica Nanoparticles and Supported Lipid Bi-Layer Nanoparticles for Biomedical Applications.

U.S. Appl. No. 16/828,137, filed Mar. 24, 2020, Mesoporous Silica Nanoparticles and Supported Lipid Bi-Layer Nanoparticles for Biomedical Applications.

U.S. Appl. No. 15/557,000, filed Sep. 8, 2017, CD 47 Containing Porous Nanoparticle Supported Lipid Bilayers (Protocells) Field of the Invention.

U.S. Appl. No. 16/068,235, filed Jul. 5, 2018, Osteotropic Nanoparticles for Prevention or Treatment of Bone Metastases.

U.S. Appl. No. 16/490,280, filed Aug. 30, 2019, Active Targeting of Cells by Monosized Protocells.

U.S. Appl. No. 16/635,246, filed Jan. 30, 2020, Liposomal Coated Nanoparticles for Immunotherapy Applications.

U.S. Appl. No. 15/887,619, filed Feb. 2, 2018, Porous Nanoparticle-Supported Lipid Bilayers (Protocells) for Delivery Including Transdermal Delivery of Cargo and Method Thereof.

U.S. Appl. No. 16/976,651, filed Aug. 28, 2020, Starry Mesoporous Silica Nanoparticles and Supported Lipid Bi-Layer Nanoparticles.

U.S. Appl. No. 17/264,452, filed Jan. 29, 2021, Biomimetic Rebuilding of Multifunctional Red Blood Cells.

U.S. Appl. No. 17/277,260, filed Mar. 17, 2021, Armored Cells.

U.S. Appl. No. 17/434,363, filed Aug. 26, 2021, Modular Metal—Organic Polyhedra Superassembly Compositions.

"International Application Serial No. PCT/US2019/052658, International Search Report mailed Mar. 12, 2020", 3 pgs.

"International Application Serial No. PCT/US2019/052658, Written Opinion mailed Mar. 12, 2020", 4 pgs.

"International Application Serial No. PCT/US2019/052669, International Search Report mailed Jan. 9, 2020", 3 pgs.

"International Application Serial No. PCT/US2019/052669, Written Opinion mailed Jan. 9, 2020", 5 pgs.

Chedid, Georgeset, et al., "Recent Trends in Covalent and Metal Organic Frameworks for Biomedical Applications", Nanomaterials (Basel), 8(11)., (Nov. 7, 2018), 27 pgs.

Lu, Weigang, et al., "Tuning the structure and function of metal-organic frameworks via linker design", Chemical Society Reviews, 43, (2014), 5561-5593.

Mao, A, et al., "Deterministic encapsulation of single cells in thin tunable microgels for niche modeling and therapeutic delivery", Nat Mater 16, pp. 236-243, (2017), 21 pgs.

Park, J, et al., "Cell-in-Shell Hybrids: Chemical Nanoencapsulation of Individual Cells", Acc. Chem. Res., 49(5), (2016), 792-800.

Ricco, R, et al., "Metal-Organic Frameworks for Cell and Virus Biology: A Perspective", ACS Nano, 12, (Jan. 8, 2018), 13-23.

Rocca, F D, et al., "Cell Composition of the Human Pulmonary Valve: A Comparative Study With the Aortic Valve-The VESALIO* Project", Ann Thorac Surg. 70, (2000), 1594-1600.

(56) References Cited

OTHER PUBLICATIONS

Zhu, Kelong, et al., "Metal-Organic Frameworks with Mechanically Interlocked Pillars: Controlling Ring Dynamics in the Solid-State via a Reversible Phase Change", J Am Chem Soc. 136(20), (May 21, 2014), 7403-7409.
"U.S. Appl. No. 16/635,246, Advisory Action mailed Oct. 5, 2023", 3 pgs.
"U.S. Appl. No. 16/635,246, Non Final Office Action mailed Nov. 1, 2023", 25 pgs.
"U.S. Appl. No. 16/635,246, Response filed Sep. 25, 2023 to Final Office Action mailed Jul. 25, 2023", 8 pgs.
"U.S. Appl. No. 17/277,260, Restriction Requirement mailed Nov. 20, 2023", 9 pgs.
Lee, Juno, et al., "Chemical sporulation and germination: cytoprotective nanocoating of individual mammalian cells with a degradable tannic acid-FeIII complex", Nanoscale 7(45), (2015), 18918-18922.
Valentina, Colapicchioni, et al., "Killing cancer cells using nanotechnology: novel poly(I:C) loaded liposome-silica hybrid nanoparticles", Journal of Materials Chemistry B, vol. 3, (2015), 7408-7416.
"U.S. Appl. No. 16/068,235, Notice of Allowance mailed Feb. 13, 2023", 5 pgs.
"U.S. Appl. No. 16/068,235, Notice of Allowance mailed Oct. 12, 2022", 5 pgs.
"U.S. Appl. No. 16/068,235, Supplemental Notice of Allowability mailed Feb. 21, 2023", 2 pgs.
"U.S. Appl. No. 16/068,235, Supplemental Notice of Allowability mailed Oct. 17, 2022", 2 pgs.
"U.S. Appl. No. 16/500,349, Non Final Office Action mailed Nov. 30, 2022", 13 pgs.
"U.S. Appl. No. 16/500,349, Response filed Feb. 28, 2023 to Non Final Office Action mailed Nov. 30, 2022", 8 pgs.
"U.S. Appl. No. 16/500,349, Response filed Aug. 22, 2022 to Restriction Requirement mailed Jun. 22, 2022", 8 pgs.
"U.S. Appl. No. 16/635,246, Advisory Action mailed Jan. 27, 2023", 5 pgs.
"U.S. Appl. No. 16/635,246, Final Office Action mailed Sep. 19, 2022", 19 pgs.
"U.S. Appl. No. 16/635,246, Response filed Jan. 19, 2023 to Final Office Action mailed Sep. 19, 2022", 7 pgs.
"U.S. Appl. No. 16/635,246, Response filed Mar. 17, 2023 to Advisory Action mailed Jan. 27, 2023", 8 pgs.
"U.S. Appl. No. 16/635,246, Response filed Aug. 31, 2022 to Non Final Office Action mailed May 31, 2022", 8 pgs.
"U.S. Appl. No. 16/976,651, Examiner Interview Summary mailed Jan. 27, 2023", 4 pgs.
"U.S. Appl. No. 16/976,651, Non Final Office Action mailed Feb. 28, 2023", 29 pgs.
"U.S. Appl. No. 16/976,651, Non Final Office Action mailed Nov. 2, 2022", 37 pgs.
"U.S. Appl. No. 16/976,651, Response filed Feb. 1, 2023 to Non Final Office Action mailed Nov. 2, 2022", 13 pgs.
"U.S. Appl. No. 16/976,651, Response filed Oct. 19, 2022 to Non Final Office Action mailed Jul. 19, 2022", 10 pgs.
Berge, Stephen M, et al., "Pharmaceutical Salts", Journal of Pharmaceutical Sciences, 66(1), (Jan. 1977), 1-19.
Doshi, Nishit, et al., "Red blood cell-mimicking synthetic biomaterial particles", PNAS, vol. 106, No. 51, (Dec. 22, 2009), 21495-21499.
Langley, P J, "Nanoporous and mesoporous organic structures: new openings for materials research", Chemical Society Reviews, vol. 28, (1999), 279-291.
Maeder, Morgan L, et al., "CRISPR RNA-guided activation of endogenous human genes", Nature Methods, vol. 10, No. 10, (2013), 977-979.
Merkel, Timothy J., et al., "Using mechanobiological mimicry of red blood cells to extend circulation times of hydrogel microparticles", PNAS, vol. 108, No. 2, (Jan. 11, 2011), 586-591.

Qi, Lei S., et al., "Repurposing CRISPR as RNA-Guided Platform for Sequence-Specific Control of Gene Expression", Cell, 152(5), (2013), 22 pgs.
Taylor, Erik N., et al., "Monitoring Therapeutic Responses to Silicified Cancer Cell Immunotherapy Using PET/MRI in a Mouse Model of Disseminated Ovarian Cancer", Int. J. Mol. Sci. 2022, 23(18), 10525, (Sep. 10, 2022), 14 pgs.
Wan, Chao, et al., "Activation of the hypoxia-inducible factor-1a pathway accelerates bone regeneration", PNAS, vol. 105, No. 2, (2008), 686-691.
Wang, Zhen, et al., "Targeting p53 for Novel Anticancer Therapy", Translational Oncology, vol. 3, No. 1, (2010), 1-12.
"U.S. Appl. No. 16/068,235, Examiner's Amendment Communication mailed Mar. 16, 2022", 20 pgs.
"U.S. Appl. No. 16/068,235, Notice of Allowance mailed May 11, 2022", 27 pgs.
"U.S. Appl. No. 16/500,349, Restriction Requirement mailed Jun. 22, 2022", 9 pgs.
"U.S. Appl. No. 16/635,246, Non Final Office Action mailed May 31, 2022", 19 pgs.
"U.S. Appl. No. 16/976,651, Non Final Office Action mailed Jul. 19, 2022", 34 pgs.
"U.S. Appl. No. 16/976,651, Response filed Apr. 11, 2022 to Restriction Requirement mailed Mar. 9, 2022", 6 pgs.
Balas, Francisco, et al., "Confinement and Controlled Release of Bisphosphonates on Ordered Mesoporous Silica-Based Materials", Journal of the American Chemical Society, vol. 128, 2006, (2006), 8116-8117.
Einkolopiyan, N. S., "New Aspects of the Nucleophilic Opening of Epoxide Rings", Pure & Applied Chemistry, vol. 48, Perpmon Pross, 1976, (1976), 317-328.
Guo, Jimin, et al., "Cancer vaccines from cryogenically silicified tumour cells functionalized with pathogen-associated molecular patterns", Nature Biomedical Engineering vol. 6, (Jan. 2022), 19-31.
James, J Kobie, et al., "Transforming Growth Factor B Inhibits the Antigen-Presenting Functions and Antitumor Activity of Dendritic Cell Vaccines", Cancer Research, vol. 63, (Apr. 15, 2003), 1860-1864.
Kun, Zhang, et al., "Facile Large-Scale Synthesis of Monodisperse Mesoporous Silica Nanospheres with Tunable Pore Structure (Supporting Information)", Journal of the American Chemical Society, vol. 135,, (2013), 16 pgs.
Lin, Xiong, et al., "Tunable stellate mesoporous silica nanoparticles for intracellular drug delivery", Journal of Materials Chemistry B, vol. 3, (2015), 1712-1721.
Pignatello, Rosario, et al., "A novel biomaterial for osteotropic drug nanocarriers; synthesis and biocompatibility evaliation of a PLGA-ALE conjugate.", Nanomedicine, vol. 4(2), 2009, (2009), 161-175.
Socorro, Espuelas, et al., "Influence of Ligand Valency on the Targeting of Immature Human Dendritic Cells by Mannosylated Liposomes", Bioconjugate Chemistry, vol. 19, (2008), 2385-2393.
Yao, Sun, et al., "Stimuli-Responsive Shapeshifting Mesoporous Silica Nanoparticles", Nano Letters, vol. 16, (2016), 651-655.
Yao, Sun, et al., "Stimuli-Responsive Shapeshifting Mesoporous Silica Nanoparticles (Supporting Information)", Nano Letters, vol. 1, of supporting information, (2016), 1-11.
"U.S. Appl. No. 17/277,260, Response filed Jan. 22, 2024 to Restriction Requirement mailed Nov. 20, 2023", 6 pgs.
"U.S. Appl. No. 16/976,651, Response filed Jan. 29, 2024 to Final Office Action mailed Jul. 27, 2023", 12 pgs.
"U.S. Appl. No. 16/976,651, Non Final Office Action mailed Feb. 7, 2024", 31 pgs.
"U.S. Appl. No. 16/635,246, Final Office Action mailed May 13, 2024", 28 pgs.
"U.S. Appl. No. 16/635,246, Response filed May 1, 2024 to Non Final Office Action mailed Nov. 1, 2023", 7 pgs.
"U.S. Appl. No. 17/264,452, Response filed Jun. 24, 2024 to Restriction Requirement mailed Mar. 22, 2024", 7 pgs.
"U.S. Appl. No. 17/264,452, Restriction Requirement mailed Mar. 22, 2024", 12 pgs.
"U.S. Appl. No. 17/277,260, Non Final Office Action mailed Mar. 14, 2024", 27 pgs.

(56) References Cited

OTHER PUBLICATIONS

"U.S. Appl. No. 17/277,260, Response filed Jun. 11, 2024 to Non Final Office Action mailed Mar. 14, 2024", 15 pgs.
"U.S. Appl. No. 17/434,363, Non Final Office Action mailed Mar. 21, 2024", 6 pgs.
"U.S. Appl. No. 17/434,363, Response filed Jun. 11, 2024 to Non Final Office Action mailed Mar. 21, 2024", 6 pgs.
"International Application Serial No. PCT/US2024/017524, International Search Report mailed Jul. 3, 2024", 5 pgs.
"International Application Serial No. PCT/US2024/017524, Written Opinion mailed Jul. 3, 2024", 5 pgs.
Allen, Theresa M, et al., "Use of the Post-Insertion Method for the Formation of Ligand-Coupled Liposomes", Cell & Molecular Biology Letters, vol. 7, (2022), 889-894.
Clem, Paul, et al., "Biomolecular Materials Meeting", pp. 13-19, [Online] Retrieved from the internet: <//efaidnbmnn-nibpcajpcglclefindmkaj/https://science.osti.gov/-/media/bes/mse/pdf/docs/Materials-Discovery-Design-and-Synthesis-Team/2015_Biomolecular_Materials_PI_Meeting_abstracts_book.pdf>, (2015), 272 pgs.
Lu, et al., "Nanoscale metal-organic frameworks for therapeutic, imaging, and sensing applications", Advanced Materials, 30, (2018), 20 pgs.
Rabinowitz, Harold, et al., "The Manual of Scientific Style—A Guide for Authors, Editors, and Researchers", 1st ed. San Diego, CA, USA: Elsevier Science, Chapter 3—Elements of Style and Usage, (2009), 131-260.
Yang, et al., "Coating process and stability of metal-polyphenol film", Colloids and Surfaces A: Physicochem. Eng. Aspects 484, (2015), 197-205.
Zhu, Wei, et al., "Modular Metal-Organic Polyhedra Superassembly: From Molecular-Level Design to Targeted Drug Delivery", Adv. Mater. 2019,31,1806774, (Jan. 31, 2019), 1-10.
"U.S. Appl. No. 17/434,363, Notice of Allowance mailed Sep. 23, 2024", 8 pgs.
"U.S. Appl. No. 18/834,513, Preliminary Amendment filed Jul. 30, 2024", 9 pgs.
"International Application Serial No. PCT/US2023/061675, International Preliminary Report on Patentability mailed Aug. 15, 2024", 8 pgs.
Porras, Gonzalez Maria, et al., "Integrins and extracellular matrix proteins modulate adipocyte thermogenic capacity", Scientific Reports, 11:5442, [Online]. Retrieved from the Internet: <URL: https://doi.org/10.1038/s41598-021-84828-z>, (2021), 14 pgs.
"U.S. Appl. No. 17/434,363, Corrected Notice of Allowability mailed Oct. 25, 2024", 5 pgs.
"U.S. Appl. No. 17/277,260, Final Office Action mailed Oct. 10, 2024", 24 pgs.

\* cited by examiner

LIVING MAMMALIAN CELLS MODIFIED WITH FUNCTIONAL MODULAR NANOPARTICLES

CROSS-REFERENCE TO RELATED APPLICATIONS

This application is a U.S. National Stage Filing under 35 U.S.C. 371 from International Application No. PCT/US2019/052658, filed on Sep. 24, 2019, and published as WO 2020/068798 on Apr. 2, 2020, which application claims the benefit of the filing date of U.S. application No. 62/735,585, filed on Sep. 24, 2018, the disclosures of which are incorporated by reference herein.

STATEMENT OF GOVERNMENT SUPPORT

This invention was made with government support under FA9550-14-1-0066 awarded by the Air Force Office of Scientific Research, under DE-FG02-02ER15368 awarded by the Department of Energy, under EEC-1647722 awarded by the National Science Foundation, and under DENA-0003 525 awarded by the Department of Energy, Sandia National Labs Laboratory Directed Research and Development. The government has certain rights in the invention.

BACKGROUND

Enhancing or augmenting the performance of mammalian cells could result in new classes of smart responsive living materials. Mammalian cells exhibit complex functionalities like sensing, signal transduction and protein expression but they remain fragile and highly susceptible to intracellular and extracellular stressors. Recently, to impart greater cellular durability, cytoprotective material nanolayers, such as silica, titania, cross-linked polymer and metal-phenolic networks (Park et al., 2016; Riccò et al., 2018; Park et al., 2010; Mao et al., 2017), have been coated on individual mammalian cells increasing resistance against UV, freezing, and enzymatic attack (Lee et al., 2014; Youn et al., 2017; Lee et al., 2007; Oliveira et al., 2016; Park et al., 2014). However, the current thin film encapsulation approach is limited by the incompatibility of most material synthesis conditions (pH, temperature, precursor concentration, etc.) with cellular survival, arduous steps of synthetic optimization to obtain a cytoprotective layer, poor biocompatibility due to low permeability, and general inability to impart multiple augmented functionalities to the encapsulated cells needed for versatile intelligent cell-based device purposes (Ho and Bennett, 2018).

Synthetic nanoparticles (NPs) with various chemical compositions and diverse functionalities naturally interact with mammalian cell surfaces through multiple non-covalent binding interactions developed with proteins and other cellular membrane components. Often these interactions lead to NP accumulation and subsequent internalization by phagocytosis or macropinocytosis based on membrane extension or invagination and wrapping of individual or groups of nanoparticles (Fleischer and Payne, 2014; Verma and Stellacci, 2010; Croissant et al., 2017).

SUMMARY

Compared to bacteria and yeast whose cell walls are robust and provide a protective environment, mammalian cells are inherently fragile due to the flexibility of their cell membranes which is needed to support various internalization pathways such as phagocytosis and endocytosis. Creating a synthetic exoskeleton from abiotic materials to protect cells and impart them with new functionalities could revolutionize fields like cell-based sensing and create unique cellular phenotypes. Disclosed herein are 'SupraCells' which are living mammalian cells encapsulated, and thus protected, within functional modular nanoparticle-based exoskeletons. The exoskeletons are generated, e.g., within seconds, through interparticle and cell/particle complexation that inhibits, and in one embodiment, abolishes, the macropinocytotic and endocytotic nanoparticle internalization pathways that occur without complexation. Supracell formation was shown to be generalizable to nanoparticles and cells based on testing of a variety of nanoparticles and cells, resulting in a spore-like state, where cells are inhibited from replicating or do not replicate, and/or do not spread on surfaces but are endowed with new or improved properties, e.g., extremophile properties, e.g., resistance to osmotic stress, ROS, pH, and/or UV exposure, or abiotic properties like magnetism, conductivity, and/or multi-fluorescence, or a combination thereof. Upon de-complexation, cells return to their normal replicative states. Supracells represent a unique class of living hybrid materials with numerous functionalities. Thus, in one embodiment, the disclosure provides mammalian 'SupraCells' that display one or more normal (native, unmodified) cell functions plus SupraCell-resistances and/or SupraCell-properties via nanoparticle-based exoskeletons.

In one embodiment, an encapsulated living mammalian cell which comprises a plurality of linked nanoparticles enveloping the cell is provided. In one embodiment, the cell is a human cell. In one embodiment, the cell is a stem cell. In one embodiment, the cell is a brain cell, liver cell, cardiac cell, spleen cell, macrophage, pancreatic cell, T cell, B cell or dendritic cell. In one embodiment, an individual nanoparticle has a diameter of about 5 nm to about 500 nm, about 10 nm to about 300 nm or about 15 nm to about 250 nm. In one embodiment, the nanoparticles are metal-organic nanoparticles. In one embodiment, the nanoparticles comprise Zn or Co imidazolate. In one embodiment, the nanoparticles comprise iron oxide. In one embodiment, the nanoparticles are linked using tannic acid. In one embodiment, the nanoparticles are linked via a metal-phenolic interaction. In one embodiment, the nanoparticles are linked via a boronic acid-phenolic acid interaction. In one embodiment, the nanoparticles are linked via a thiol linkage. In one embodiment, the nanoparticles are functionalized with amine or phenol prior to linking. In one embodiment, the nanoparticles are functionalized with thiol prior to linking. In one embodiment, the linkage is reversible. In one embodiment, the linker is reversible by a metal chelator, e.g., EDTA, EGTA, dimercaprol, desferoxamine, 3-hydroxypyridin-4-one, sodium diethyldithiocarbamate, deferiprone, D-penicillamine, desferasirox, N,N',N'-tetrakis-(2-pyridylmethyl)ethylenediamine, diethylenetriaminepentaacetic acid, or desferrioxamine B. In one embodiment, a thiol linkage is reversible by, for example, glutathione disulfide.

Further provided are methods of making the encapsulated cells. In one embodiment, an amount of a plurality of mammalian cells and an amount of a plurality of nanoparticles, which may include a combination of two or more different types of nanoparticles, which are functionalized with one or more linkers are combined under conditions that result in one or more mammalian cells being encapsulated with a plurality of linked nanoparticles. In one embodiment, an amount of a plurality of mammalian cells, an amount of a plurality of nanoparticles, and an amount of one or more linkers (e.g., structurally identical or distinct linkers) are combined e.g., in any order, under conditions that result in one or more mammalian cells being encapsulated with a plurality of linked nanoparticles. In one embodiment, the encapsulated mammalian cells have sensing, electrical and/ or magnetic properties.

DETAILED DESCRIPTION

Figure 1:
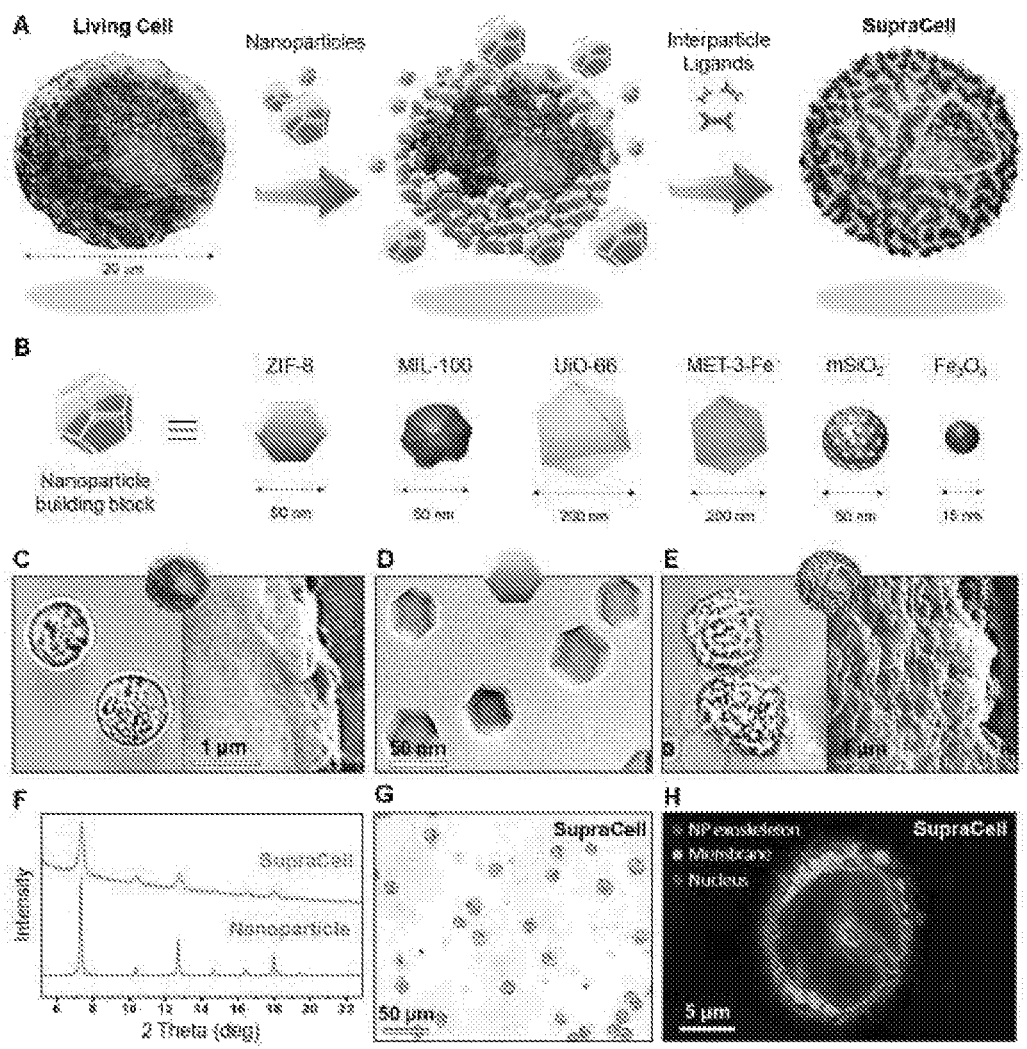
FIGS. 1A-H. Formation and characterization of exemplary SupraCells. (A) Representation of the incubation of NPs into mammalian cells (first arrow) and the 'freezing' of the NPs endocytosis stage via the addition of inter-particle ligands (second arrow) to form SupraCells. (B) Representation of various NP building blocks including MOFs (e.g., ZIF-8, MIL-100, UiO-66, MET-3-Fe), mesoporous silica ($mSiO_2$), and iron oxide ($Fe_3O_4$) NPs. (C) Bright field (left) and scanning electron (right) images of HeLa cells. (D) Transmission electron image of ZIF-8 nanobuilding blocks. (E) Bright field (left) and scanning electron (right) images of HeLa SupraCells based on ZIF-8 nanobuilding blocks. (F) X-ray diffraction pattern of Supra-HeLa Cell-ZIF-8 and ZIF-8 NPs. (G) Low-magnification bright field image of SupraCells. (H) Z-stack confocal image of a SupraCell demonstrating the homogeneous formation of the NP-based exoskeleton (red-colored).

The natural coherence of the NP/cellular membrane interface suggests that NPs might be ideal candidates for cellular encapsulation if accompanying NP internalization mechanisms could be suppressed. Herein is described a general cellular encapsulation approach, so-called 'SupraCells', wherein living mammalian cells are coated with a functional, modular, nanoparticle (NP)-based exoskeleton generated by 'freezing' NP cellular internalization using inter-nanoparticle ligands (FIG. 1A). This simple universal approach is highly biocompatible with various cell types and provides an ability to endow the encapsulated cell with useful, almost limitless, tunable physico-chemical properties (e.g., optical, magnetic, and/or sensing properties) depending on the NPs or NP combinations (FIG. 1B). The potential chemical diversity of supracells is enormous. As disclosed herein, SupraCell prototypes were prepared with NP-exoskeletons including metal-organic frameworks (e.g., ZIF-8, MIL-100, UiO-66-NH2, and MET-3-Fe types), mesoporous silica nanoparticles (MSNs and dye-labeled MSNs), iron oxide ($Fe_3O_4$) NPs (FIG. 1B), and NP combinations. Supra-cell formation maintains normal cellular functions (e.g., viability, metabolism) but induces a spore-like state, where in one embodiment, cells fail to replicate or spread on surfaces but are endowed with extremophile properties, e.g., resistance to osmotic stress, ROS, pH, and UV exposure. NP functionality confers to the cell abiotic properties including tunable cell-mechanics, selective permeability, intracellular activity sensing, multi-fluorescence, magnetism, and/or conductivity, which are foreign to the native mammalian cells.

Figure 5:
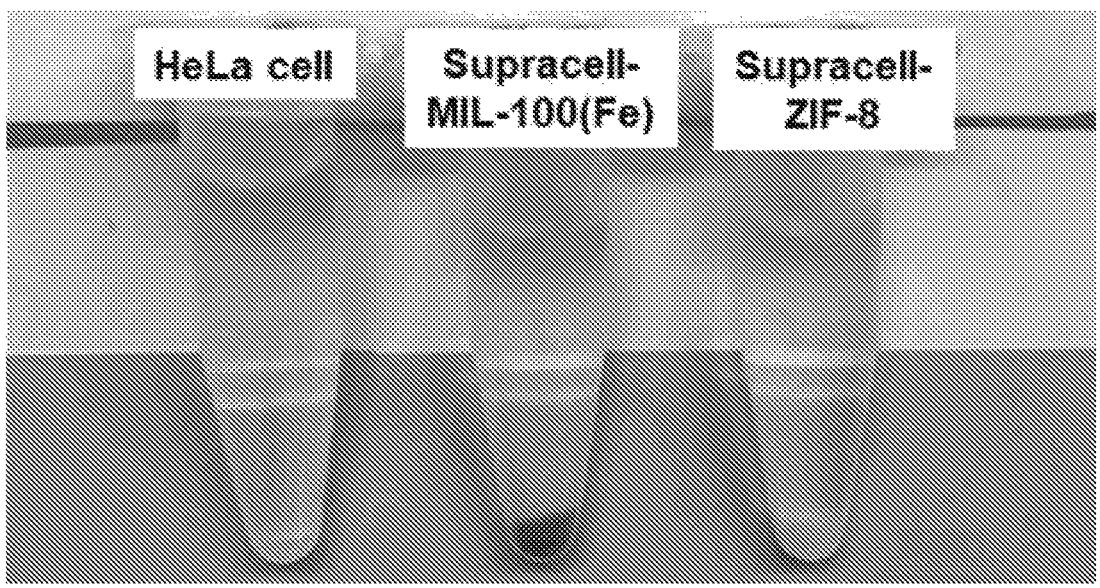
FIG. 5. Optical image of the pellets of HeLa cell, Supra-HeLa cell-MIL-100 (Fe), and Supra-HeLa cell-ZIF-8.
Figure 6:
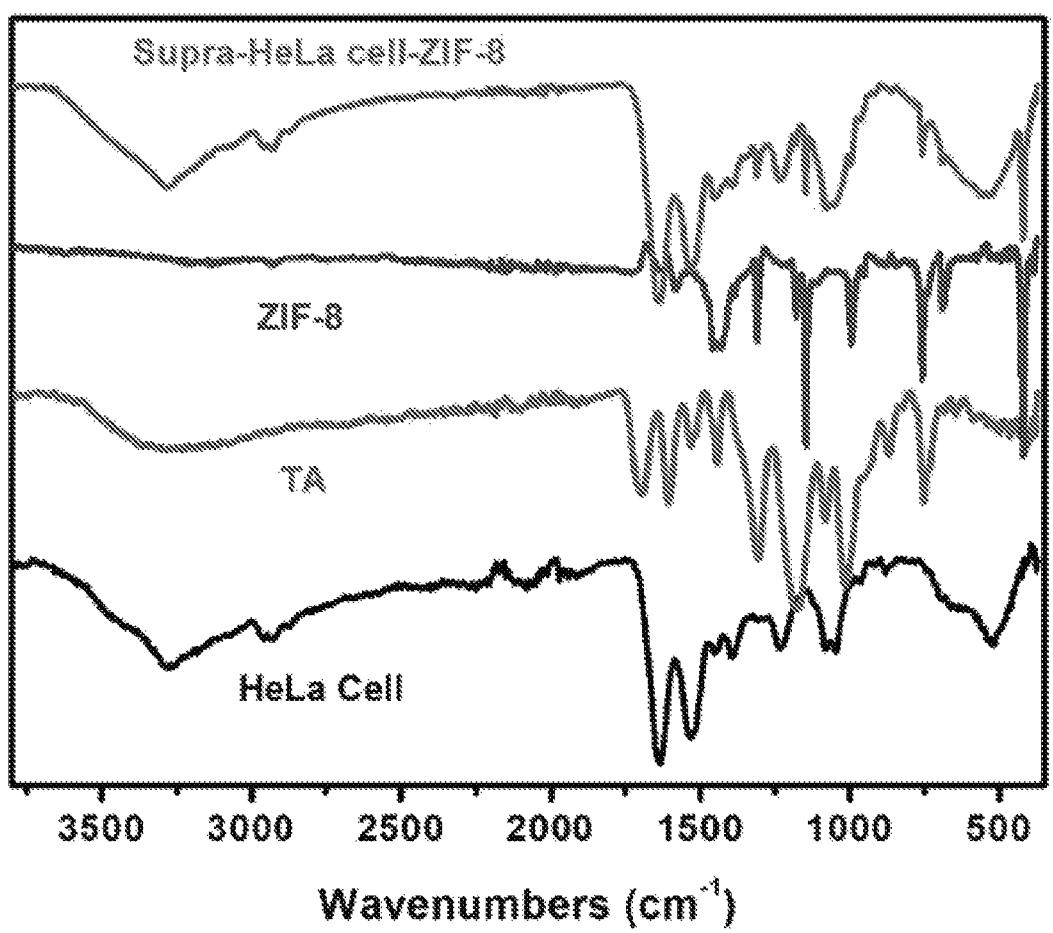
FIG. 6. Fourier transform infrared spectrophotometry (FT-IR) of the HeLa cell, tannic acid, ZIF-8 NPs, and Supra-HeLa cell-ZIF-8.
Figure 7:
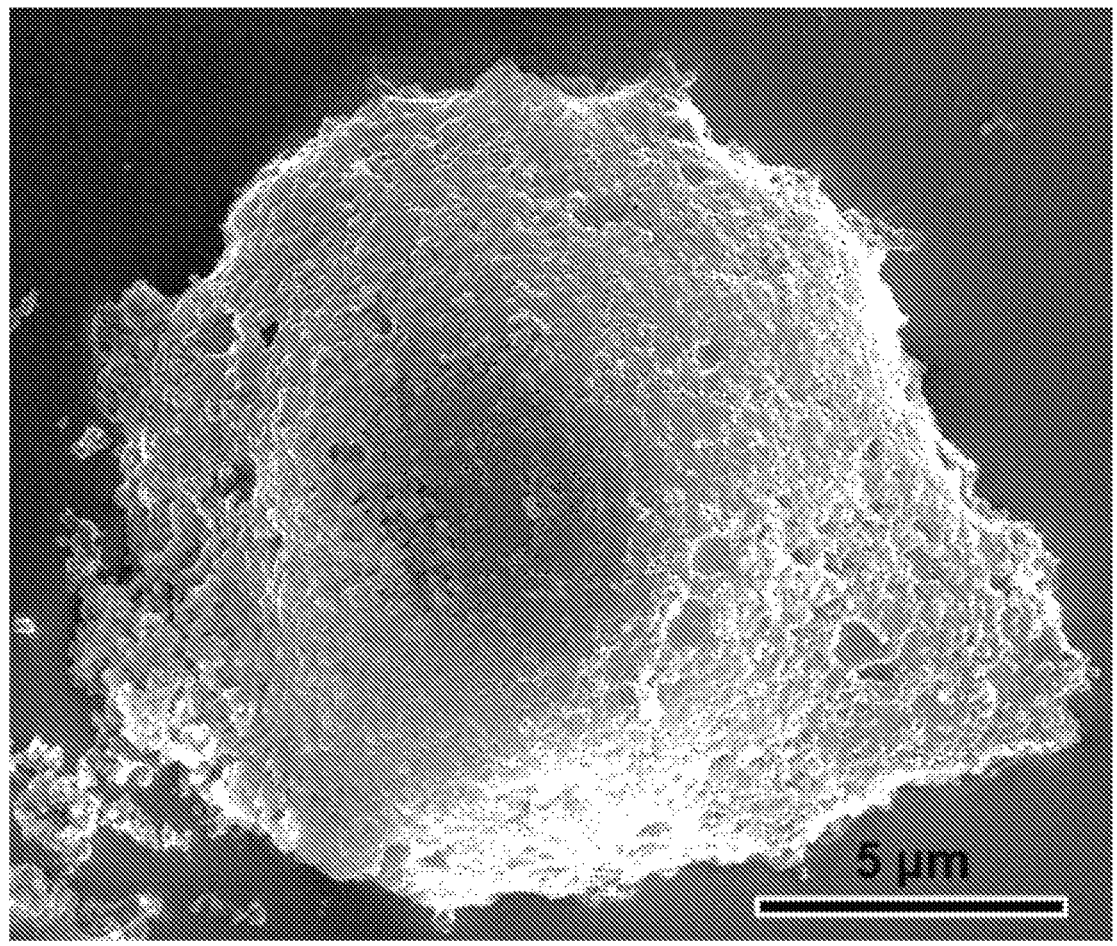
FIG. 7. SEM image of the Supra-HeLa cell-ZIF-8.
Figure 8:
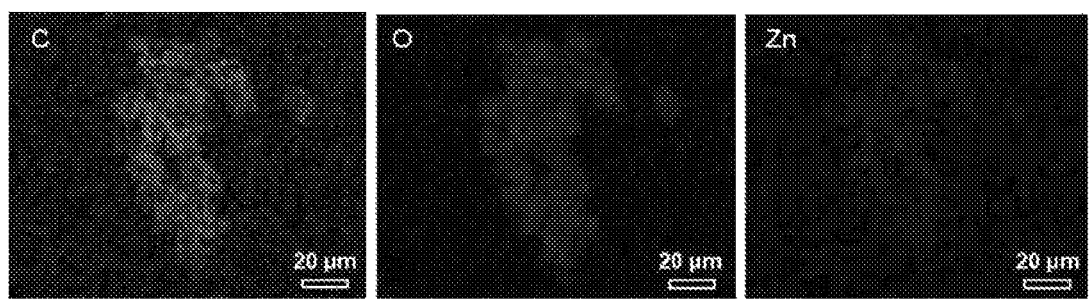
FIG. 8. EDS carbon, oxygen, and zinc elemental mappings of the Supra-HeLa cell-ZIF-8.
Figure 9:
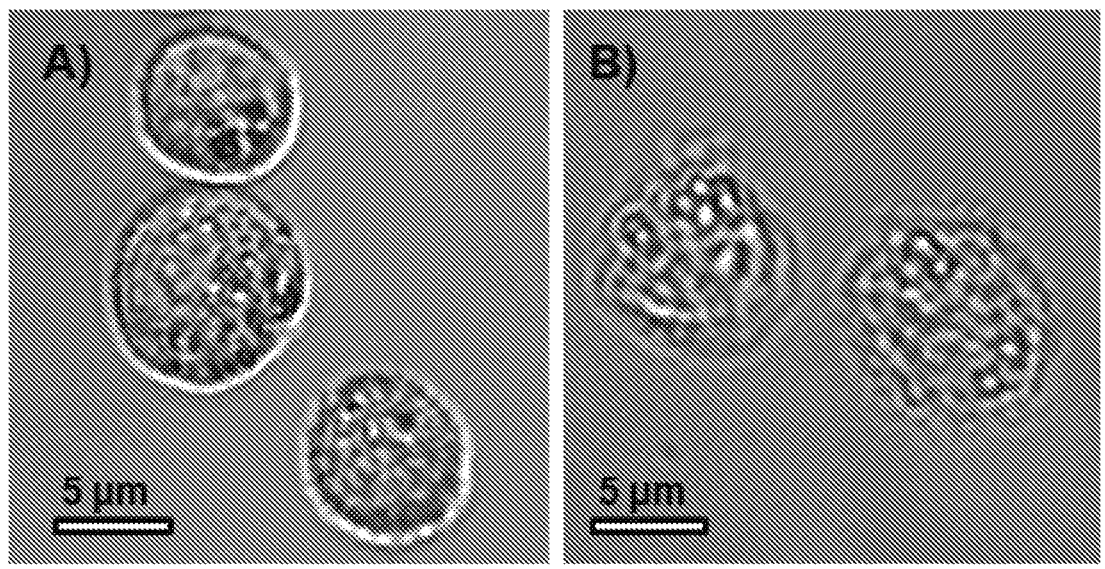
FIGS. 9A-B. Bright field image of A549 cell (A) and Supra-A549 Cell-ZIF-8 (B).
Figure 10:
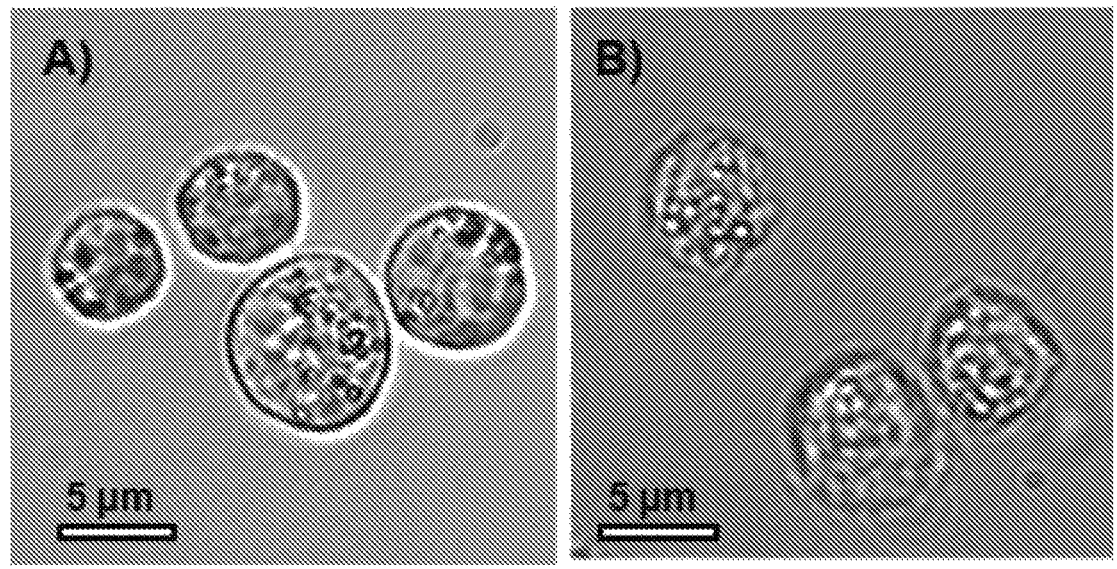
FIGS. 10A-B. Bright field image of HL-60 cell (A) and Supra-HL-600 cell-ZIF-8 (B).
Figure 11:
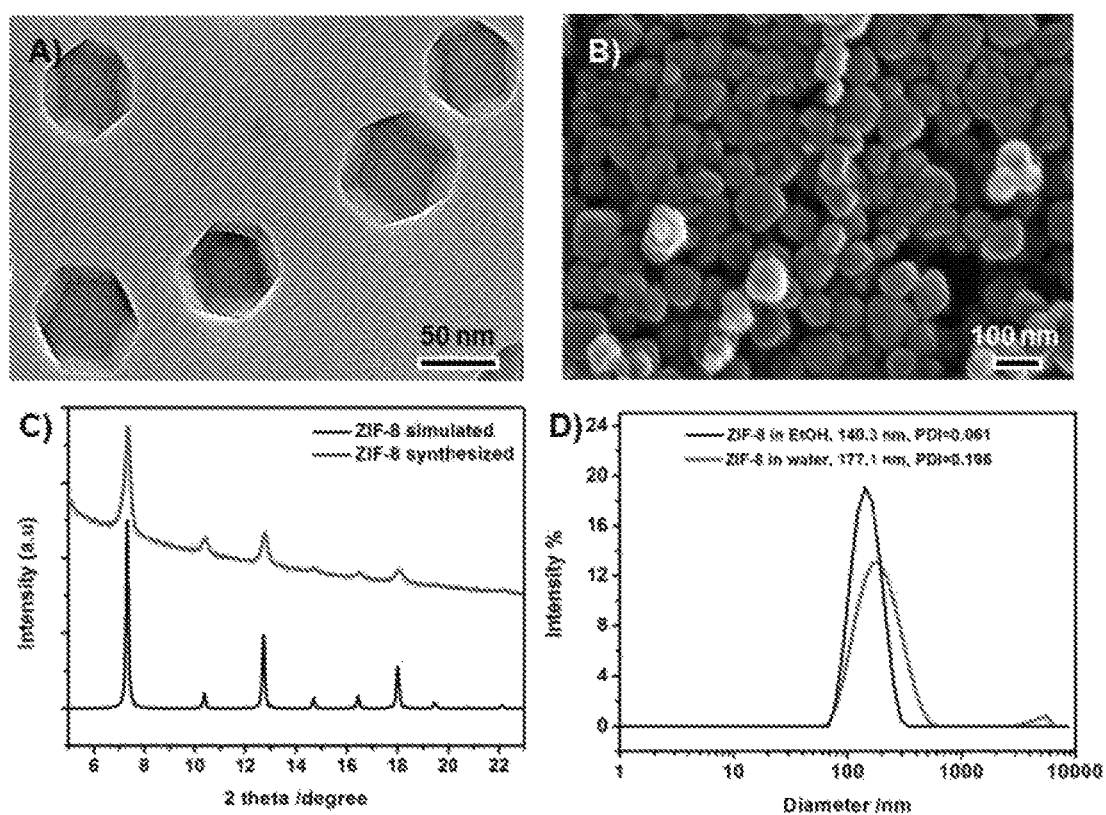
FIGS. 11A-D. TEM (A) and SEM image (B) of ZIF-8 NPs; Wide PXRD patterns of the simulated ZIF-8, and as-synthesized ZIF-8 (C); DLS data of the as-synthesized ZIF-8 NPs in water or EtOH (D).
Figure 12:
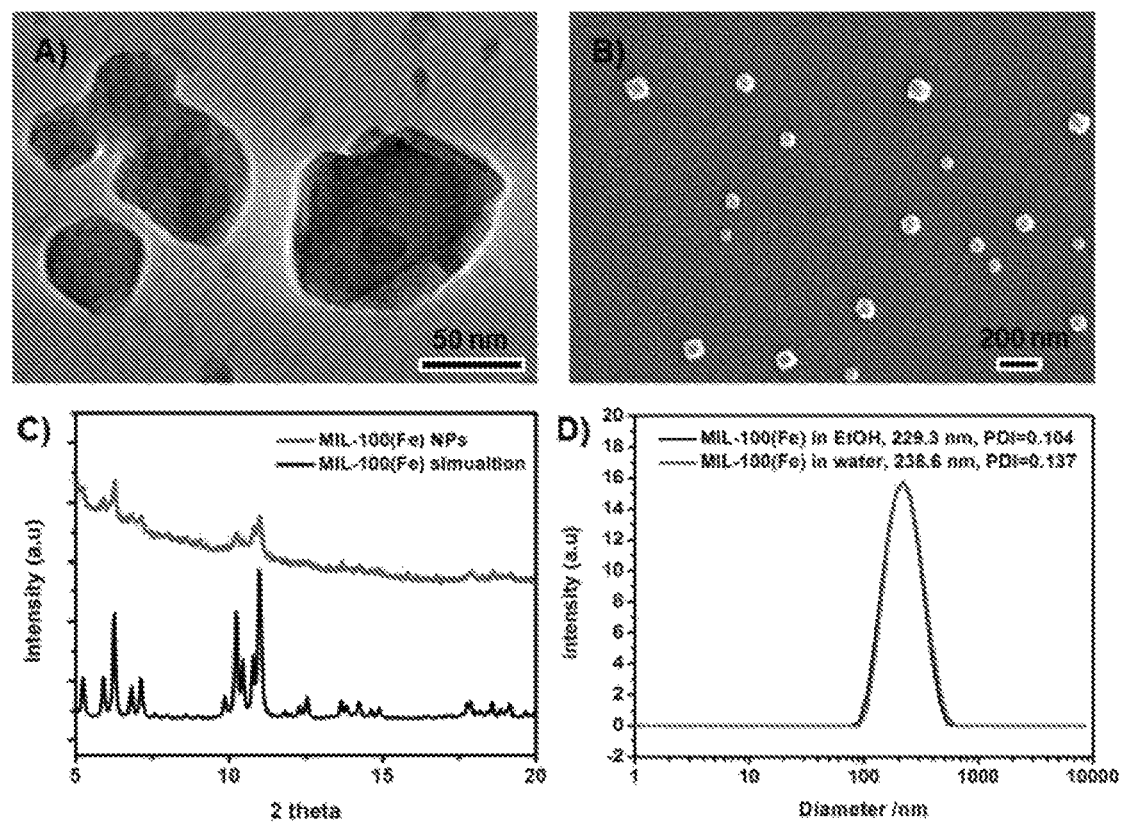
FIGS. 12A-D. TEM (A) and SEM image (B) of MIL-100 (Fe) NPs; Wide PXRD patterns of the simulated MIL-100 (Fe), and as-synthesized MIL-100(Fe) (C); DLS data of the as-synthesized MIL-100(Fe) NPs in water or EtOH (D).
Figure 13:
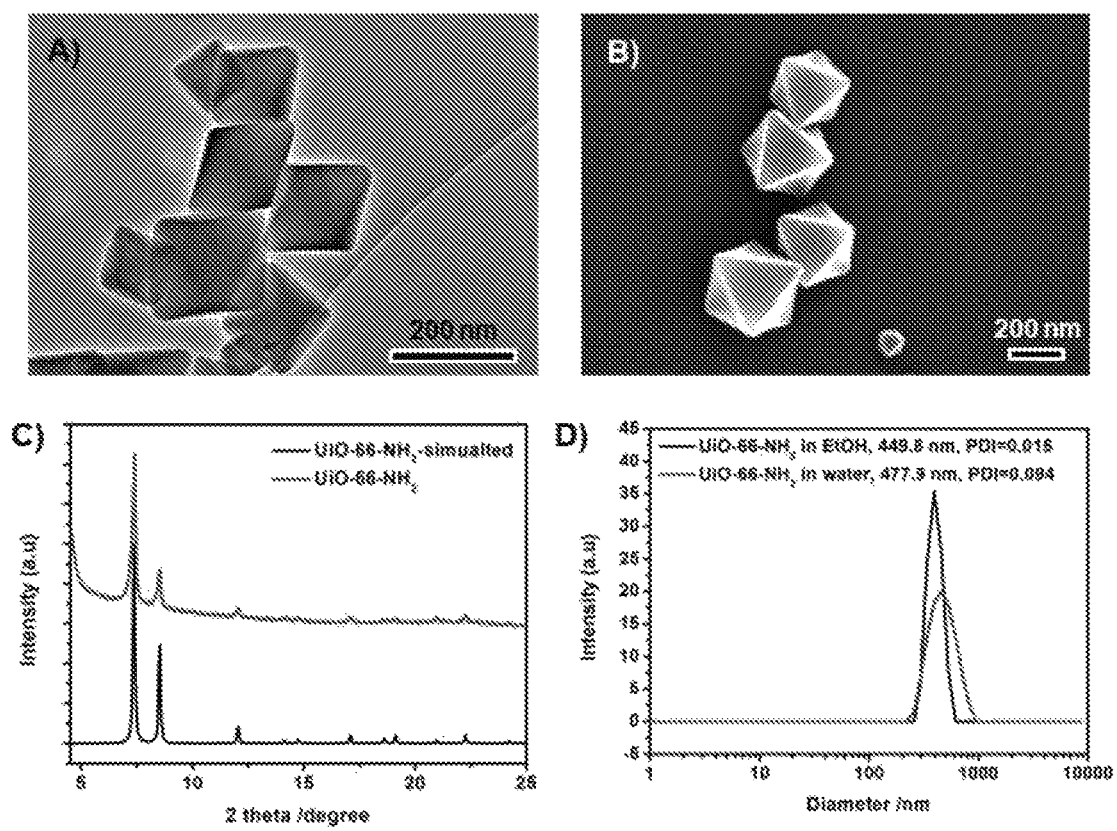
FIGS. 13A-D. TEM (A) and SEM (B) image of UiO66-$NH_2$ MOF NPs; Wide PXRD patterns of the simulated UiO66-$NH_2$, and as-synthesized UiO66-$NH_2$ (C); DLS data of the as-synthesized UiO66-$NH_2$ in water or EtOH (D).
Figure 14:
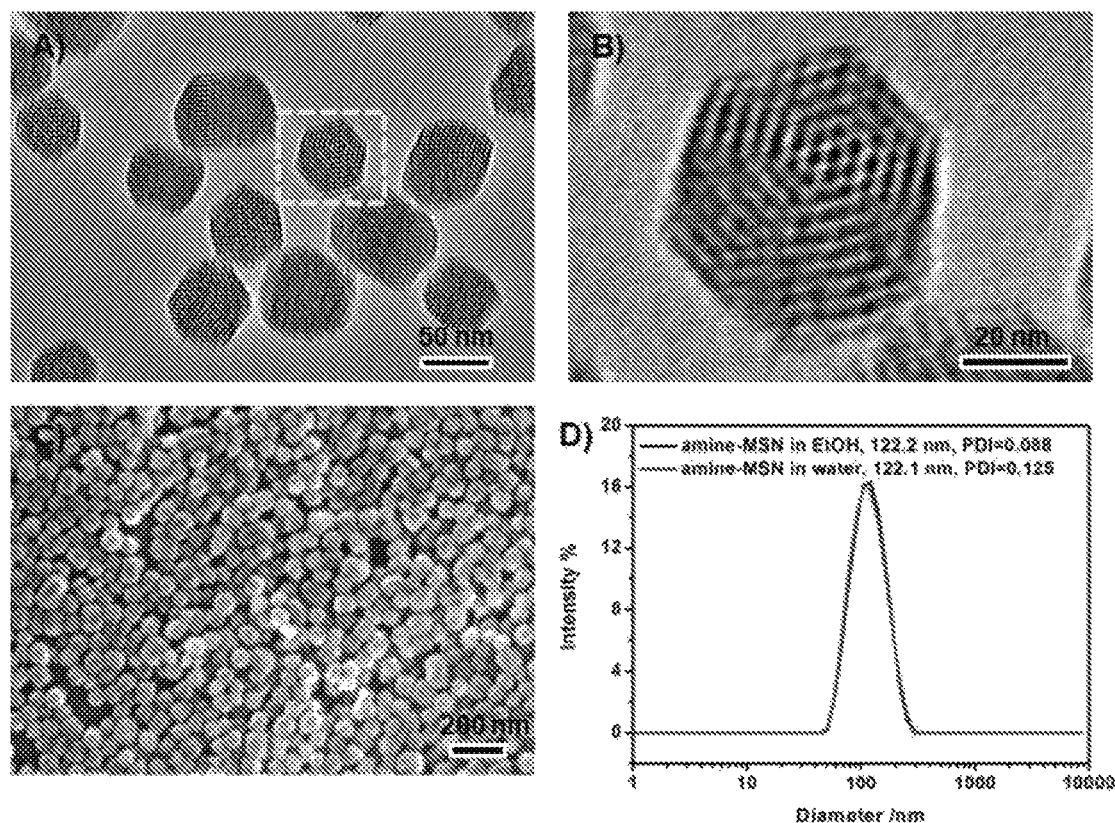
FIGS. 14A-D. TEM (A-B) and SEM (C) images of amine-functionalized mesoporous silica NPs; DLS data of amine-functionalized mesoporous silica NPs in water or EtOH (D).
Figure 15:
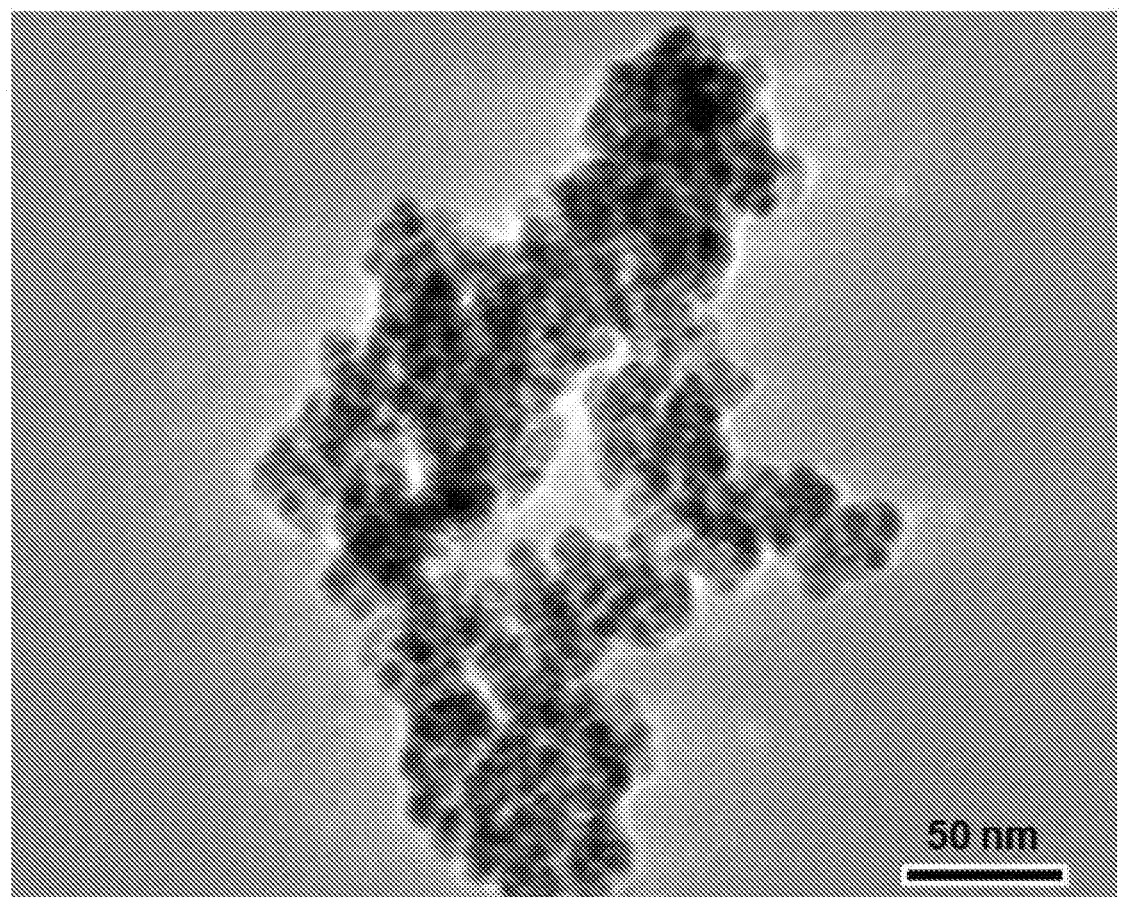
FIG. 15. TEM image of exemplary $Fe_3O_4$ NPs.

As a first demonstration of the SupraCell concept, individual HeLa cells were encapsulated within ZIF-8 (zeolitic imidazolate framework-8) metal-organic framework (MOF) NP-based exoskeletons (termed Supra-HeLa Cell-ZIF-8) via the sequential addition of a colloidal ZIF-8 solution and tannic acid to cell suspensions prepared in PBS solution. The ca. 50 nm diameter, well-defined rhombicdodecahedral shape, and cubic $I\bar{4}3$ m group symmetry of water borne colloidal ZIF-8 NPs were confirmed using transmission electron microscopy (TEM) and wide-angle X-ray diffraction (XRD) analyses (FIGS. 1D and 1F). Only thirty seconds of incubation were necessary to freeze the cellular internalization of the ZIF-8 nanobuilding blocks via tannic acid-mediated interparticle binding due to strong-multivalent metal-phenolic complexation (Ejima et al., 2013). The formation of the NP-based exoskeleton surrounding the HeLa cells is driven by the multitude of NP-cell membrane interaction and is self-limiting due to steric occlusion of membrane binding sites. The NP exoskeletons were directly visualized using bright field and scanning electron microscopy (SEM) imaging of both normal cells and SupraCells (FIGS. 1C, 1E and 5). Fourier-transform infrared spectroscopy performed on Supra-HeLa Cell-ZIF-8 confirmed the coordination of tannic acid to zinc open sites on the ZIF-8 surface, as evidenced by the characteristic peaks at 1179 and 994 $cm^{-1}$ assigned to the vibration of C=N and C—N in the imidazole ring of ZIF-8 and 1083 $cm^{-1}$ assigned to the stretching vibration of C—O in tannic acid (FIG. 6), respectively. Analyzing nearly one hundred SupraCells on SEM images strongly supported the fact that all individual HeLa cells had homogeneous conformal exoskeletons (FIG. 1G; FIG. 7), as further confirmed by confocal scanning laser microscopy (CLSM) of a red fluorescently-labeled ZIF-8-NP-based exoskeleton (FIG. 1H) where a coherent, conformal ZIF-8-NP layer encapsulating the HeLa cell was observed. Wide-angle XRD (FIG. 1F) along with energy-dispersive X-ray (EDX) spectroscopy mapping of zinc, carbon, and oxygen atoms (FIG. 8) confirmed preservation of the structural and chemical integrity of the ZIF-8-NP exoskeletons. The generality of the NP-based exoskeleton paradigm was then demonstrated on other mammalian cell lines including A549 cells (adenocarcinomic human alveolar basal epithelial cell) and HL-60 cells (human promyelocytic leukemia cells), both yielding SupraCells-ZIF-8 with continuous exoskeletons (FIGS. 9-10).

Figure 16:
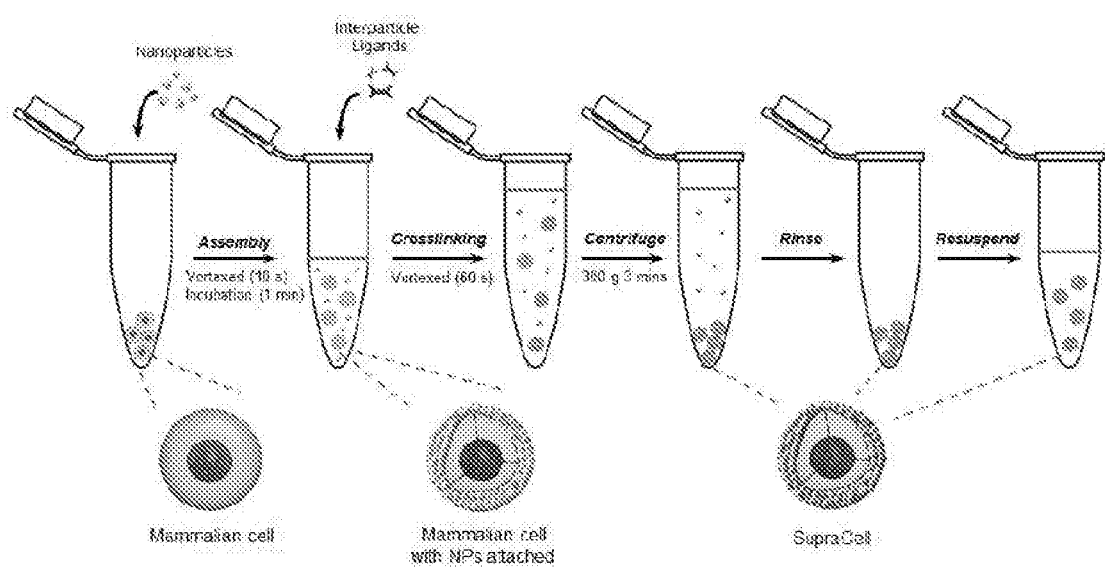
FIG. 16. Schematic illustration of the fabrication of exemplary Supercells.
Figure 17:
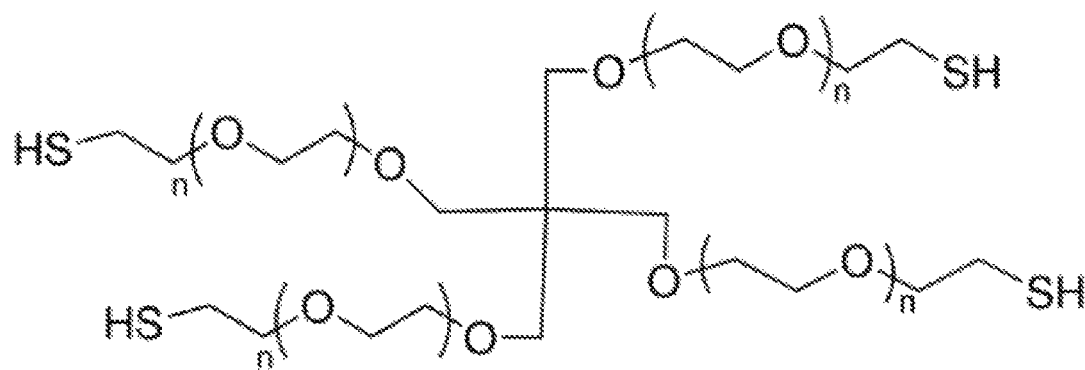
FIG. 17. The molecular structure of 4-arm-PEG5K-SH.
Figure 22:
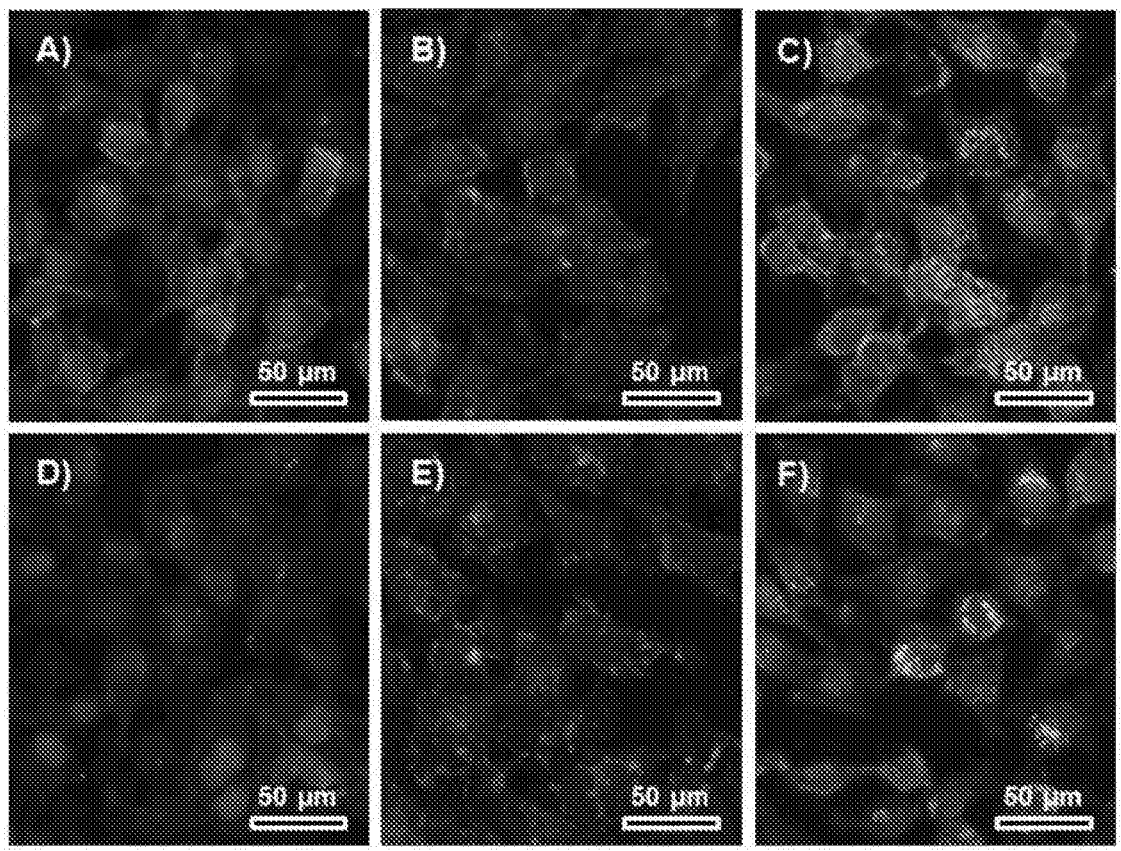

To demonstrate the versatility of the SupraCell approach, different nanobuilding blocks were employed for multifunction integration. Additional types of MOF NPs (e.g., MIL-100(Fe), UiO-66-NH2, and MET-3-Fe) with different framework-related functionalities (e.g., sensing or conductivity), mesoporous silica NPs and dye-labeled MSNs, as well as magnetic $Fe_3O_4$ NPs were selected for SupraCell exoskeleton formation experiments employing HeLa cells. For every case, successful preparation of NP exoskeletons was confirmed by a panel of analyses including XRD, SEM, TEM, and dynamic light scattering (DLS) (FIGS. 11-15). For the different NP systems, different inter-particle ligand chemistries were used to form the exoskeletons via inter-nanoparticle binding at the cellular interface, namely, tannic acid for MOF systems based on metal-phenolic interaction, 1,4-benzendiboronic acid for phenol-functionalized MSNs or $Fe_3O_4$, exploiting boronate-phenolic interactions, and 4-arm-PEG5K-SH for thiol-modified MSNs through thiol-thiol reactions (FIG. 16) for SupraCell syntheses to other cell lines (see below). Based on characterization by SEM, optical microscopy, and CLSM, all Supracell constructs depicted continuous, conformal NP-based exoskeletons (FIGS. 17-20). As a control without inter-nanoparticle cross-linking, the NPs were quickly (<5 min) physical adsorbed onto the cellular surface and then taken up by the cell, accumulating around the nucleus (FIG. 22). The robustness and versatility of this approach using various mammalian cell lines and nanobuilding blocks suggests that a vast library of SupraCells can now be designed for a wide array of scientific investigations.

Figure 23:
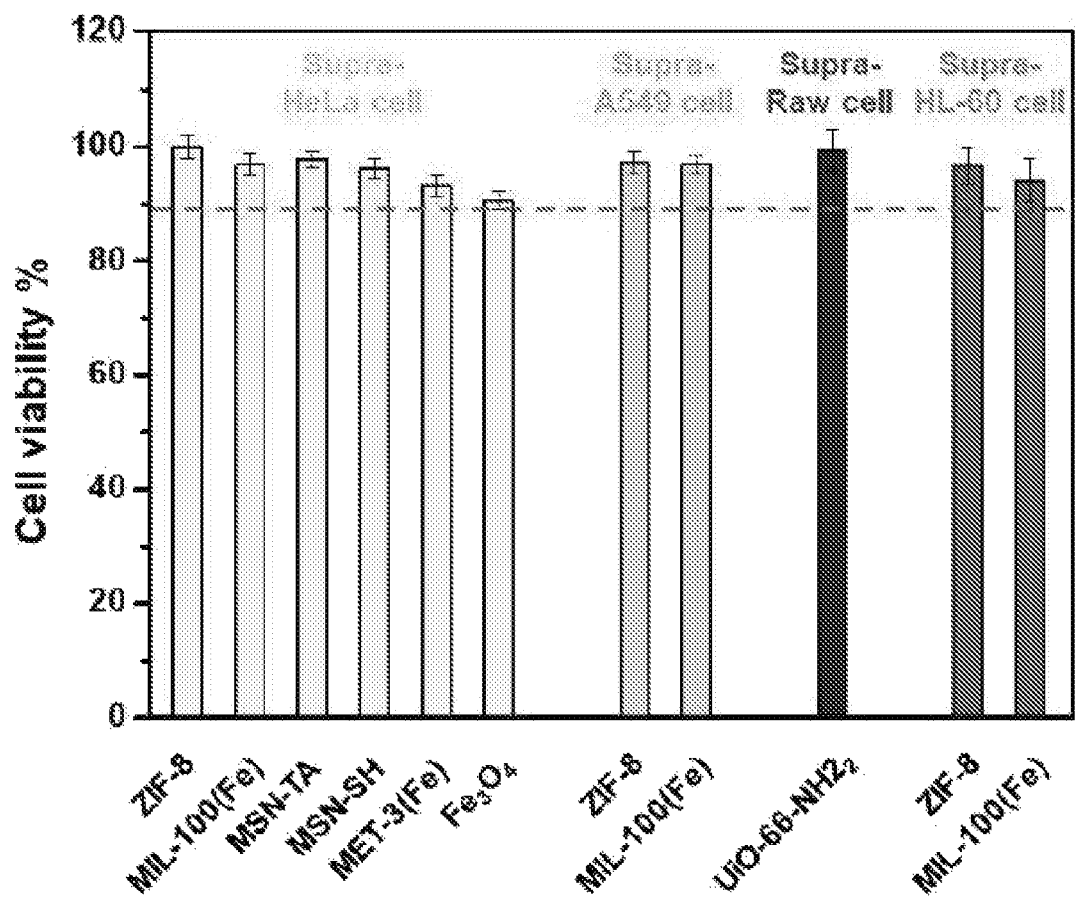
FIG. 23. Cell viability of various exemplary SupraCells after NPs coating.
Figure 24:
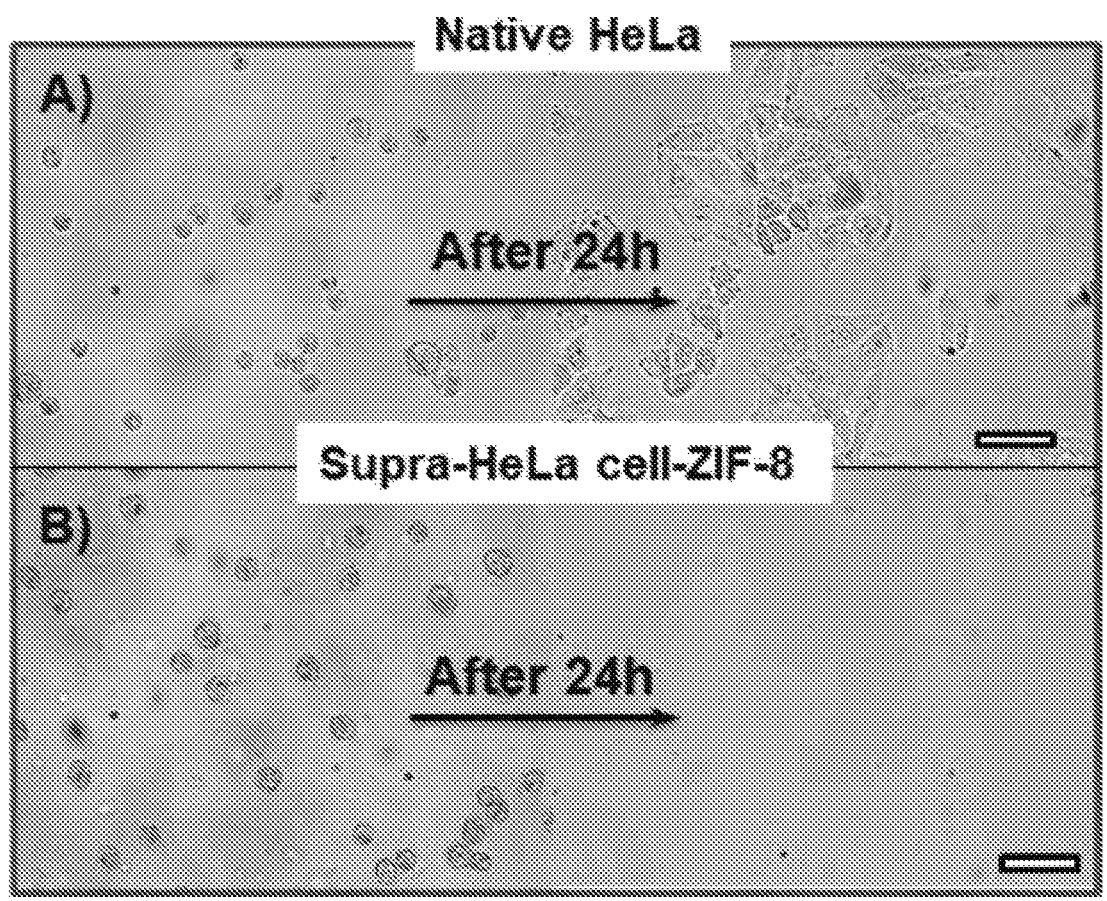
FIGS. 24A-B. Optical microscopy images of native HeLa cells (A) and Supra-HeLa cell-ZIF-8 (B) in culture flasks after cell seeding and 24 hours culture. Scale bar: 50 μm.

Implicit in the Supracell concept of protecting cells within NP exoskeletons is preservation of cellular function. In order to assess the cytocompatibility of the Supracell process, the viabilities of HeLa-, A549-, Raw 264.7-, and HL-60-based Supracell suspensions were determined using the CellTiter-Glo® 2.0 cell viability kit. All the SupraCells exhibited cell viabilities of over 90% after NPs coating (FIG. 23), indicating negligible cytotoxicity of the exoskeleton formation process. Extending the incubation times up to 72 hours reduced the viability in an identical manner to that of native HeLa cells maintained in suspension (FIG. 2A). Here it should be noted that normally adherent cells maintained in suspension lose their cell-extracellular matrix (ECM) interactions and undergo a process of anoikis where the cell cycle is arrested and a specific form of caspase-mediated programmed cell death (apoptosis) occurs (Guadamillas et al., 2011).

Figure 25:
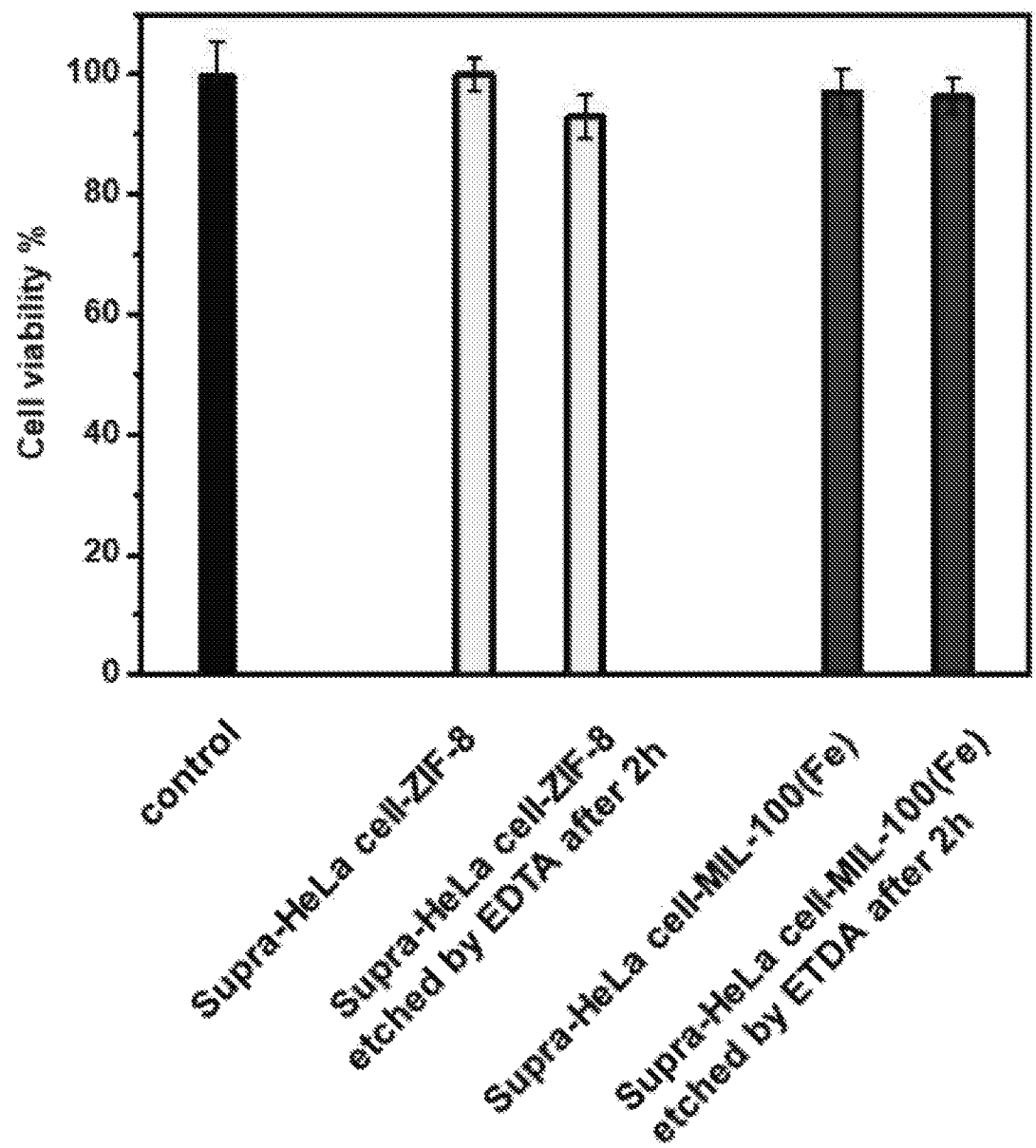
FIG. 25. Cell viability of SupraCell-ZIF-8/MIL-100(Fe) after the treatment of EDTA for 30 minutes to remove the MOF shell.
Figure 26:
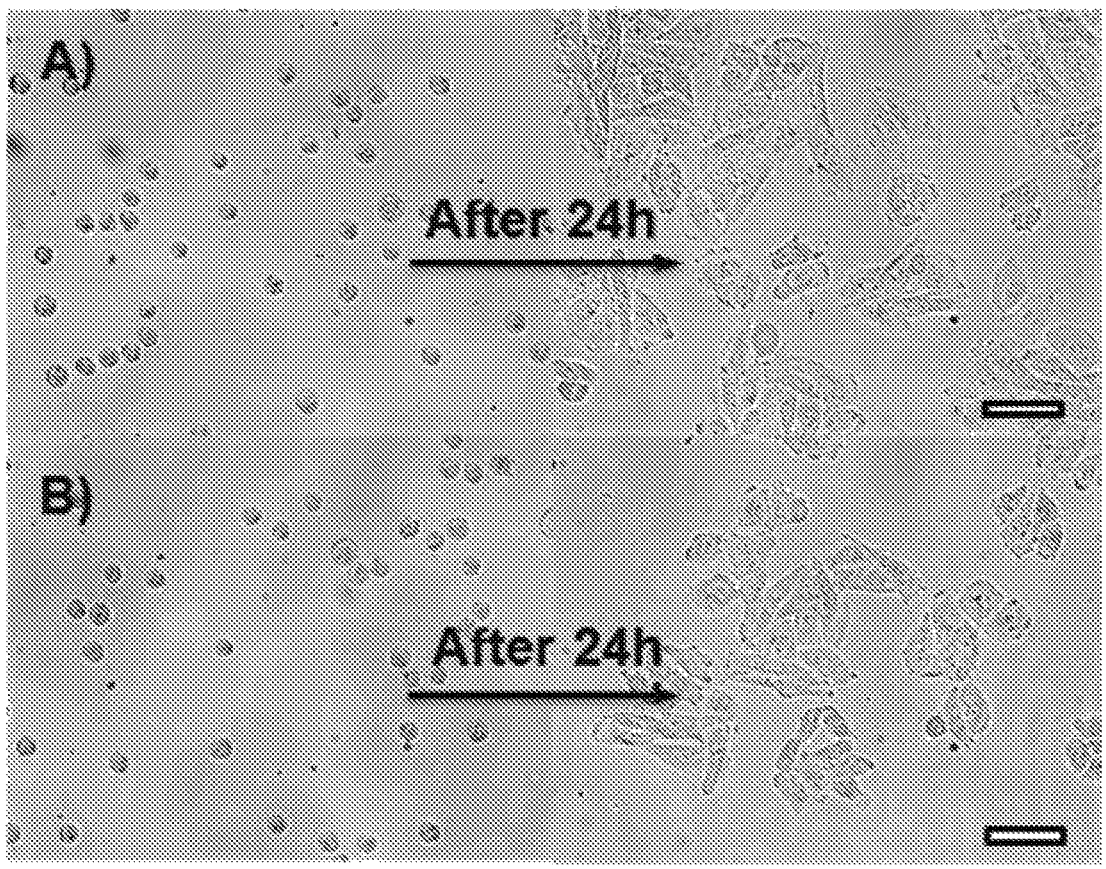
FIGS. 26A-B. Supra-HeLa cell-ZIF-8 attachment and proliferation after the removal of ZIF-8 shell at the encapsulation time of 2 hours (A) and 24 hours (B). Scale bar: 50 μm FIGS. 27A-F. The proliferation of native HeLa cell (A-C) and Supra-HeLa cell-ZIF-8 after shell removal after the encapsulation for 24 hours (D-F) at different time intervals: 6 hours, 24 hours, and 72 hours.
Figure 27:
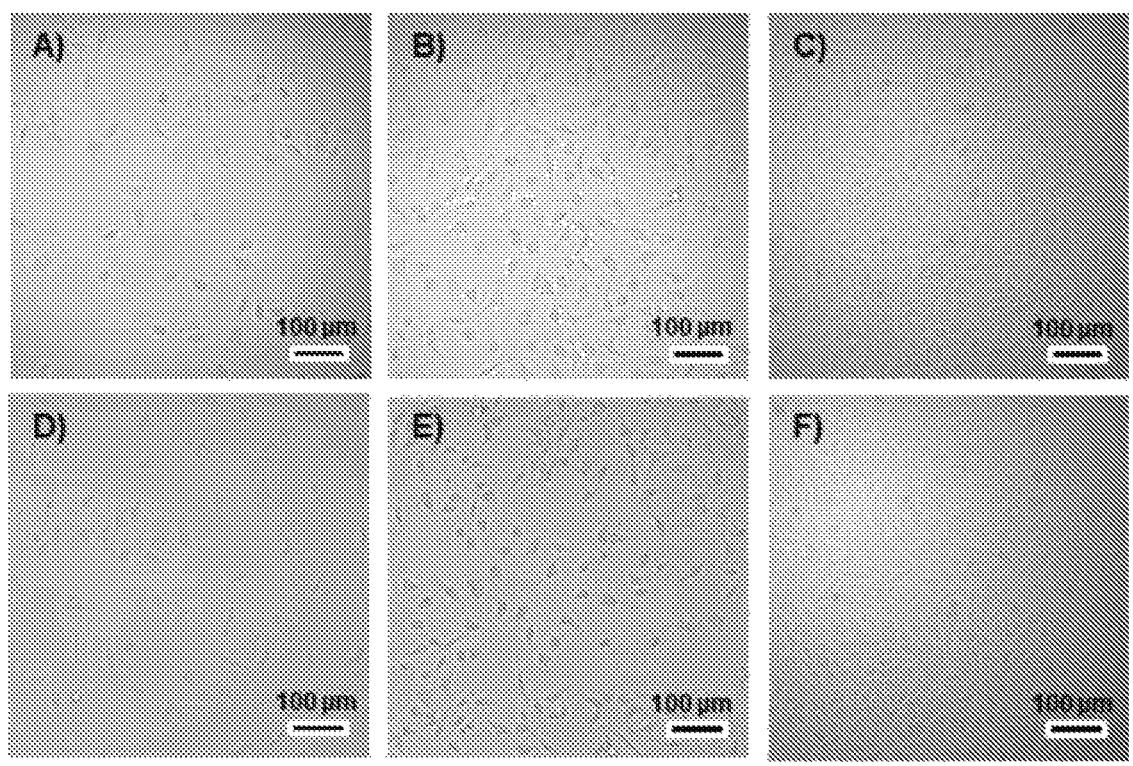
Figure 28:
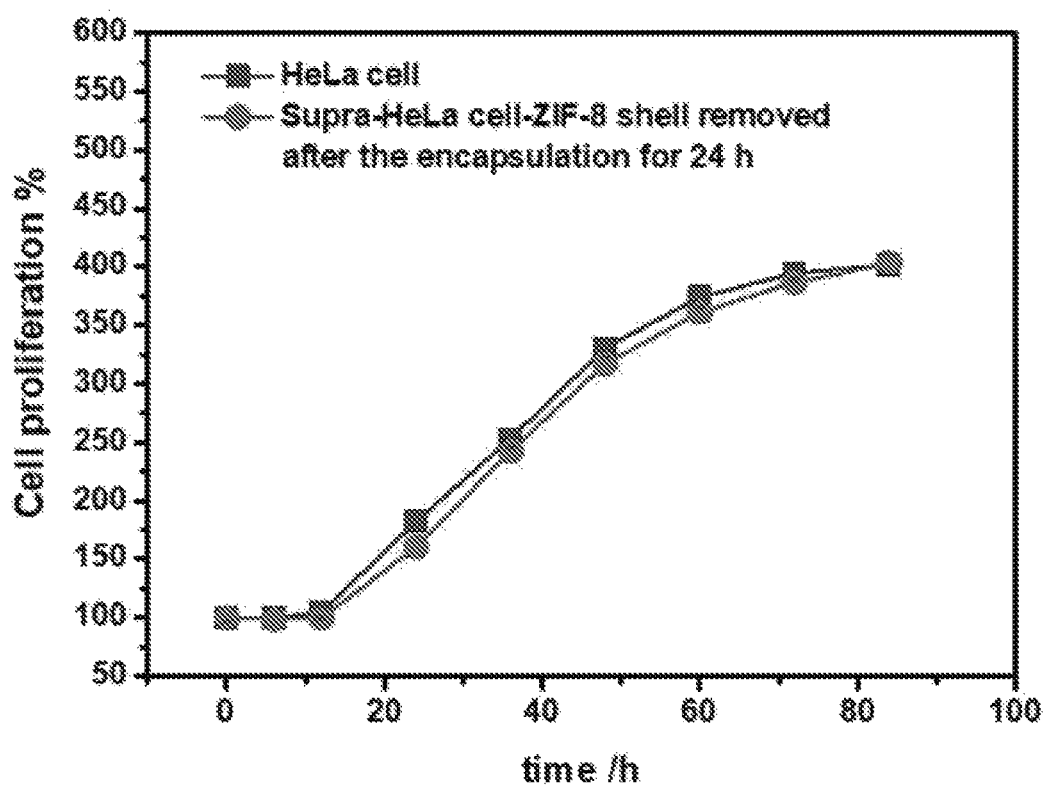
FIG. 28. The cell proliferation rate of native HeLa cell and Supra-HeLa cell-ZIF-8 after shell removal after the encapsulation for 24 hours.
Figure 29:
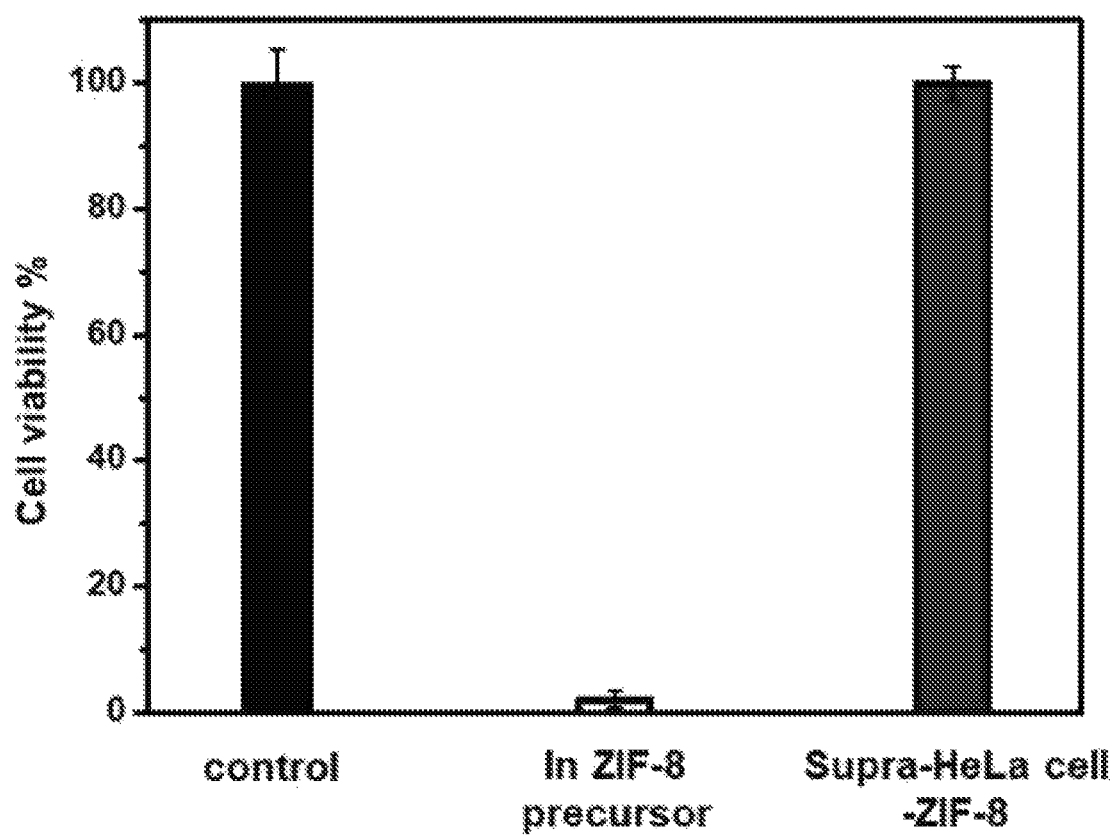
FIG. 29. Cell viability comparison between native HeLa cell, HeLa cell in ZIF-8 precursor solution for 5 minutes, and HeLa cell after ZIF-8 NPs encapsulation.

Having established viability (based on an assay that measures X), the biological behavior of Supracells was examined. The rigidity of the NP exoskeleton, cellular isolation, and obscuration of cell adhesion molecules like integrins would likely conspire to arrest cellular adhesion, spreading, and proliferation. To test this hypothesis, the proliferation of HeLa based SupraCell-ZIF-8 suspensions was tested when introduced to glass substrates under standard culture conditions at time points ranging from 1-24 hours post exoskeleton formation and compared to that of native HeLa cells. As shown in FIG. 27, unlike native HeLa cells, Supracells do not adhere, spread or proliferate. However, based on the reversibility of metal-phenolic complexation (Park et al., 2014), exposure of SupraCell-ZIF-8 to ethylenediaminetetraacetic acid solution (50 mM, pH 5.0) for 30 minutes results in Zn chelation, complete exoskeleton removal, and recovery of native HeLa cell behavior. FIG. 25 shows the formation and removal of ZIF-8 or MIL-100(Fe) exoskeletons had a negligible effect on viability compared to native control cells. As shown in FIG. 25, after ZIF-8 exoskeleton removal HeLa cells adhere, spread, and proliferate under cell culture conditions. Analysis of proliferation rates indicate reversed Supracells have almost the same proliferation rate compared to native cells (FIGS. 27-28). This on-demand exoskeleton formation and degradation capability confers to mammalian cells behaviors normally associated with the germination of natural spores, and unlike the biomineralization approach reported for robust yeast cells (Liang et al., 2016), the NP-based exoskeleton approach is biocompatible even with sensitive mammalian cells. Indeed, rapid mammalian cell death was observed in a control experiment using a MOF biomineralization approach (FIG. 29).

Figure 2:
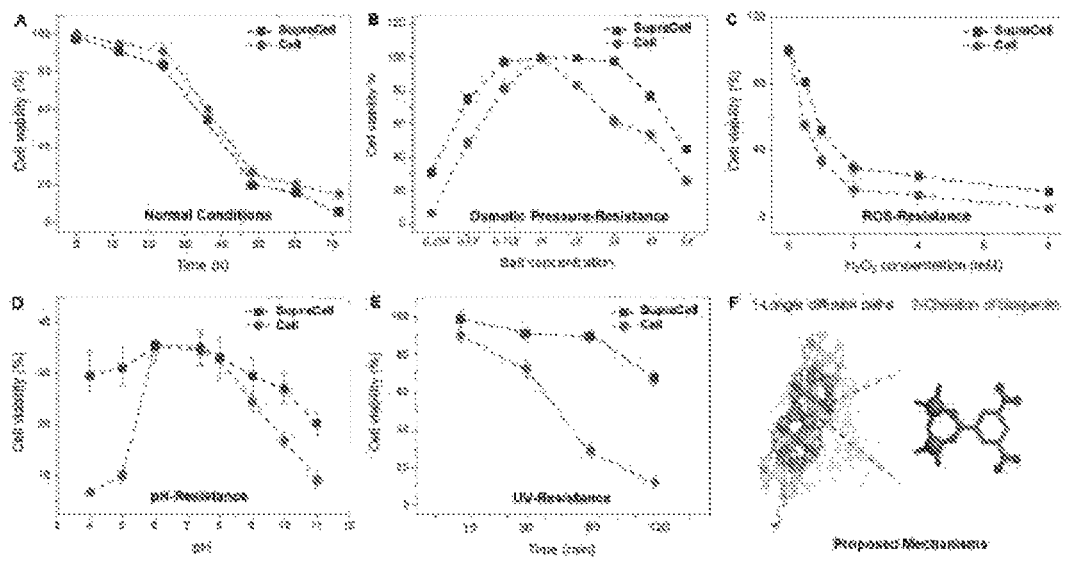
FIGS. 2A-F. Enhanced resistance of exemplary SupraCells against endo- and exogenous stimuli. (A) Viability of HeLa cells versus corresponding SupraCells based on MIL-100(Fe) nanobuilding blocks, in normal conditions. (B) Viability of HeLa cells versus SupraCells as a function of the salt concentration (i.e. osmotic pressure stimulus), (C) $H_2O_2$ concentration (e.g., ROS stimulus), (D) pH, (E) and UV irradiation time (254 nm). (F) Representation of the nanostructure of the NP-based exoskeleton of the SupraCell-MIL-100(Fe) suggesting two proposed mechanisms to account for the enhanced resistances of SupraCells.
Figure 30:
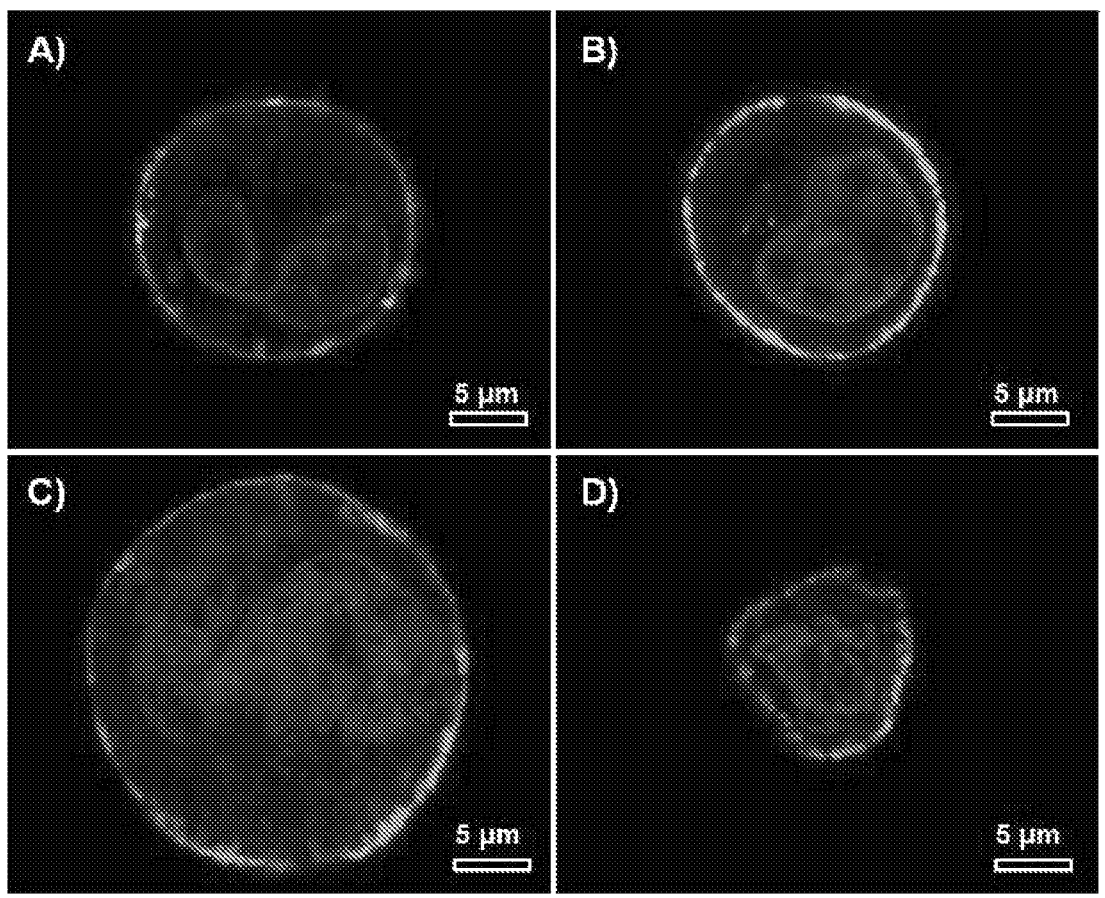
FIGS. 30A-D. Confocal image of HeLa cell in PBS (1×) solution (A) and Supra-HeLa cell-MIL-100(Fe) in different PBS solution: 1× (B), 0.25× (C), and 5× (D).

In order to demonstrate how the SupraCell exoskeletons protect the cells against external stressors, SupraCell-MIL-100(Fe) was exposed to various harsh treatments including osmotic pressure, pH, reactive oxygen species (ROS), and UV conditions (FIG. 2). First, upon exposure to varying ionic strength solutions (expressed as xPBS, where 1xPBS is isotonic with living cells) native HeLa cells show 100% viability at 1xPBS but greatly reduced viability at lower or higher osmotic stress and only 6.4% and 26.0% viability at 0.25xPBS and 5xPBS, respectively. In comparison, Supra-Cell-MIL-100(Fe) shows nearly 100% viability from 0.75x PBS to 3xPBS and cell viabilities of 31.0% and 44.7%, at 0.25xPBS and 5xPBS, respectively. In mammalian cells, hypertonic conditions result in water expulsion from cells and cell shrinkage, while hypotonic conditions result in the reverse process and cell swelling both processes resulting in rapid cell lysis for conditions other than isotonic. The enhanced mechanical stiffness and membrane reinforcement provided by the supracell exoskeleton resists both cellular shrinkage and swelling processes thereby greatly reducing cell lysis under hypotonic and hypertonic conditions. As an example, FIG. 30 shows fluorescent microscopy images of native cells and SupraCell-MIL-100(Fe) maintained in 1xPBS (actin cytoskeleton stained green and nucleus stained blue) and SupraCell-MIL-100(Fe) maintained in 0.25x or 5xPBS, conditions under which native cells show dramatic lysis (disallowing cellular imaging). Remarkably, the supracell exoskeletons can accommodate substantial hypotonic-induced swelling and hypertonic-induced shrinkage while largely avoiding lysis. For example, a hypotonic or hypertonic solution may be employed to store cells or for injection purposes. The use of supercells allows for tolerance to such a hypotonic or hypertonic solution.

Second, ROS can cause oxidative damage and produce adverse modification to cellular components (e.g. lipids, and DNA) (Nel et al., 2006). As shown in FIG. 2C, the viabilities of Supracells paralleled but were statistically greater than those of native HeLa cells in the presence of increasing hydrogen peroxide ($H_2O_2$) concentrations. The increased ROS-resistance of Supracells may be associated with the unique antioxidant properties of tannic acid in the exoskeleton nanostructure (Evans et al., 1997). For example, if diagnostic or therapeutic cells are to be administered before radiation therapy (which generates ROS that can damage cells), the exoskeleton can prevent or inhibit ROS damage.

Third, the viability of SupraCells was tested over the pH range 4-11 as it is understood that altered acid-base balance and extreme pH ranges can disrupt cell metabolic processes and cause irreversible cell damage (Parks et al., 2013). As shown in FIG. 2D, pH values below 6.0 or greater than 8.0 led to an abrupt decrease of viability for native HeLa cells, whereas SupraCells showed increased resistance toward pH variation and exhibited two-fold and three-fold higher viabilities at pH 11 and 4, respectively. This pH resistance is attributed to the ion chelating effect and longer-diffusion times resulting from the porous exoskeleton framework (FIG. 2F) (Furukawa et al., 2013). For example, a solution with a pH below 6.0 or greater than 8.0 may be employed to store cells or for injection purposes. The use of supercells allows for tolerance to different pH solutions.

Figure 32:
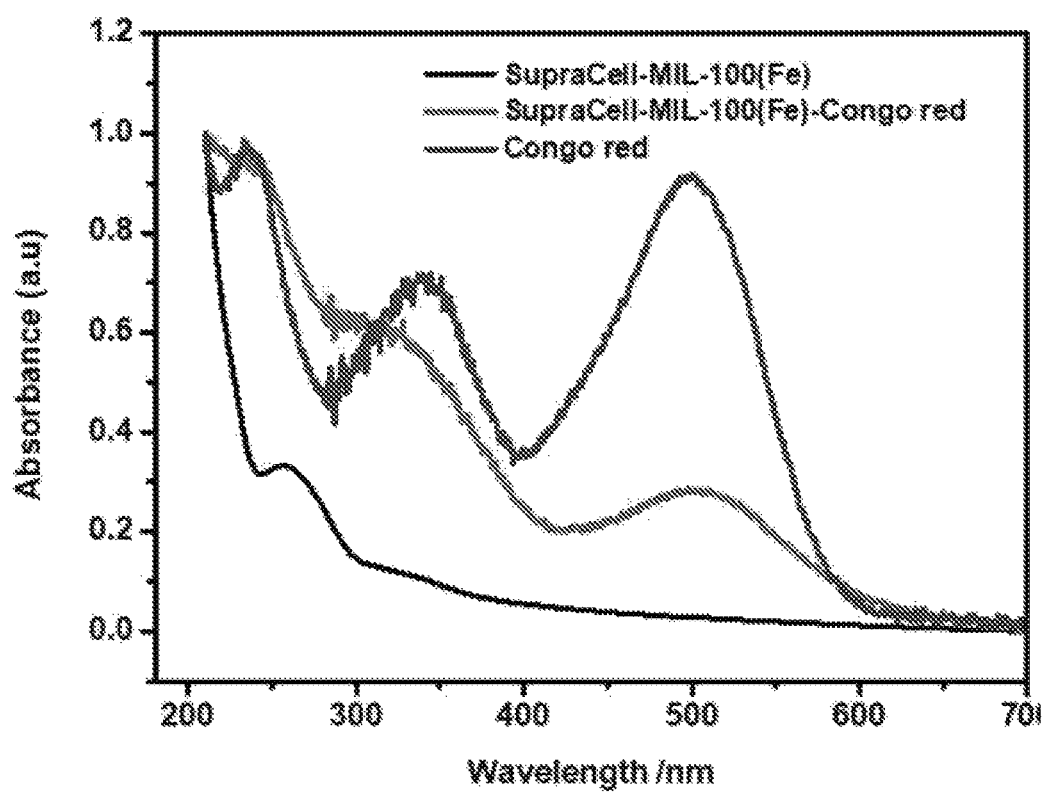
FIG. 32. UV-Vis spectra of Congo red and SupraCell-MIL-100(Fe) based on HeLa cells with or without Congo red dye loading in PBS (1×) solution.
Figure 33:
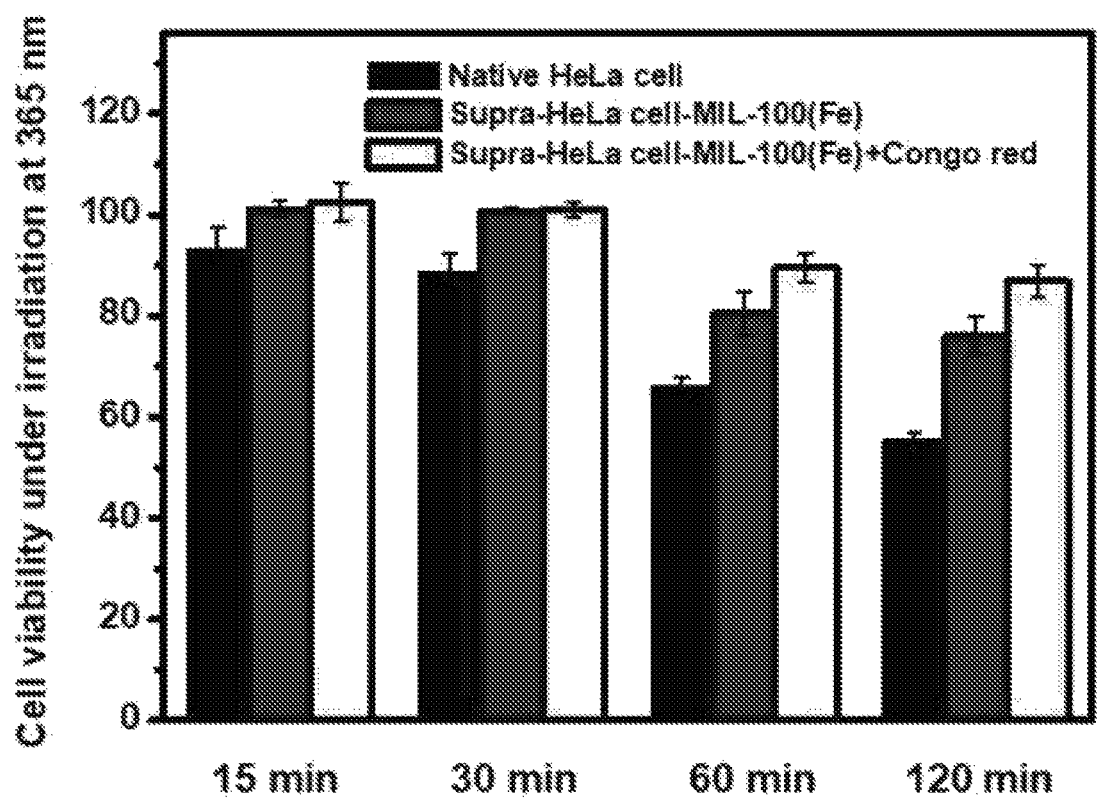
FIG. 33. Cell viability of native HeLa cell and Supra-HeLa 100(Fe) under UV irradiation (365 nm, 4W) for different incubation times.

Finally, the resistance of Supracells to UV irradiation ($\lambda$=254 nm, 4W) in comparison to native mammalian cells was determined. As expected, UV exposure caused a sharp decline in the survival of native cells after 60 minutes, resulting in about 30% survival (Talalay et al., 2007), whereas SupraCells remained largely unaffected after the same exposure time (FIG. 2E and FIG. 30). After two hours of UV exposure, the viability of Supracells was over six times higher than the native cells. The UV resistance was attributed to the high UV-absorption coefficient of the MIL-100(Fe)-based SupraCell exoskeletons over the wavelength range 200-300 nm (FIG. 32). Furthermore, the intrinsic porosity of MIL-100(Fe) enables loading of UV-absorbing dyes (e.g. Congo red) in the exoskeleton further enhancing the protection of Supracell-MIL-100 against UV irradiation (Congo red-loaded Supracell-MIL-100(Fe) Supracells exhibited 15% greater viability upon exposure to 365 nm UV light for 120 minutes compared to unloaded Supracells) (FIG. 33). The ability to load molecular cargos into the MOF exoskeleton opens vast possibilities to tune the properties of SupraCells.

Figure 3:
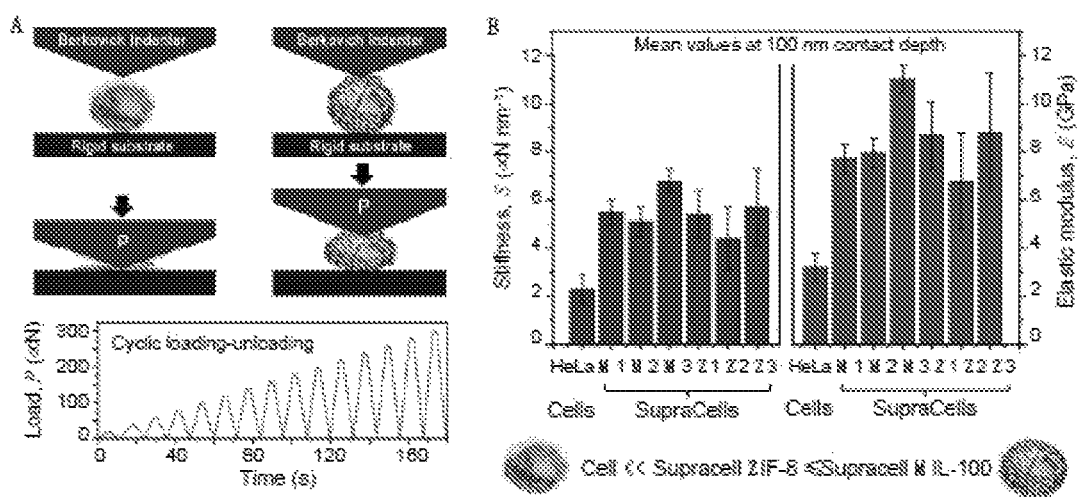
FIGS. 3A-B. Enhanced mechanical resistance of exemplary SupraCells. (A) Representation of the mechanical resistance test set-up involving the movable Berkovich Intender imposing a P load onto cells (left) and SupraCells (right) using a cyclic loading-unloading function. (B) Stiffness and elastic modulus of HeLa cells and SupraCells MIL-100 (M1-M3 associated with P1-P3 loads) and ZIF-8 (Z1-Z3 associated with P1-P3 loads).
Figure 31:
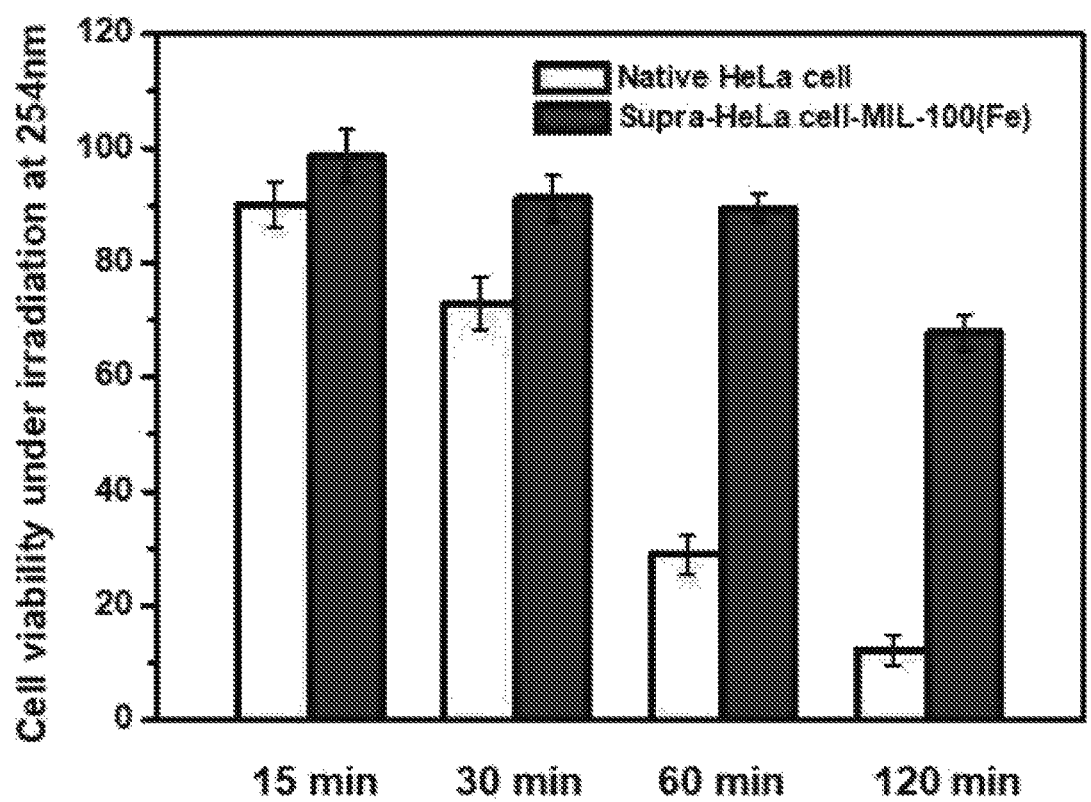
FIG. 31. Cell viability of native HeLa cell and Supra-HeLa 100(Fe) under UV irradiation (254 nm, 4W) for different incubation times.
Figure 34:
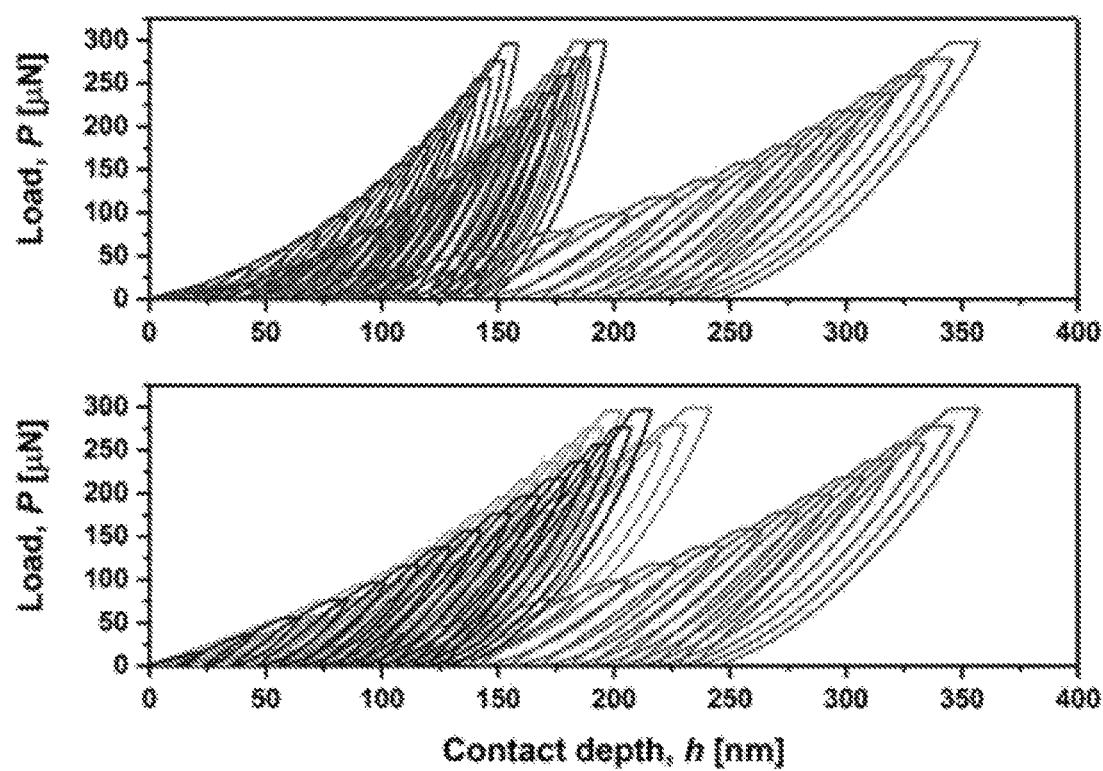
FIG. 34. Loading-unloading curves for native HeLa cells and Supra-HeLa cell-ZIF-8 and Supra-HeLa cell MIL-100 (Fe) with different coating thicknesses.
Figure 35:
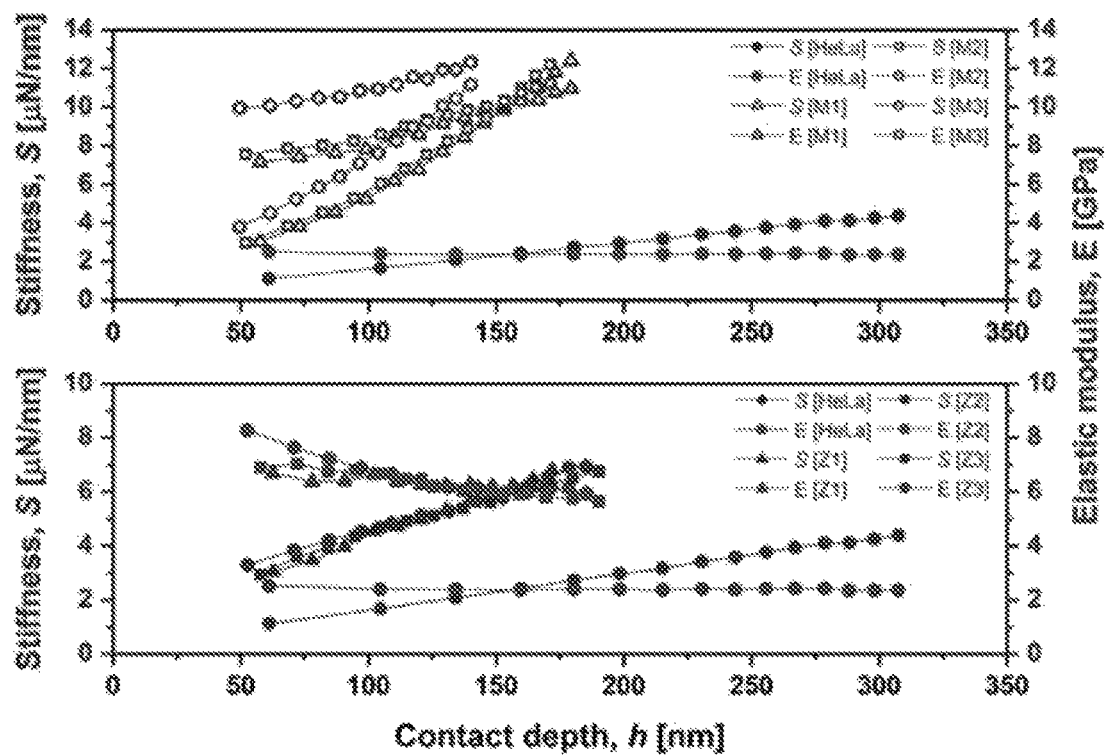
FIG. 35. Stiffness/elastic modulus versus contact depths for Supra-HeLa cell-ZIF-8 and Supra-HeLa cell-MIL-100 (Fe) with different coating thicknesses.
Figure 36:
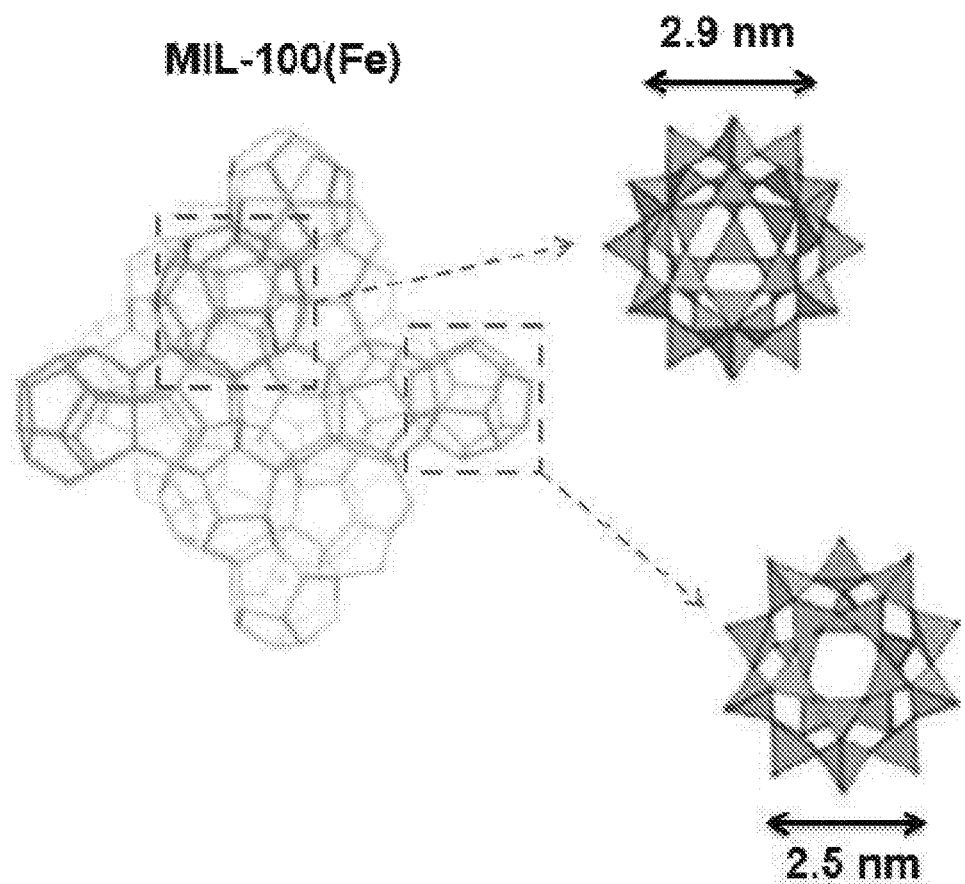
FIG. 36. Schematic illustration of the two mesocages in MIL-100(Fe).

The mechanical properties of MOF-based Supracells were determined by nano-indentation and compared to native cells (see FIG. 3A). HeLa-based SupraCell-ZIF-8 and SupraCell-MIL-100(Fe) samples along with native HeLa cells were subjected to multiple loading-unloading cycles to differing contact depths (FIG. 34). Due to the size and softness of the cell samples, a Berkovich tip with wide contact angle (142.3°) was used. Extracted loading-unloading curves (FIG. 31) revealed that the contact depths for the SupraCells were 50% lower than the contact depths of native HeLa cells, indicating the higher stiffness afforded by the exoskeletons. Slopes of the loading-unloading curves were then used to determine the stiffness S and elastic modulus E as a function of contact depth (FIG. 35). FIG. 3B compares S and E for Supracells and native HeLa cells indented to a contact depth of 100-nm (the approximate thickness of the exoskeleton). Supracells had 2-4× greater stiffness and modulus, explaining in part their greater resistance to osmotic stress. ZIF-8 and MIL-100(Fe)-based Supracells were also found to have differing contact depth dependencies of their elastic moduli (FIG. 34), whereby, MIL-100(Fe) is a flexible MOF that can exhibit densification under applied pressure while ZIF-8-based SupraCells are not based on flexible nanostructures (Horcajada et al., 2007).

Figure 4:
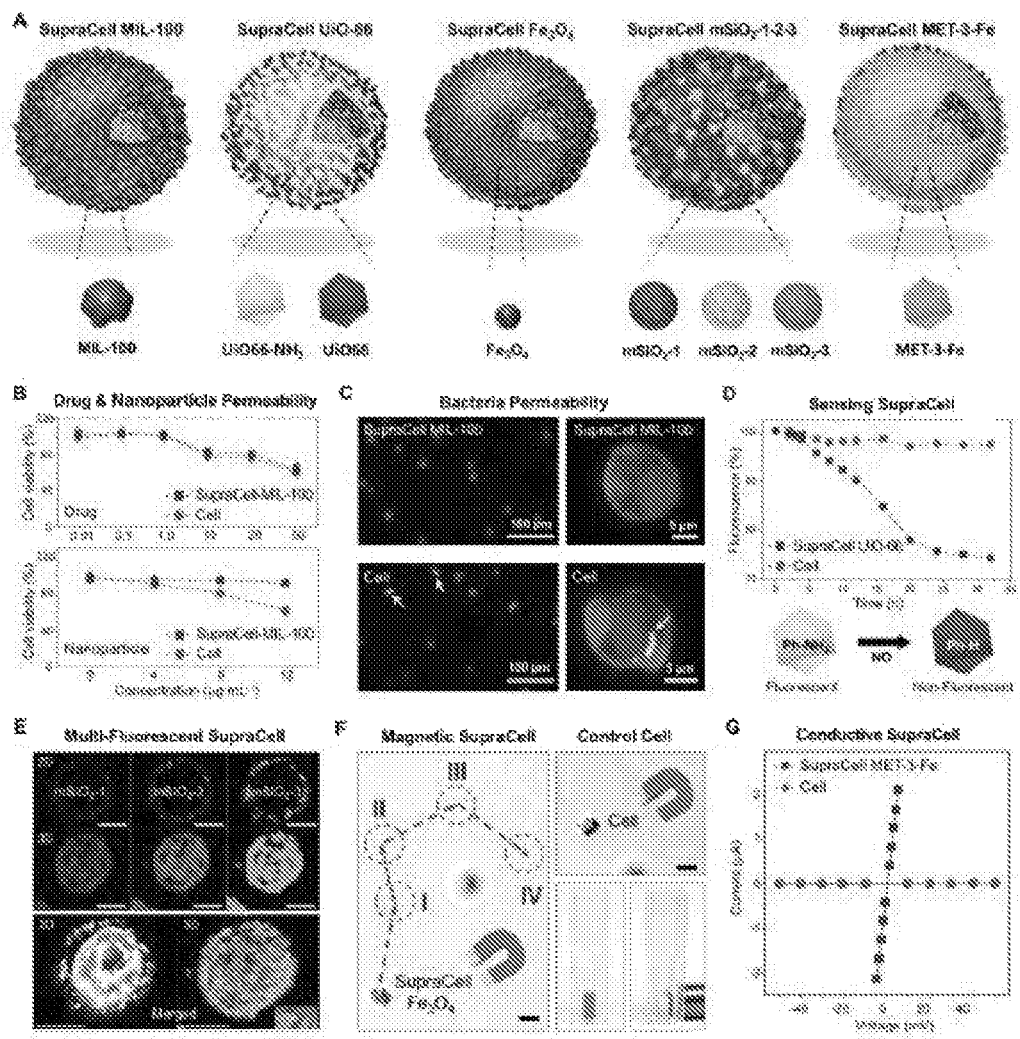
FIGS. 4A-G. Exemplary SupraCell-properties based on modular functional NP-based exoskeletons. (A) Representation of various SupraCells characterized by one or more nanobuilding block type. (B-C) Size-selective permeability studies of SupraCell MIL-100 involving (B) drug (cell viability study) permeations and NPs (cell viability study) and (C) bacteria non-permeation (confocal images show the intracellular green fluorescence of bacteria only in normal cells). (D) Timeline of the fluorescence of cellular NO-sensing SupraCell based on fluorescent UiO-66(Ph-$NH_2$) and non-fluorescent UiO-66(Ph-MOF) nanobuilding blocks. (E) Confocal images of multi-fluorescent SupraCell based on three different fluorescent $mSiO_2$ nanobuilding ($mSiO_2$-1-2-3) blocks. Scale 13 bars: 5 (left) and 2.5 μm (right). (F) Bright-field microscopy images of magnetically-moved SupraCell $Fe_3O_4$ (left) or immobile normal cell (top right). Photographs of a dispersion of SupraCells before (left) and after (right) placing a magnet on its side. (G) Current-voltage plot demonstrating the conductivity imparted to SupraCells via MET-3-Fe MOF NP-based exoskeletons.
Figure 37:
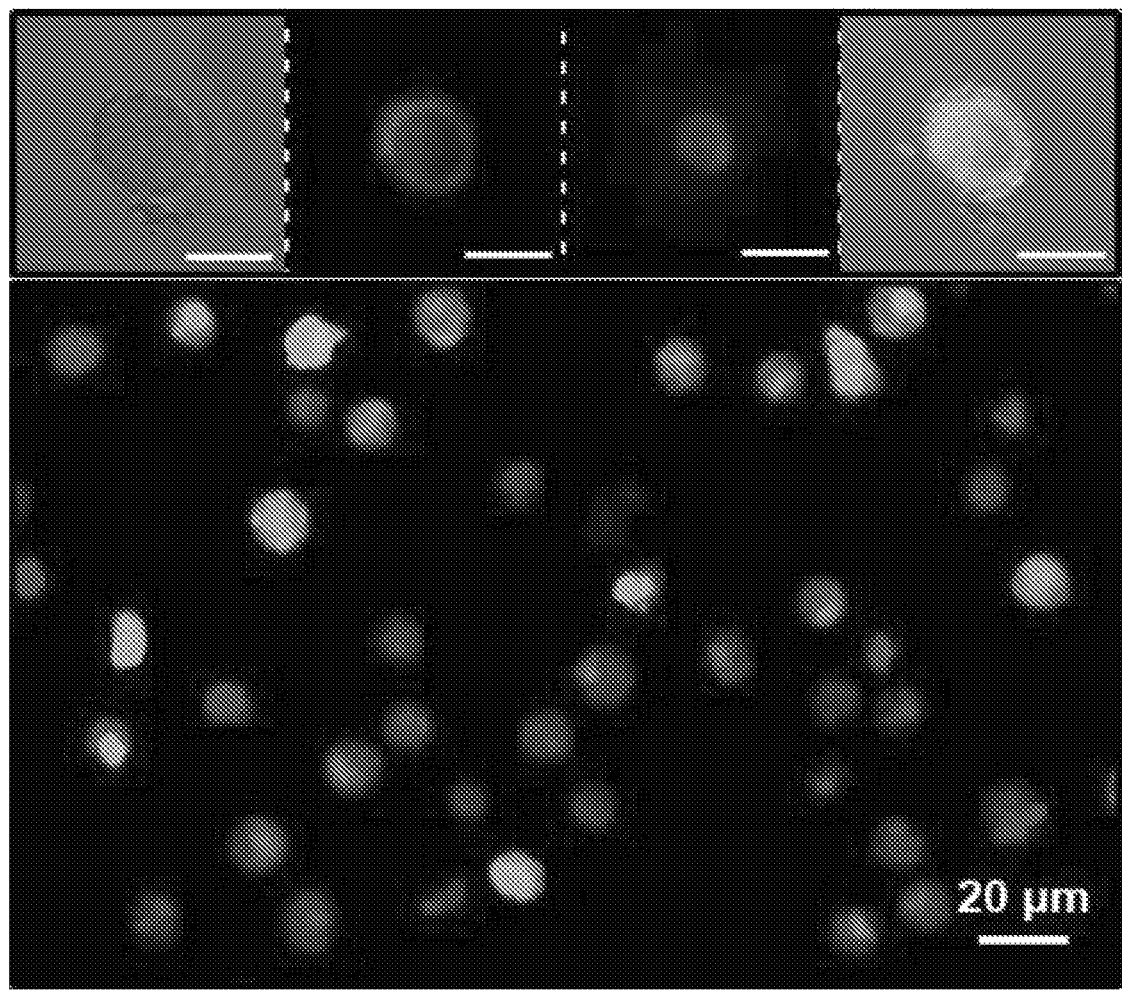
FIG. 37. The uptake of green fluorescent sugar (2-NBDG) in SupraCell-MIL-100(Fe) based on HeLa cells to show sugar permeability.

As represented in FIG. 4, the Supracell construct can be extended to any number of nanoparticle types and combinations to achieve varied functions. A common function of Supracells is that the uniform and complete encapsulation with various NPs introduces a non-12 native, size-selective permeability to the exoskeleton that can maintain viability (FIG. 22) while serving to protect the cell against certain exogenous molecules, e.g., toxins and pathogens. To demonstrate aspects of size selective permeability, SupraCell-MIL-100(Fe) was selected because, as shown in FIG. 35, it is composed of two connected mesocage networks that act as molecular sieves preventing transport of entities greater than 2.9 nm in kinetic diameter. First, preservation of the normal metabolism in SupraCells was confirmed by the uptake of ca. 0.5 nm diameter fluorescently labeled glucose tracers (2-Deoxy-2-[(7-nitro-2,1,3-benzoxadiazol-4-yl)amino]-D-glucose (2-NBDG)) (FIG. 37). Then, the anticancer drug doxorubicin (diameter about 1.6 nm) or cytotoxic silver (Ag) nanocrystals (diameter about 5.0 nm) were added into the culture medium at different concentrations. As shown in FIG. 4B (top panel), both native cells and Supra-Cells were sensitive to doxorubicin and each exhibited a nearly identical dose response curve. However, native cells but not Supracells were sensitive to Ag NPs—Supracells exhibiting about 100% viability at Ag NP concentrations of 12 μg/mL (FIG. 4B bottom panel). These results established an effective pore size cut-off of the exoskeleton membrane (>5 nm) consistent with the pore size of the MIL-100(Fe). In one embodiment, nanoparticles useful in the exoskeletons have a pore size that <1 nm, <5 nm or <10 nm. The MIL-100(Fe)-based exoskeleton also prevented phagocytosis of GFP-expressing *Salmonella enterica serovar* Typhimurium LT2 bacteria (FIG. 4C). Supracells are thus endowed with a unique semi-permeability allowing nutrient uptake but inhibiting or denying attack by pathogens.

Figure 38:
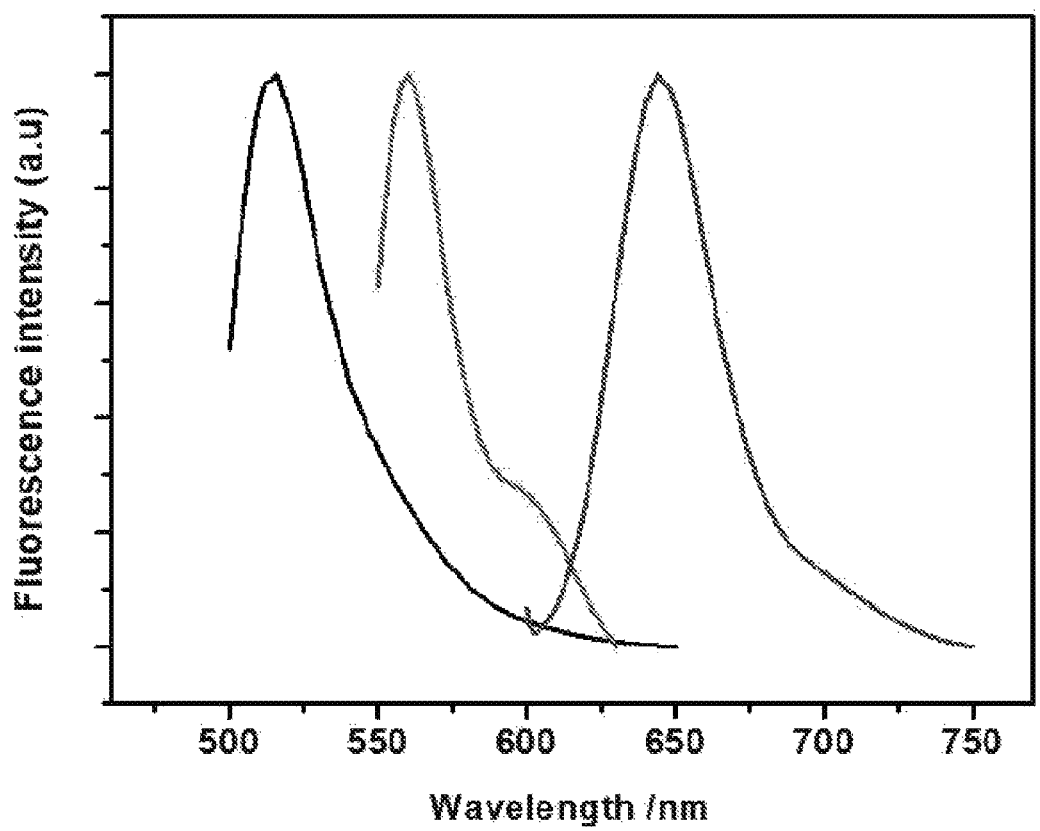
FIG. 38. Fluorescent emission spectra of mesoporous silica NPs functionalized with different fluorescent dyes.
Figure 39:
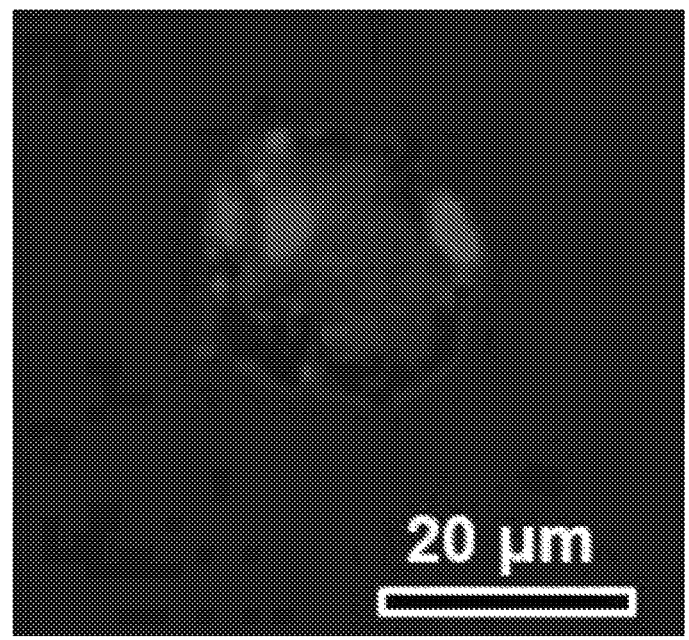
FIG. 39. Fluorescence image of SupraCell-UiO66-$NH_2$ based on Raw 264.7 cells for intracellular NO sensing.
Figure 40:
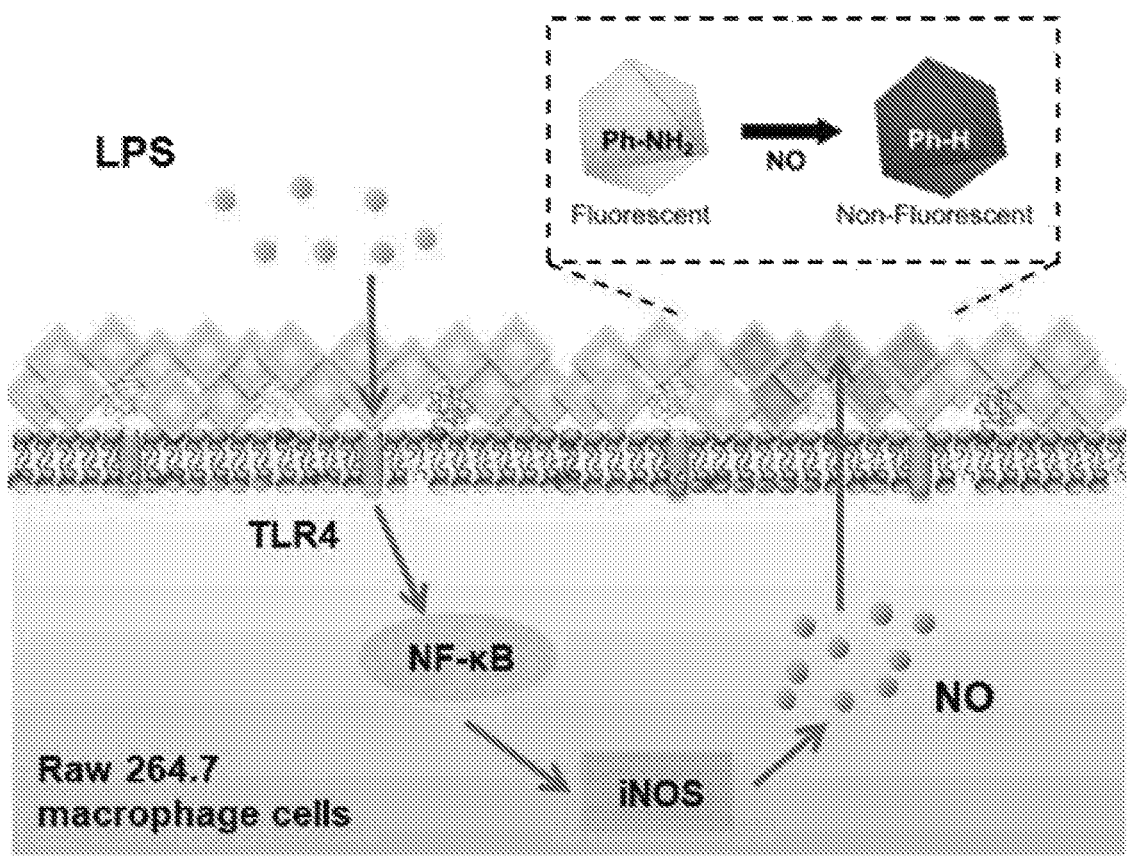
FIG. 40. Schematic illustration of NO activation pathway. Lipopolysaccharide (LPS) cross the MOF layer and bind with the toll-like receptor 4 (TLR4) on Raw 264.7 macrophage cells. Activation of TLR4 by LPS leads to the NF-κB activation and induced the expression of inducible nitric oxide synthase (iNOS), and then release NO. Released NO quenches the fluorescence of the UiO-66-$NH_2$ MOF NPs.

As depicted in FIG. 4A, the Supracell concept can be extended generally to other NP types and combinations to achieve diverse functionalities including multifluorescent labeling, sensing, magnetic, and/or conductive properties (FIGS. 4D-H), while maintaining >90% viability of all respective Supracells (FIG. 22). As an example, multifluorescent SupraCells were fabricated by incubating HeLa cells simultaneously with equal concentrations of three different fluorescently labeled mesoporous silica nanoparticles in a one-pot process for less than one minute (FIG. 38). Confocal microscopy images in 2D and 3D demonstrated the formation of a continuous exoskeleton and a homogeneous distribution of MSNs that preserved stoichiometry of the synthesis solution (FIG. 4E). Sensing Supracells were designed to demonstrate in-situ monitoring of intracellular nitric oxide (NO), which is a key signaling molecule in many pathological processes (Jiang et al., 2013). NO sensing was achieved using luminescent MOF nanobuilding blocks (UiO-66-NH$_2$ NPs) whose luminescence is quenched upon NO-triggered de-amination, allowing real time NO detection (Desai et al., 2015). Using metal-phenolic linker chemistry, mouse macrophage Raw 264.7 cells were encapsulated with UiO-66-NH$_2$ NP-based exoskeletons as demonstrated by the blue fluorescent coronas observed around the surface of SupraCells (FIG. 39). Supracells were then exposed to lipopolysaccharide (LPS), a traditional exogenous activator of the TLR4 (toll-like receptor 4)-NF-κB-iNOS (inducible nitric oxide synthase) (FIG. 39) (Toshchakov et al., 2002) pathway resulting in time-dependent luminescence quenching indicative of NO detection (FIG. 4D). After 32 hours incubation, UiO-66-NH$_2$ Supracells exposed to LPS exhibited about 25% quenching relative to Supracells not exposed to LPS that showed no significant quenching.

Figure 18:
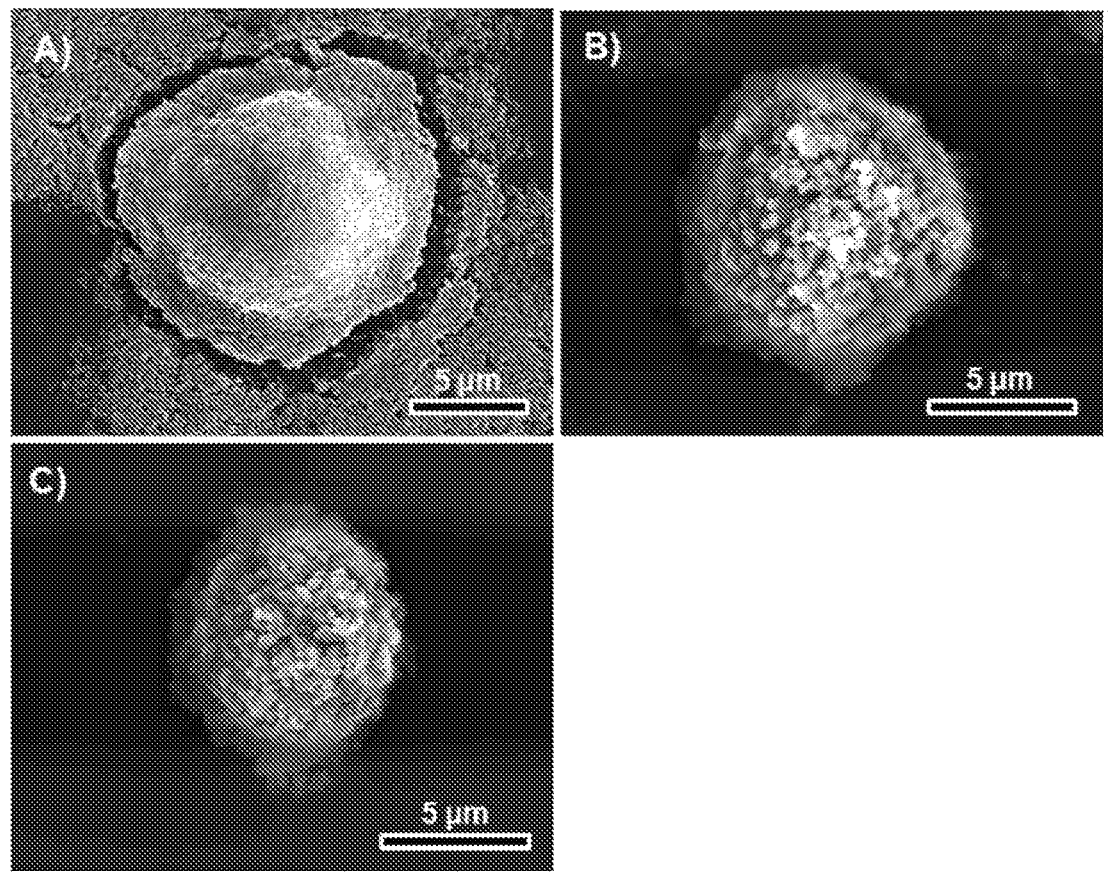
FIGS. 18A-C. SEM images of the Supra-HeLa cell-MIL-100 (Fe) (A), Supra-Raw 264.7 cell-UiO-66-$NH_2$ (B), and Supra-HeLa cell-MET-3(Fe) (C).
Figure 19:
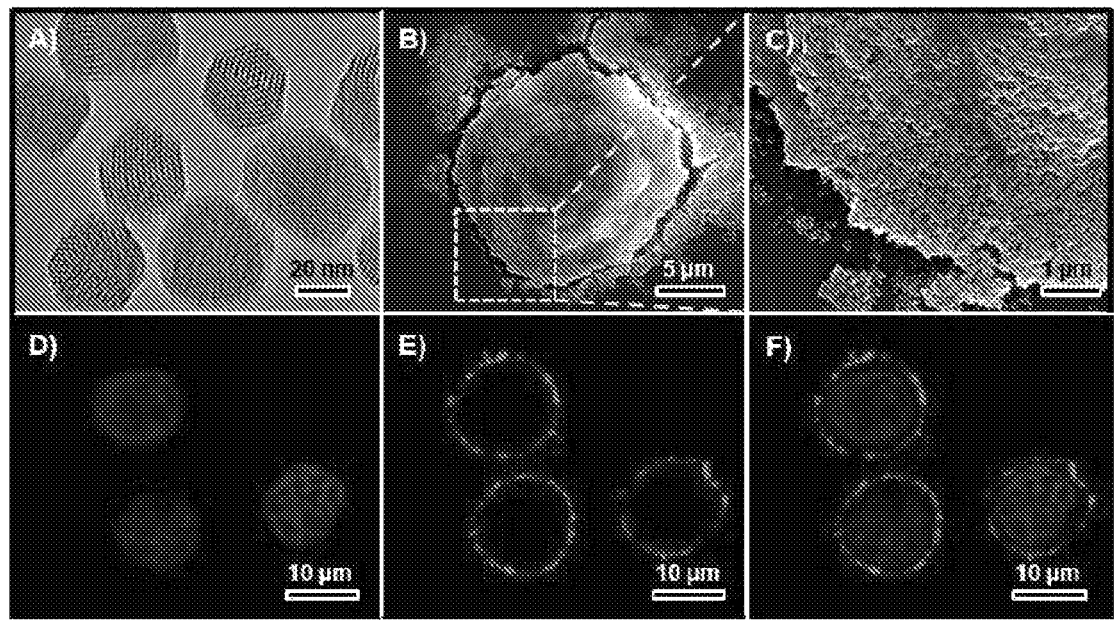
FIGS. 19A-F. A) TEM image tannic-modified mesoporous silica NPs; B-C) SEM image of Supra-HeLa cell-$mSiO_2$; D-F) Fluorescence image of Supra-HeLa cell-$mSiO_2$: nucleus, $mSiO_2$ exoskeleton, combined image (from left to right).
Figure 20:
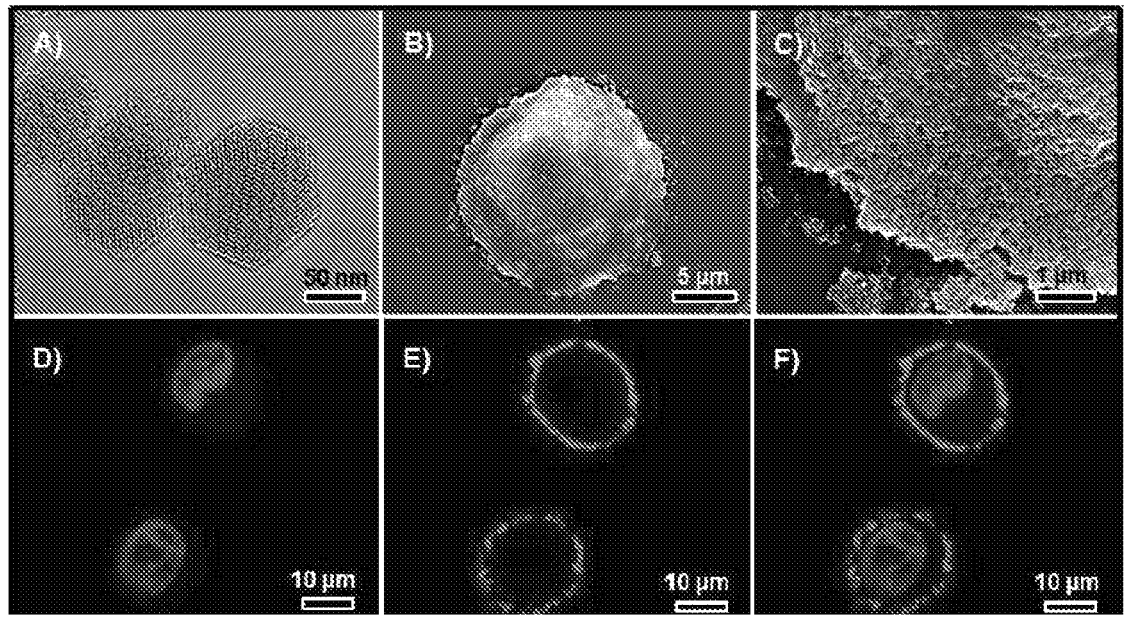
FIGS. 20A-F. A) TEM image thiol-modified mesoporous silica NPs; B-C) SEM image of Supra-HeLa cell-$mSiO_2$; D-F) Fluorescence image of Supra-HeLa cell-$mSiO_2$: nucleus, $mSiO_2$ exoskeleton, combined image (from left to right).
Figure 21:
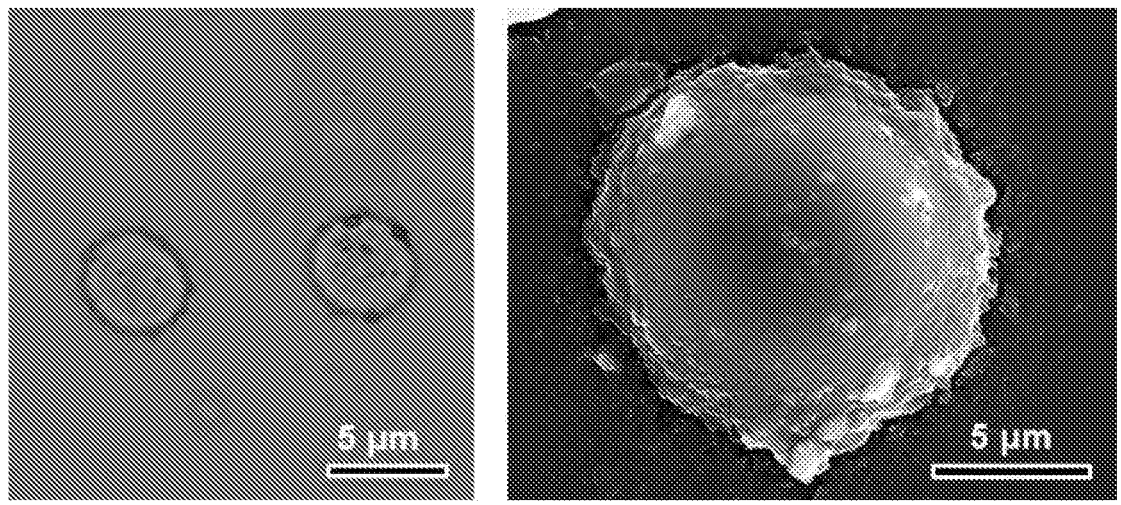
FIG. 21. Optical image (left) and SEM image (right) of magnetic Supra-HeLa cell-$Fe_3O_4$ FIG. 22A-F. Fluorescence microscopy images of MSN (A-C) and UiO-66-$NH_2$ (D-F) NPs internalized by HeLa cells at different time intervals of 5 minutes, 1 hour, and 6 hours.
Figure 41:
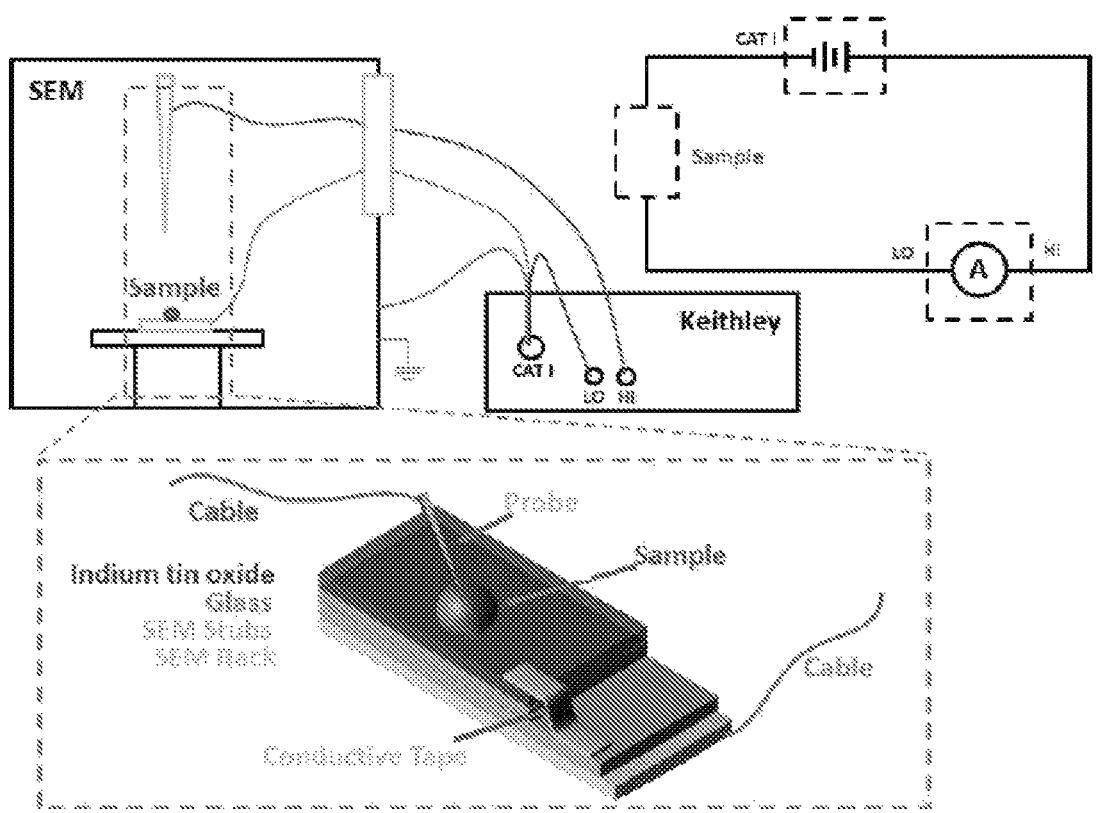
FIG. 41. Schematic illustration of in-situ SEM electrical characterization.
Figure 42:
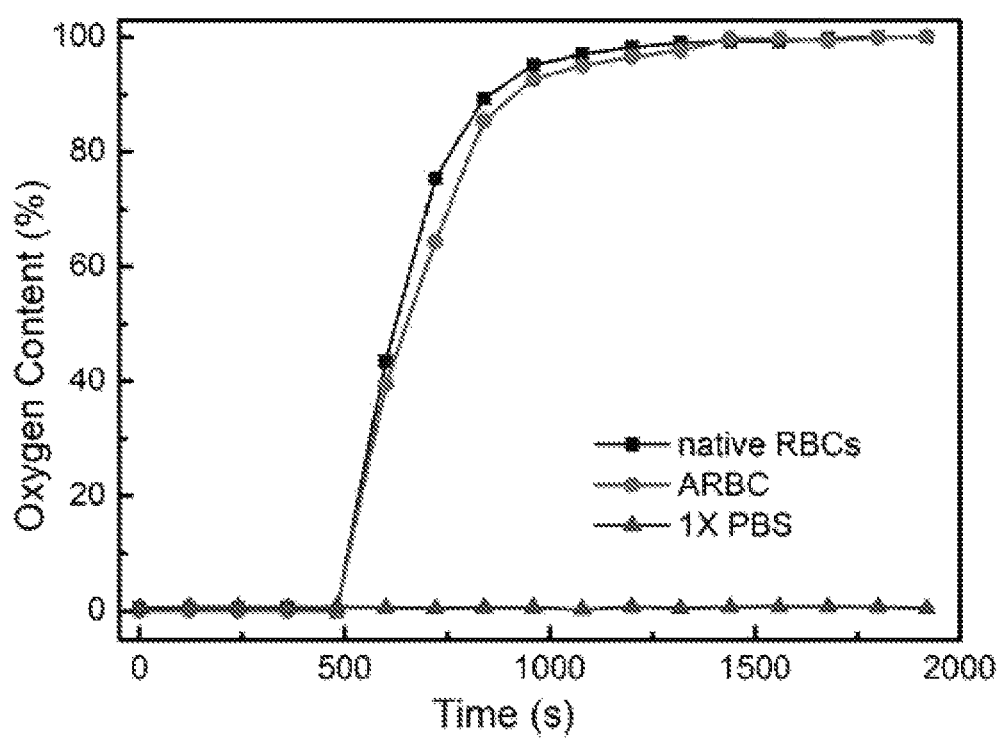
FIG. 42. Capability of reversibly binding oxygen.
Figure 43:
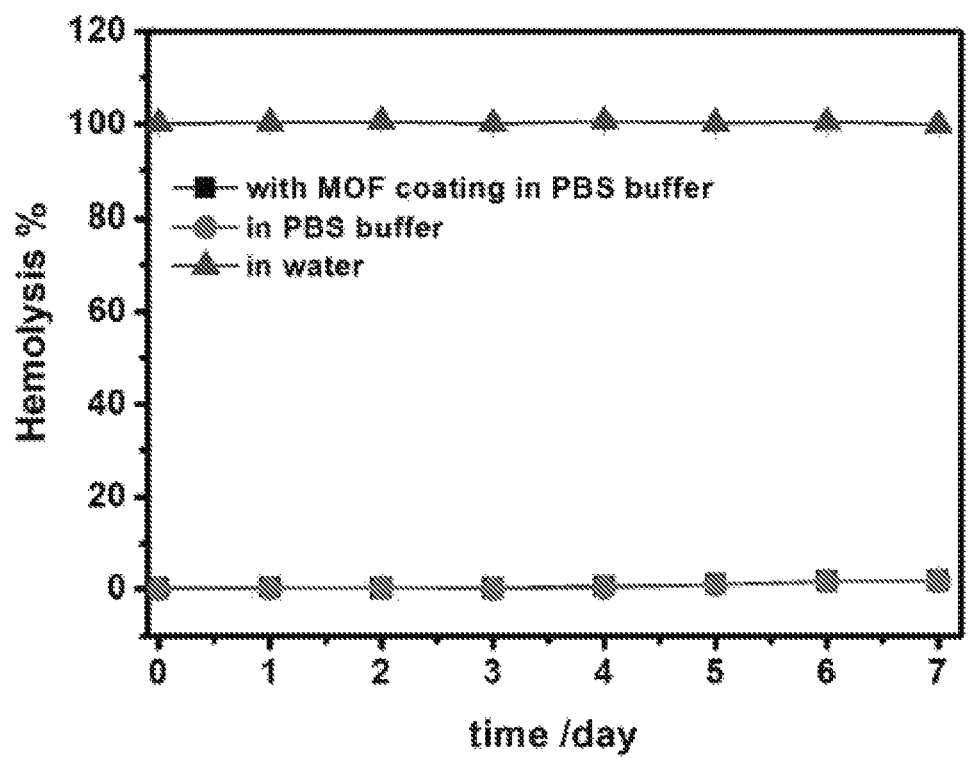
FIG. 43. Hemolysis assay of 7 days storage.
Figure 44:
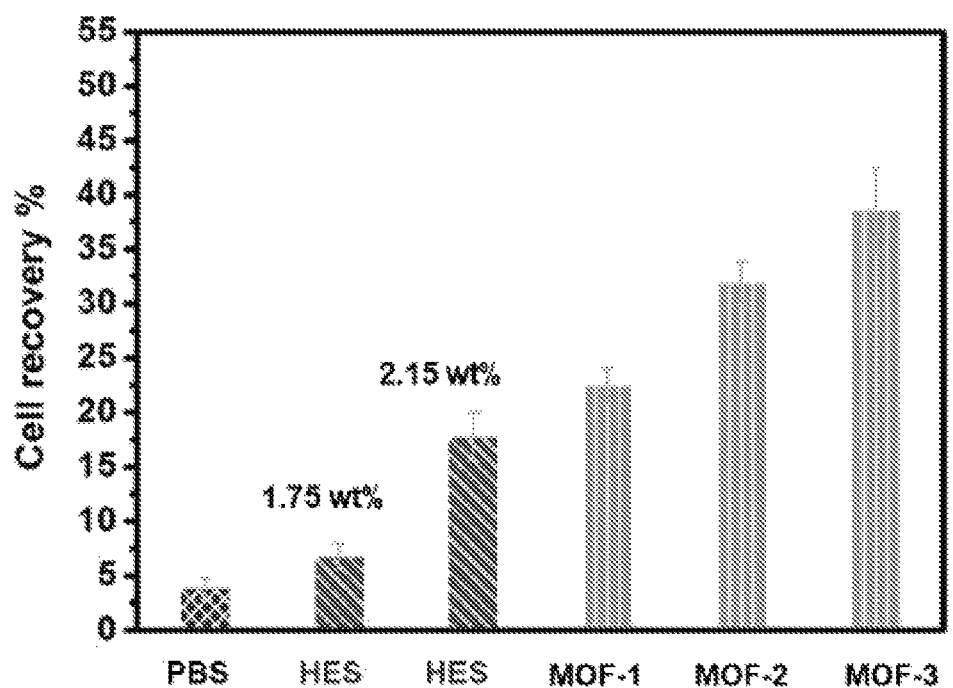
FIG. 44. RBCs cryopreservation and cell recovery.
Figure 45:
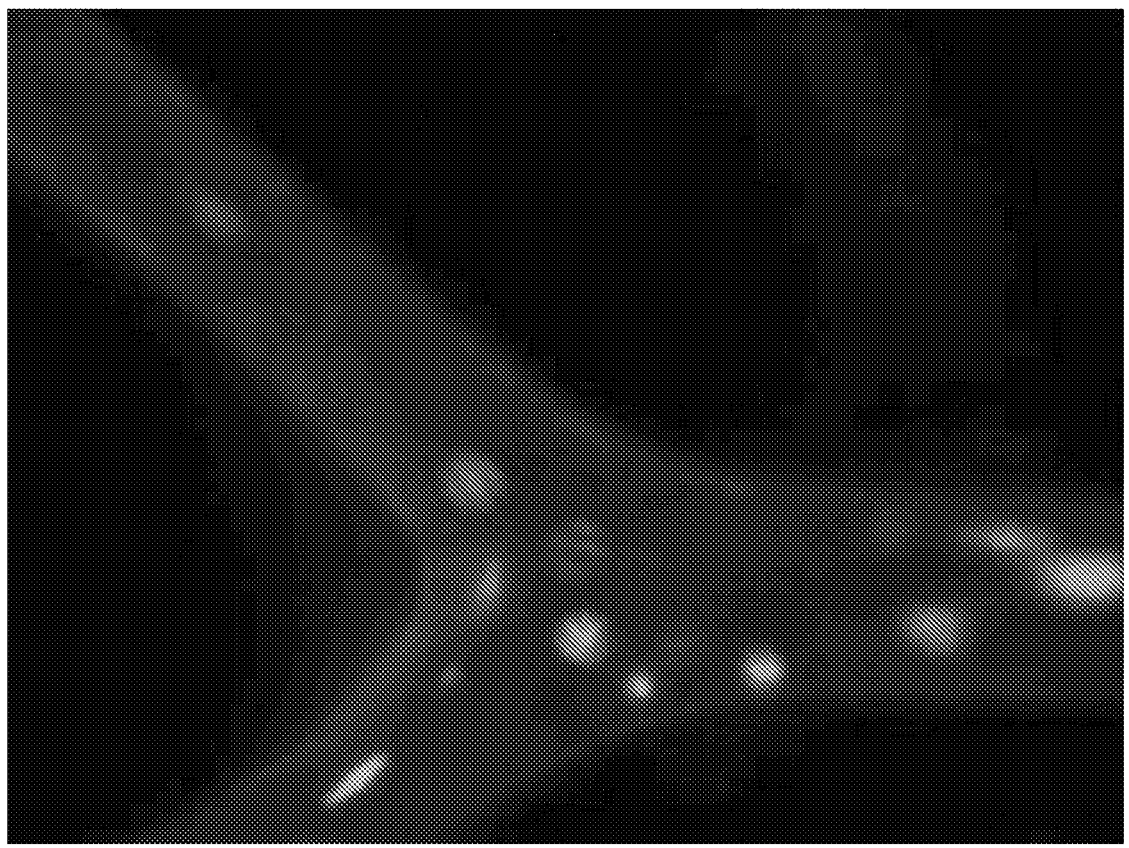
FIG. 45. Circulation in vascular flow of ex ovo chick embryos.

Magnetic SupraCells that hold great potential as magnetic resonance imaging (MRI) agents and micro-motorized cellular constructs were prepared using ca. 8.5-nm diameter iron oxide (Fe$_3$O$_4$) nanobuilding blocks. Using boronate-phenolic linker chemistry, HeLa cells were encapsulated within a continuous magnetic Fe$_3$O$_4$ exoskeleton (FIG. 21), which allows the movement of cells to be controlled via an external magnetic field (FIG. 4F). Finally, electrically conductive SupraCells were synthesized using electrically conductive metal-triazolate MOF of MET-3(Fe)NPs. As shown in FIG. 18, HeLa cells were uniformly encapsulated within MET-3(Fe) exoskeletons. The ohmic conductivity of the SupraCell-MET-3(Fe) was assessed via in-situ SEM electrical characterizations (FIG. 4G and FIG. 41). By placing the SEM probe onto the SupraCell surfaces, representative current-voltage (IV) curves for SupraCell-MRT-3(Fe) and HeLa cells were reliably obtained (FIG. 4G). A high resistivity (about 8.75 MΩ) was measured for the native cells, as expected from the non-conductive cell cytoskeletons and intracellular components. In contrast, a dramatic decrease in the resistance by approximately 3600-fold was measured for the SupraCell-MRT-3(Fe). Conductive SupraCells thus appear as promising living microdevices for applications in biological fuel cells.

In summary, a general and modular approach to create a class of living hybrid materials termed Supracells with seemingly limitless possible functionalities is described herein. Using linker chemistries mammalian cells are encapsulated within nanoparticle-based exoskeletons in an instantaneous process that avoids/abolishes NP internalization pathways such as phagocytosis. The NP exoskeletons are shown to be continuous and to maintain cell viabilities for a long period of time in a non-replicative state endowed with extremophile-like properties. Metal chelation disrupts the linker chemistry and cells return to their native states. The exoskeletons exhibit size selective permeability protecting the cells against toxins and pathogens exceeding 5-nm in diameter. Potential Supracell functionalities are as diverse as the NP exoskeleton building blocks. Using MOFs, mesoporous silica nanoparticles, and iron oxide, multi-fluorescent labeling, sensing, magnetic, and conductive properties were demonstrated, while maintaining >90% viability of all respective Supracells. Extending the Supracell concept to other nanoparticle types and combinations along with other cells promises to create new cellular phenotypes with applications in the fabrication of unique micro-engineered mammalians cells termed SupraCells, where the cellular internalization mechanism of NPs is inhibited so as to form protective and functional NP-based exoskeletons. SupraCells demonstrated high viabilities with preserved typical metabolic signatures of the native cells, enhanced resistances against both endogenous and exogenous stressors, and extraordinary properties foreign to native cells based on the nature of the nanobuilding blocks integrated into their unique exoskeletons. The controllable and modular assembly of Supracells provides almost unlimited possibilities.

Materials and Methods

Reagents. All chemicals and reagents were used as received. Zinc nitrate hexahydrate, 2-methylimidazole, zirconium (IV) chloride, terephthalic acid, 2-aminoterephthalic acid, dimethylformamide (DMF), trimesic acid, iron (III) chloride hexahydrate, tetraethyl orthosilicate (TEOS), (3-aminopropyl)triethoxysilane (APTES), ammonium hydroxide, ammonium nitrate, hexadecyltrimethylammonium bromide (CTAB), cyclohexane, tannic acid, benzene-1,4-diboronic acid, ethylenediaminetetraacetic acid, rhodamine B isothiocyanate mixed isomers, fluorescein isothiocyanate, iron (III) acetylacetonate (Fe(acac) 3), copper (II) nitrate, 7,7,8,8-tetracyanoquinododimethane (TCNQ), benzyl alcohol, methanol, Ham's F-12K (Kaighn's) medium, Iscove's modified Dulbecco's media (IMDM), formaldehyde solution (36.5-38% in H2O), dimethyl sulfoxide (DMSO), doxorubicin (DOX), silver nanoparticles, Congo red, 5,10,15,20-tetrakis (4-sulfona-tophenyl)-21H,23H-porphine manganese (III) chloride, and gentamicin were purchased from Sigma-Aldrich. 2-(N-(7-nitrobenz-2-oxa-1,3-dia zol-4-yl) Amino)-2-deoxyglucose (2-NBDG), Alexa Fluor™ 633 NHS ester (succinimidyl ester) were purchased from Thermo Fisher Scientific. Heat-inactivated fetal bovine serum (FBS), 10×phosphate-buffered saline (PBS), 1×trypsin-EDTA solution, and penicillin-streptomycin (PS) were purchased from Gibco (Logan, UT). Dulbecco's modification of Eagle's medium (DMEM) was obtained from Corning Cellgro (Manassas, VA). Absolute (200 proof) ethanol was obtained from Pharmco-Aaper (Brookfield, CT). CellTiter-Glo® 2.0 Assay was purchased from Promega (Madison, WI). Hoechst 33342 were obtained from Thermo Fisher Scientific (Rockford, IL). 1×phosphate-buffered saline (PBS), Alexa Fluor™ 488 phalloidin and rhodamine phalloidin were purchased from Life Technologies (Eugene, OR). Milli-Q® water with a resistivity of 18.2 MΩ cm was obtained from an inline Millipore RiOs/Origin water purification system.

Characterizations. Scanning electron microscopy (SEM) analyses and energy-dispersive X-ray spectroscopy (EDS) elemental mappings were performed on a Hitachi SU-8010 field-emission scanning electron microscope at 15.0 kV. Transmission electron microscopy (TEM) and high-resolution TEM (HRTEM) imaging were carried out using a Hitachi model H-7650 transmission electron microscope at 200 kV. Wide-angle powder X-ray diffraction (PXRD) patterns were acquired on a Rigaku D/MAX-RB (12 kW) diffractometer with monochromatized Cu K$\alpha$ radiation ($\lambda$=0.15418 nm), operating at 40 KV and 120 mA. The UV-Vis absorption spectra were recorded using a Perkin-Elmer UV/vis Lambda 35 spectrometer. The fluorescence emission measurements were carried out using a fluorescence spectrometer (Perkin-Elmer LS55). To characterize the mechanical properties of the samples, a Triboindenter TI950 (Bruker-Hysitron) equipped with a standard 2D transducer and Berkovich tip were used. Three-color images were acquired using a Zeiss LSM510 META (Carl Zeiss Micro-Imaging, Inc.; Thornwood, NY, USA) operated in channel mode of the LSM510 software.

Nanoparticles Synthesis

ZIF-8 NPs synthesis. ZIF-8 NPs was synthesized following previously reported methods with minor modification (Pan et al, 2011). First, 2.27 g 2-methylimidazole was dissolved in 8.0 g Milli-Q® water, and then 0.117 g $Zn(NO_3)_2 \cdot 6H_2O$ dissolved in 0.8 g Milli-Q® water was added under fast stirring (6000 rpm). The operation was performed at room temperature. After stirring for 15 minutes, the particles were collected by centrifuging, and then washed with ethanol several times. The synthesized ZIF-8 NPs were stored in EtOH before use.

MIL-100(Fe) NPs synthesis. MIL-100(Fe) NPs was synthesized following previously reported methods with no modification (Wuttke et al., 2015). Briefly, 2.43 g iron (III) chloride hexahydrate (9.0 mmol) and 0.84 g trimesic acid (4.0 mmol) in 30 ml $H_2O$ were mixed in a Teflon® tube, sealed, and placed in the microwave reactor (Microwave, Synthos, Anton Paar). The temperature of the mixed solution was fast increased to 130° C. under solvothermal conditions (P=2.5 bar) within 30 seconds, and then kept at 130° C. for 4 minutes and 30 seconds, and finally cooled down again to room temperature. The synthesized NPs were centrifuged down and then washed twice with EtOH. The dispersed NPs were allowed to sediment overnight, and then the supernatant of the sedimented suspension was filtrated (filter discs grade: 391, Sartorius Stedim Biotech) three times to finally yield the MIL-100(Fe) NPs. The synthesized MIL-100(Fe) NPs were stored in EtOH before use.

UiO-66/UiO66-NH2 NPs synthesis. UiO-66 NPs were synthesized following previously reported methods with no modification (Lu et al., 2013). Briefly, 25.78 mg $ZrCl_4$ (0.11 mmol) and 13.29 mg 1,4-benzenedicarboxylic acid (0.08 mmol) were dissolved in 10 mL of DMF solution. Then 1.441 g acetic acid (0.024 M) was added into the above solution. The mixed solution was placed in an oven (120° C.) for 24 hours. After the reaction mixture was cooled to room temperature, the resulted NPs were subsequently washed with DMF and methanol via centrifugation redispersion cycles. The synthesized UiO-66 NPs were stored in EtOH before use. For the synthesis of UiO66-$NH_2$, the same protocol was used except the replacing the organic ligand 1,4-benzenedicarboxylic acid to 2-amino terephthalic acid.

MET-3 (Fe) NPs Synthesis. MET-3 (Fe) NPs was synthesized following previously reported methods with no modification (Gandara et al., 2012). Briefly, 1.22 g $Cu(NO_3)_2 \cdot 3H_2O$ (5.24 mmol) and 0.58 g trimesic acid (2.76 mmol) were first dissolved in 5 g DMSO solution to form the precursor solution. Then 0.2 mL of the precursor solution was dropped into 10 mL methanol solution under stirring in 1 minute. After the stirring was continued for 20 minutes, the precipitate was collected by centrifugation and washed several times with methanol. The synthesized HKUST-1 NPs were stored in MeOH before use.

Mesoporous silica NPs (MSN) synthesis. MSN NPs was synthesized following previously reported methods in our group with no modification (Durfee et al., 2016). Briefly, 0.29 g of CTAB (0.79 mmol) was dissolved in 150 mL of 0.51 M ammonium hydroxide solution in a 250 mL beaker, sealed with parafilm (Neenah, WI), and placed in a mineral oil bath at 50° C. After continuously stirring for 1 hour, 3 mL of 0.88 M TEOS solution in EtOH and 1.5 μL APTES were combined and added immediately to the mixed solution. After another 1 hour of continuous stirring, the particle solution was stored at 50° C. for another 18 hours under static conditions. Next, the solution was passed through a 1.0 μm Acrodisc™ 25 mm syringe filter (PALL Life Sciences, Ann Arbor, MI) followed by a hydrothermal treatment at 70° C. for 24 hours. To remove the CTAB, the synthesized MSN NPs were transferred to 75 mM ammonium nitrate solution in ethanol, and placed in an oil bath at 60° C. for 1 hour with reflux and stirring. The MSN NPs were then washed in 95% ethanol and transferred to 12 mM HCl ethanolic solution and heated at 60° C. for 2 hours with reflux and stirring. Finally, MSN NPs were washed in 95% ethanol, then 99.5% ethanol, and stored in 99.5% ethanol before use.

$Fe_3O_4$ NPs synthesis. Bare $Fe_3O_4$ NPs was synthesized following the reported methods with no modification (Li et al., 2016). Briefly, 0.687 g of $Fe(acac)_3$ (1.94 mmol) was dissolved in 9 mL of benzyl alcohol. The mixed solution was heated to 170° C. with reflux and stirring at 1500 rpm for 24 hours. After the reaction was cooled down to room temperature, 35 mL EtOH was added into the mixed, and then centrifuged at 20000 rpm for 10 minutes. The supernatant was discarded, and the resulted precipitate was washed with EtOH twice to yield to the $Fe_3O_4$NPs. The synthesized $Fe_3O_4$ NPs were stored in EtOH before use.

Cell Culture

Cell culture was performed using standard procedures (atcc.org). For adherent cells, HeLa (CCL-2) and A549 (CCL-185) were obtained from American Type Culture Collection (ATCC) and maintained in DMEM and F-12K media containing 10% FBS at 37° C. and 5% $CO_2$, respectively. Cells were passaged at approximately 80% confluency. For coating purposes, living adherent cells (HeLa and A549) were removed from plate bottom using Trypsin-EDTA (0.25%) and then suspended in culture media. For suspension cells, HL-60 (CCL240) was obtained from American Type Culture Collection (ATCC) and maintained in IMDM media containing 10% FBS at 37° C. and 5% $CO_2$. The media of HL-60 cell were changed every 3 days. For phagocytosis purposes, HL-60 cells were differentiated into neutrophil-like cells by addition of 1.3% DMSO to the culture medium for 10 days (Blari et al., 1986).

Supracell Construction

Synthesis of SupraCells with ZIF-8 NPs coating. Two million living mammalian cells were rinsed with 1×PBS, and then suspended in 500 μL of 400 μg/mL ZIF-8 NPs in 1×PBS solution. After 10 seconds vortex, 500 μL of 32 μg/mL tannic acid in 1×PBS solution were added with 30 seconds vigorous mixing. Then, the living mammalian cells with ZIF-8 NPs coating (SupraCell-ZIF-8) were then rinsed with 1×PBS twice, and stored in culture media. For RBCs, 5 million RBCs were suspended in 500 μL of 250 μg/mL ZIF-8 nanoparticles in 1×PBS (pH 5) solution. After 10 seconds vortex, 500 μL of 32 μg/mL tannic acid in 1×PBS (pH 5) solution were added with 10 seconds vigorous mixing. The ZIF-8 nanoparticles coating RBCs (RBCs@ZIF-8) were then rinsed with 1×PBS (pH 7.4), and stored in 1×PBS (pH 7.4).

Synthesis of SupraCells with MIL-100(Fe) NPs coating. Two million living cells were rinsed with 1×PBS and then suspended in 500 μL of 200 μg/mL MIL-100(Fe) NPs in 1×PBS solution. After 10 seconds vortex and 1 minute incubation, 500 μL of 32 μg/mL tannic acid in 1×PBS solution were added with 60 seconds vigorous mixing. Then, the living mammalian cells with MIL-100(Fe) NPs coating {SupraCell-MIL-100(Fe)} were then rinsed with 1×PBS twice, and stored in culture media. For RBCs, 5 million RBCs were suspended in 500 μL of 200 μg/mL MIL-100 nanoparticles in 1×PBS (pH 5) solution. After 10 seconds vortex and 20 seconds incubation, 500 μL of 32 μg/mL tannic acid in 1×PBS (pH 5) solution were added with 20 seconds vigorous mixing. The MIL-100 nanoparticles coating RBCs (RBCs@MIL-100) were then rinsed with 1×PBS (pH 7.4), and stored in 1×PBS (pH 7.4). This process represents the typical procedure for single MIL-100 nanoparticles layer formation and it could be repeated one or two times to achieve multilayer MIL-100 nanoparticles coating RBCs (RBCs@MIL-100-1, RBCs@MIL-100-2, and RBCs@MIL-100-3).

Synthesis of SupraCells with MET-3-Fe NPs coating. Two million living mammalian cells were rinsed with 1×PBS, and then suspended in 500 μL of 400 μg/mL MET-3-Fe NPs in 1×PBS solution. After 10 seconds vortex, 500 μL of 32 μg/mL tannic acid in 1×PBS solution were added with 30 seconds vigorous mixing. Then, the living mammalian cells with MET-3-Fe NPs coating (SupraCell-MET-3-Fe) were then rinsed with 1×PBS twice, and stored in culture media.

Synthesis of SupraCells with MSN NPs coating. Protocol A): for amine-functionalized MSN NPs, before coating, the synthesized NPs were incubated in a tannic acid solution (0.4 mg/mL in 0.5×PBS) for several hours and then washed with DI water twice. For living mammalian cells coating, Two million living cells were rinsed with 1×PBS and then suspended in 500 μL of 100 μg/mL MSNs in 1×PBS solution. After 10 seconds vortex and 1 min incubation, 500 μL of 12 μM benzene-1,4-diboronic acid in 1×PBS solution were added with 60 seconds vigorous mixing. Then, the living mammalian cells with MSN NPs coating (SupraCell-MSN) were then rinsed with 1×PBS twice, and stored in culture media.

Protocol B): for thiol-functionalized MSN NPs, the synthesized NPs were washed with DI water twice. For living mammalian cells coating, Two million living cells were rinsed with 1×PBS and then suspended in 500 μL of 100 μg/mL MSNs in 1×PBS solution. After 10 seconds vortex and 1 min incubation, 500 μL of 50 μg/mL 4-arm-PEG5K-SH and 50 μM $H_2O_2$ in 1×PBS solution were added with 60 seconds vigorous mixing. Then, the living mammalian cells with MSN NPs coating (SupraCell-MSN) were then rinsed with 1×PBS twice, and stored in culture media.

Synthesis of SupraCells with $Fe_3O_4$ NPs coating. Before coating, the bare $Fe_3O_4$ NPs were incubated in a tannic acid solution (0.4 mg/mL in 0.5×PBS) for several hours and then washed with DI water twice. For living mammalian cells coating, two million living cells were rinsed with 1×PBS and then suspended in 500 μL of 100 μg/mL $Fe_3O_4$ NPs in 1×PBS solution. After 10 seconds vortex and 1 minute incubation, 500 μL of 12 μM benzene-1,4-diboronic acid in 1×PBS solution were added with 60 seconds vigorous mixing. Then, the living mammalian cells with $Fe_3O_4$ NPs coating (SupraCell-$Fe_3O_4$) were then rinsed with 1×PBS twice, and stored in culture media.

Synthesis of SupraCells with UiO-66 NPs coating. For RBCs, 5 million RBCs were suspended in 500 μL of 40 μg/mL UiO-66 nanoparticles in 1×PBS (pH 5) solution. After 10 seconds vortex and 30 seconds incubation, 500 μL of 40 μg/mL tannic acid in 1×PBS (pH 5) solution were added with 30 seconds vigorous mixing. The UiO-66 nanoparticles coating RBCs (RBCs@UiO-66) were then rinsed with 1×PBS (pH 7.4), and stored in 1×PBS (pH 7.4).

Synthesis of SupraCells with $Fe_3O_4$@ZIF-8 NPs coating. For RBCs, 5 million RBCs were suspended in 500 μL of 250 μg/mL $Fe_3O_4$@ZIF-8 nanoparticles in 1×PBS (pH 5) solution. After 10 seconds vortex and 20 seconds incubation, 500 μL of 40 μg/mL tannic acid in 1×PBS (pH 7.4) solution were added with 20 seconds vigorous mixing. The $Fe_3O_4$@ZIF-8 nanoparticles coating RBCs (RBCs@ $Fe_3O_4$@ZIF-8) were then rinsed with 1×PBS (pH 7.4), and stored in 1×PBS (pH 7.4).

Synthesis of SupraCells with MSN@ZIF-8 NPs coating. For RBCs, 5 million RBCs were suspended in 500 μL of 400 μg/mL MSN@ZIF-8 nanoparticles in 1×PBS (pH 5) solution. After 10 seconds vortex and 20 seconds incubation, 500 μL of 32 μg/mL tannic acid in 1×PBS (pH 7.4) solution were added with 20 seconds vigorous mixing. The MSN@ZIF-8 nanoparticles coating RBCs (RBCs@ MSN@ZIF-8) were then rinsed with 1×PBS (pH 7.4), and stored in 1×PBS (pH 7.4).

Cell Viability Test

Cell viability of the constructed SupraCells was assessed by CellTiter-Glo® 2.0 Assay. Briefly, SupraCell samples were first diluted to the concentration of 50,000 cells/mL, and then 100 μL of the SupraCell samples were added into 96-well plate (White Opaque). After that, 100 μL of CellTiter-Glo® 2.0 Reagent was dispensed into each well. The luminescence was recorded 10 minutes after addition of CellTiter-Glo® 2.0 Reagent by a BioTek microplate reader. The Cell viability was calculated as a percentage of non-coated mammalian cells.

SupraCell Shell Controlled Destruction

SupraCell-ZIF-8 or SupraCell-MIL-100(Fe) were rinsed with 1×PBS, and then suspended in 20 mM EDTA PBS solution (20 mM, pH 5.0) for different times (maximum time: 30 minutes) to allow the controlled destruction of MOF NPs. Then, the cells were rinsed with 1×PBS twice and then stored in culture media.

Cell Culture Test

Native HeLa cells and SupraCell-ZIF-8 (stored 2 hours or 24 hours, and then etch the shell) at the density of 100,000 cells/mL were seeded on glass substrates and then cultured at 37° C. and 5% $CO_2$ for 24 hours. Then, the live mammalian cells were imaged on a glass slide using the Leica DMI3000 B inverted microscope.

SupraCell Mechanical Characterization

To characterize the mechanical properties of the samples, a Triboindenter TI950 (Bruker-Hysitron) equipped with a standard 2D transducer and Berkovich tip were used. The tip was calibrated using a standard Fused Quartz sample for the required contact depth. To remove the surface roughness effects and calibration limits, the extracted curves with contact depths less than 50 nm have not been used for our data analysis. A rigid glass plate (E about 60 GPa) was used as the substrate for our indentation studies. The extracted stiffness and elastic modulus of the samples have been calculated according to the theory developed by Oliver-Pharr (1992), and using the unloading section of the curves.

SupraCell Permeability Test

The SupraCell permeability test was performed on Supracell-MIL-100(Fe) toward a fluorescent glucose sugar of 2-NBDG and nucleic acid (nuclear) staining dye of Hoechst 33342. Briefly, the native HeLa cells and supra-HeLa cells with MIL-100(Fe) coating were incubated with sugar of 2-NBDG (200 μM) and nuclear staining dye of Hoechst 33342 (3.2 μM) in cell culture media under cell culture condition for 1 hour. After incubation, the cell samples were imaged using the Leica DMI3000 B inverted microscope.

SupraCell Cytoprotection Test

Cytoprotection test to DOX. The cytoprotection test was performed on Supracell-MIL-100 (Fe). Briefly, the native HeLa cells and Supracell-MIL-100 (Fe) were seeded on 96-well plate at the density of 200,000 cells/mL. Then different concentration of DOX (0.01, 0.1, 1.0, 10, 20, and 50 μg/ML) was added in the cell culture media under cell culture condition. After incubation for 2 hours, the viability of the cells or SupraCells was measured by CellTiter-Glo® 2.0 Assay.

Cytoprotection test to Ag NPs. The cytoprotection test was performed on Supracell-MIL-100 (Fe). Briefly, the native HeLa cells and Supracell-MIL-100 (Fe) were seeded on 96-well plate at the density of 200,000 cells/mL. Then, various solutions of different concentration of Ag NPs (0, 4, 8, and 12 μg/ML) were added in the cell culture media under cell culture condition. After incubation for 4 hours, the viability of the cells or SupraCells was measured by CellTiter-Glo® 2.0 Assay.

Phagocytosis Assay

Phagocytosis of GFP-expressing Salmonella typhimurium bacteria were performed in 10% FBS with DMSO free IMDM medium which was preheated to 37° C. Bacteria solution were added to differentiated HL-60 cells and supra-HL-60-MIL-100(Fe) in 100:1 bacteria/cells ratio, and then incubated for 1 hours at 37° C. under rotation. Subsequently, both of the cells were rinsed with 1×PBS twice. Then the cells were incubated with 50 μg/mL gentamicin under cell culture condition for 30 minutes to remove extracellular bacteria. After that, the cells were fixed in 3.7% formaldehyde in 1×PBS at room temperature for 10 minutes, rinsed with PBS, and then cellular filamentous actin network and nuclei were stained by rhodamine phalloidin and hoechst 33342, respectively. After staining, the cell samples were imaged using the Leica DMI3000 B inverted microscope.

SupraCell Tolerance at Harsh Conditions

Tolerance of pH. Native HeLa cells and Supra-HeLa cell-MIL-100 (Fe) were rinsed with saline solution (154 mM NaCl), and then suspended in saline solution at the density of 1,000,000 cells/mL. 20 μL of cell saline solution was added on the 96-well plate, and then 80 μL of different pH solution with the same ion strength was dispensed into well. The final pH value was adjusted to 4, 5, 6, 7.4, 8, 9, 10, and 11. The plate was then placed in an incubator at 37° C. and 5% $CO_2$ for 1 hour. After 1 hour incubation, the viability of the cells was measured by the CellTiter-Glo® 2.0 Assay.

Tolerance of ion strength. Native Hela cells and Supra-HeLa cell-MIL-100 (Fe) were rinsed with 1×PBS and then incubated in 0.25×PBS, 0.5×PBS, 0.75×PBS, 1×PBS, 2×PBS, 3×PBS, 4×PBS, 5×PBS for 1 hour, respectively. After 1 hour incubation, the viability of the cells was measured by the CellTiter-Glo® 2.0 Assay. For imaging purposes, the cell samples were fixed in 3.7% formaldehyde in the related PBS solution at room temperature for 10 minutes, rinsed with PBS, and then the cellular filamentous actin network and nuclei were stained with fluorescent probes of Alexa Fluor™ 488 phalloidin and Hoechst 33342, respectively. After staining, the cell samples were imaged using the Leica DMI3000 B inverted microscope and Leica TCS SP8 confocal laser scanning microscope. The cell counting was processed by Image Pro-Plus software.

Tolerance of ROS. The ROS tolerance test was performed on Supra-HeLa cell-MIL-100 (Fe) toward $H_2O_2$. Briefly, the native Hela cells and Supra-HeLa cell-MIL-100 (Fe) were rinsed with 1×PBS, and then suspended again in 1×PBS. Then, the cell samples were seeded on the 96-well plate at the density of 20,000 cells/well, and then incubated with different concentration of $H_2O_2$ (0, 2, 4, 6, and 8 mM) in 1×PBS solution at room temperature. After 1 hour incubation, the viability of the cells was measured by the CellTiter-Glo® 2.0 Assay.

Tolerance of UV exposure. Native HeLa cells and Supra-HeLa cell-MIL-100 (Fe) {or Supra-HeLa cell-MIL-100 (Fe) with Congo red dye loading} were rinsed with 1×PBS, and then suspended again in 1×PBS. The cells were seeded on the UV transparent 96-well plate at the density of 200,000 cells/mL. The plate was placed in a home-made dark chamber equipped with a compact UV Lamps (4 W lamps, Entela UL3101). The distance between the plate and the UV lamp was adjusted to be 5 cm (Park et al., 2014). After UV irradiation for 2 hours (254 and 308 nm, respectively), the viability of the cells was measured by the CellTiter-Glo® 2.0 Assay and LIVE/DEAD® Cell Imaging Kit.

SupraCell-Modular Nanoparticles Superassembly

Amine-functionalized MSN NPs with Fluorescein isothiocyanate, Rhodamine B isothiocyanate, and Alexa Fluor™ 633 NHS Ester (Succinimidyl Ester) labeling were used for modular nanoparticles superassembly. Before coating, all the NPs were in a tannic acid solution (0.4 mg/mL in 0.5×PBS) for several hours and then washed with DI water twice. For SupraCell construction, Two million living cells were rinsed with 1×PBS and then suspended in 500 μL of 100 μg/mL mixed MSNs (~1:1:1 ratio) in 1×PBS solution. After 10 seconds vortex and 1 minute incubation, 500 μL of 12 μM benzene-1,4-diboronic acid in 1×PBS solution were added with 60 seconds vigorous mixing. Then, the living mammalian cells with three kinds of MSN NPs coating were then rinsed with 1×PBS twice, and stored in culture media.

SupraCell-Magnetic Manipulation

The magnetic SupraCell have been oriented in the direction of an external magnetic field produced by a neodymium magnet. The bright field images were taken by Leica DMI3000 B inverted microscope to evaluate the magnetic guidance.

SupraCell-In Situ NO Sensing

Supra-Raw 264.7-UiO-66-$NH_2$ was rinsed with 1×PBS and suspended cell culture media. The cells were seeded on the black 96-well plate at the density of 6,000,000 cells/mL. LPS solution was added to Supra-Raw 264.7@UiO-66-$NH_2$ with a final concentration of 20 μg/mL. After that, Supra-Raw 264.7@UiO-66-$NH_2$ with or without LPS were incubated for at 37° C. and 5% $CO_2$. The presence of NO was determined through fluorescence signals measured by a BioTek microplate reader with excitation at 370 nm and emission at 440 nm. All fluorescence measurements were performed at room temperature.

Capability of Reversibly Binding Oxygen

Capability of reversibly binding oxygen was detected by analyzing changes of UV-Vis absorption spectra (300-700 nm) in oxygenated and deoxygenated solutions. For complete deoxygenation, nitrogen gas was inflown into sample solution to remove most of the oxygen. After 2 hours, sodium dithionite (Na2S2O4) was added, and UV-Vis absorption spectrum was scanned by a BioTek microplate reader. For oxygenation, sample solutions were exposure under atmospheric oxygen for more than 2 hours, and UV-Vis absorption spectrum was recorded. This process represents the typical procedure for reversibly binding oxygen capability and it was repeated two times.

The deoxygenated sample ($\lambda_{max}$=430 nm) could be gradually converted to oxygenated sample ($\lambda_{max}$=415 nm) by exposing under air atmosphere at room temperature. Thus the oxygenation rate of deoxygenated sample was monitored by observation of the absorbance change via UV-Vis spectroscopy. The oxygenated content of each sample was calculated using the following equation: Oxygenated content (%)=$100*(Abs_{t0}-Abs_t)/(Abs_{t0}-Abs_{tmin})$ Where $Abs_{t0}$ and $Abs_t$ stand for the 430 nm absorbance at the starting point (t=0, complete deoxygenated state) and at the specific time, respectively, and $Abs_{tmin}$ stands for the 430 nm absorbance when the absorbance of 430 nm reached the minimum value.

Hemolysis Assay

Native RBCs and RBCs@Mil-100 were rinsed with 1×PBS (pH 7.4) solution and then suspended in 1×PBS (pH 7.4) solution at room temperature for 7 days. After centrifugation (300 g, 5 minutes), the absorbance of hemoglobin in the supernatant was measured by a BioTek microplate reader (Winooski, VT) at 540 nm to calculate the hemolysis percentage. Double distilled (D.I.) water and 1×PBS (pH 7.4) solution containing native RBCs were used as the positive controls (100% hemolysis) and negative controls (0% hemolysis), respectively. The hemolysis percentage of each sample was determined using the reported equation. Percent hemolysis (%)=$100*(\text{Sample } Abs_{540nm}-\text{Negative control } Abs_{540nm})/(\text{Positive control } Abs_{540nm}-\text{Negative control } Abs_{540nm})$ RBCs Cryopreservation and Cell Recovery Hydroxyethyl starch (HES) were dispersed in 1×PBS (pH 7.4) solution with the concentration of 175.0 and 215.0 mg/mL. 50 million/mL Native RBCs and RBCs@Mil-100 were rinsed with 1×PBS (pH 7.4) solution and then suspended in 1×PBS (pH 7.4) solution or HES solution. Each sample was frozen by immersion in liquid nitrogen (−196° C.) for 2 hours prior to thawing. Thawing of samples was undertaken by transferring samples to 4° C. in the fridge for a minimum of 2.5 hours. Slow thawing process promoted extensively ice recrystallization while ensuring samples were fully thawed. After fully thawing of samples, the samples were centrifuged (300 g, 5 minutes) and the absorbance of hemoglobin in the supernatant was measured by a BioTek microplate reader (Winooski, VT) at 540 nm to calculate the cell recovery. Double distilled (D.I.) water and 1×PBS (pH 7.4) solution containing native RBCs were used as the positive (100% hemolysis or 0% cell recovery) and negative controls, respectively. The cell recovery percentage of each sample was determined using the reported equation. [2] Percent hemolysis (%)=$100*(\text{Positive control } Abs_{540nm}-\text{Sample } Abs_{540nm})/(\text{Positive control } Abs_{540nm}-\text{Negative control } Abs_{540nm})$ Test of Vascular Flow in Ex Ovo Chick Embryos The vascular flow characteristics of RBCs@UiO-66 were tested using Ex ovo chick embryo model and was conducted following institutional approval (Protocol 11-100652-T-HSC). Briefly, eggs were acquired from East Mountain Hatchery (Edgewood, N.M.) and placed in a GQF 1500

Digital Professional incubator (Savannah, GA) for 3 days. Embryos were then removed from shells by cracking into 100 ml polystyrene weigh boats. Ex ovo chick embryos were covered and incubated at 37° C., 100% humidity. 5 million cells/mL or 40 million cells/mL of native RBCs and RBCs@UiO-66 were incubated in 1×PBS (pH 7.4) solution with 10 mg/mL bovine serum albumin (BSA) for 20 minutes and then rinsed and stored in 1×PBS (pH 7.4) solution. 50 µL of samples in 1×PBS (pH 7.4) solution were injected into secondary or tertiary veins via pulled glass capillary needles. Embryo chorioallantoic membrane (CAM) vasculature was imaged using a customized avian embryo chamber and a Zeiss Axio Examiner upright microscope with heated stage.

NO Sensor 10 mM NaOH and 1×PBS (pH 7.4) solutions were pre-bubbled with nitrogen for 2 hours to remove the dissolved oxygen. NO precursor Diethylamine NONOate sodium salt was added to a 10 mM NaOH solution to make the 500 µM stock solution. The stock solution was diluted with 1×PBS (pH 7.4) solutions to generate various concentrations of NO solutions. The NO-containing PBS solutions were set for at least 15 minutes to allow the NO concentrations to saturate before NO sensor studying. 2.5 million RBCs@MSN(DAR-1 loaded)@ZIF-8 were suspended in NO-containing PBS solution. After 5 minutes incubation, the fluorescence emission spectrum was obtained on a SHIMADZU spectrofluorophotometer RF-5301pc.

Exemplary Embodiments

The disclosure provides an encapsulated living mammalian cell which comprises a plurality of linked nanoparticles enveloping the cell. In one embodiment, the cell is a human cell. In one embodiment, the cell is a primate cell. In one embodiment, the cell is a murine, bovine, equine, canine, feline, ovine, caprine or swine cell. In one embodiment, an individual nanoparticle has a diameter of about 5 nm to about 500 nm. In one embodiment, an individual nanoparticle has a diameter of about 10 nm to about 300 nm. In one embodiment, an individual nanoparticle has a diameter of about 15 nm to about 250 nm. In one embodiment, an individual nanoparticle has a diameter of about 300 nm to about 500 nm. In one embodiment, an individual nanoparticle has a diameter of about 100 nm to about 300 nm. In one embodiment, an individual nanoparticle has a diameter of about 50 nm to about 250 nm. In one embodiment, the nanoparticles are metal-organic nanoparticles. In one embodiment, the nanoparticles comprise Zn or Co imidazolate. In one embodiment, the nanoparticles comprise Ni, Mn, Ti, W, Mg, Al, Cu or Cr. In one embodiment, the nanoparticles comprise iron oxide or silica. In one embodiment, the nanoparticles are linked using tannic acid. In one embodiment, the nanoparticles are linked via a metal-phenolic interaction. In one embodiment, wherein the nanoparticles are linked via a boronic acid-phenolic acid interaction. In one embodiment, the nanoparticles are linked via a thiol linkage. In one the nanoparticles are functionalized with amine or phenol prior to linking. In one embodiment, the nanoparticles are functionalized with thiol prior to linking. In one embodiment, the linkage is reversible. In one embodiment, the nanoparticles comprise ZIF-8, MIL-100, UiO-66, MET-3-Fe, mesoporous silica (mSiO$_2$), or iron oxide (Fe$_3$O$_4$).

In one embodiment, a method of preparing an encapsulated living mammalian cell is provided that includes combining an amount of a plurality of mammalian cells and an amount of a plurality of nanoparticles which are functionalized with one or more linkers under conditions that result in one or more mammalian cells being encapsulated with a plurality of linked nanoparticles.

In one embodiment, a method of preparing an encapsulated living mammalian cell is provided that includes combining an amount of a plurality of mammalian cells, an amount of a plurality of nanoparticles, and an amount of linkers under conditions that result in one or more mammalian cells being encapsulated with a plurality of linked nanoparticles. In one embodiment, the linkage is reversible. In one embodiment, the encapsulated mammalian cells have or have enhanced sensing, electrical or magnetic properties, e.g., relative to unencapsulated corresponding cells. In one embodiment, Fe3O4 nanoparticles provide magnetic properties. In one embodiment, MET-3 (Fe) nanoparticles provide electrical properties. In one embodiment, a magnetic T-cell, B-cell or pancreatic cell may be useful for targeting. In one embodiment, the cells are human cells. In one embodiment, an individual nanoparticle has a diameter of about 5 nm to about 500 nm, about 10 nm to about 300 nm, or about 15 nm to about 250 nm. In one embodiment, an individual nanoparticle has a diameter of about 300 nm to about 500 nm, about 100 nm to about 300 nm, or about 50 nm to about 250 nm. In one embodiment, the nanoparticles are metal-organic nanoparticles. In one embodiment, the nanoparticles include different metal-organic nanoparticles. In one embodiment, the nanoparticles comprise silica. In one embodiment, the nanoparticles comprise iron oxide. In one embodiment, the nanoparticles are linked via a metal-phenolic interaction. In one embodiment, the nanoparticles are linked via a boronic acid-phenolic acid interaction. In one embodiment, the nanoparticles are linked via a thiol linkage. In one embodiment, the linkage is reversible.

REFERENCES

Blair et al., *Cytometry*, 7:171 (1986).
Croissant et al., *Adv. Mater.*, 29:1604634 (2017).
Desai et al., *Chem. Commun.*, 51:6111 (2015).
Durfee et al., *ACS Nano*, 10:8325 (2016).
Ejima et al. (2013) *Science*, 341:154 (2013).
Evans et al., *Trends In Plant Science*, 2:152 (1997).
Fleischer and Payne, *Acc. Chem. Res.*, 47:2651 (2014).
Furukawa et al., *Science*, 341:1230444 (2013).
Gándara et al., *Chem. Eur. J.*, 18:10595 (2012).
Guadamillas et al., *J. Cell Sci.*, 124:3189 (2011).
Ho and Bennett, *Science*, 360:150 (2018).
Horcajada et al., *Chem, Commun.*, _____:2820 (2007).
Jiang et al., *Nat. Commun.*, 4:2225 (2013).
Lee et al., *Angew. Chem. Int. Ed.*, 53:8056 (2014).
Lee et al., *Science*, 318:426 (2007).
Li et al., *ACS Nano*, 10:1317 (2016).
Liang et al., *Adv. Mater.*, 28:7910 (2016).
Lu et al., *Chem. Asian J.*, 8:69 (2013).
Mao et al., *Nat. Mater.*, 16:236 (2017).
Nel et al., *Science*, 311:622 (2006).
Oliveira et al., *Chemistry—An Asian Journal*, 11:1753 (2016).
Oliver-Pharr, *J. Mater. Res.*, 7:1564 (1992).
Pan et al., *Chem. Commun.*, 47:2071-2073 (2011).
Park et al., *Acc. Chem. Res.*, 49:792 (2016).
Park et al., *Adv. Mater.*, 26:2001 (2014).
Park et al., *Angew. Chem. Int. Ed.*, 53:12420 (2014).
Parks et al., *Nat. Rev. Cancer*, 13:611 (2013).
Riccò et al., Metal-Organic Frameworks for Cell and Virus Biology: A Perspective. ACS Nano (2018)
Talalay et al., *Proc. Natl. Acad. Sci.*, 104:17500 (2007).
Toshchakov et al., *Nat. Immunol.*, 3:392 (2002).

Verma and Stellacci, *Small,* 6:12 (2010).
Wuttke et al., *Chem. Commun.,* 51:15752 (2015).
Youn et al., *Angew. Chem. Int. Ed.,* _____:_____ (2017).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An enveloped viable mammalian cell comprising:
   a viable mammalian cell; and
   a plurality of linked nanoparticles enveloping the cell, wherein each of the nanoparticles has a diameter of 15 nm to 250 nm, and wherein the nanoparticles are linked via a metal-phenolic interaction, a boronic acid-phenolic acid interaction, or via a thiolated polyethylene glycol.

2. The enveloped mammalian cell of claim 1 wherein the cell is a human cell.

3. The enveloped mammalian cell of claim 1 wherein each of the nanoparticles has a diameter of 50 nm to 250 nm.

4. The enveloped mammalian cell of claim 1 wherein the nanoparticles are metal-organic nanoparticles.

5. The enveloped mammalian cell of claim 4 wherein the nanoparticles comprise Zn, Fe, Zr, Co or iron oxide.

6. The enveloped mammalian cell of claim 1 wherein the nanoparticles comprise silica.

7. The enveloped mammalian cell of claim 1 wherein the nanoparticles are functionalized with amine or phenol prior to linking.

8. The enveloped mammalian cell of claim 1 wherein the linkage is reversible.

9. The enveloped mammalian cell of claim 8 wherein the linkage is reversible with a metal chelator.

10. The mammalian cell of claim 1 wherein the linked nanoparticles are not permeable by a molecule having a diameter of about 5 nm or greater.

11. The enveloped mammalian cell of claim 1 wherein the linked nanoparticles are permeable by a molecule having a diameter of less than about 3 nm.

* * * * *

UNITED STATES PATENT AND TRADEMARK OFFICE
CERTIFICATE OF CORRECTION

PATENT NO. : 12,252,708 B2
APPLICATION NO. : 17/277256
DATED : March 18, 2025
INVENTOR(S) : Guo et al.

It is certified that error appears in the above-identified patent and that said Letters Patent is hereby corrected as shown below:

On the Title Page

On page 4, in Column 1, under item (56) "Other Publications", Line 38, delete "ACtion" and insert --Action-- therefor On page 5, in Column 2, under item (56) "Other Publications", Line 60, delete "malled" and insert --mailed-- therefor On page 10, in Column 1, under item (56) "Other Publications", Line 22, delete "cylokine" and insert --cytokine-- therefor In the Claims In Column 22, Line 6, in Claim 5, delete "Co" and insert --Co,-- therefor In Column 22, Line 16, in Claim 10, after "The", insert --enveloped--

Signed and Sealed this
Fourteenth Day of October, 2025

John A. Squires
*Director of the United States Patent and Trademark Office*